(12) United States Patent
Bittermann et al.

(10) Patent No.: US 9,745,339 B2
(45) Date of Patent: Aug. 29, 2017

(54) LIGANDS FOR ANTIBODY AND FC-FUSION PROTEIN PURIFICATION BY AFFINITY CHROMOTOGRAPHY IV

(71) Applicant: GRAFFINITY PHARMACEUTICALS GMBH, Heidelberg (DE)

(72) Inventors: Holger Bittermann, Schriesheim (DE); Marc Arnold, Spechbach (DE); Thomas Neumann, Heidelberg (DE); Inge Ott, Ketsch (DE); Kristina Schmidt, Schriesheim (DE); Renate Sekul, Schriesheim (DE)

(73) Assignee: NOVALIX DEUTSCHLAND GMBH, Mannheim (DE)

( * ) Notice: Subject to any disclaimer, the term of this patent is extended or adjusted under 35 U.S.C. 154(b) by 0 days.

(21) Appl. No.: 14/377,661

(22) PCT Filed: Feb. 8, 2013

(86) PCT No.: PCT/EP2013/052564
§ 371 (c)(1),
(2) Date: Aug. 8, 2014

(87) PCT Pub. No.: WO2013/117707
PCT Pub. Date: Aug. 15, 2013

(65) Prior Publication Data
US 2016/0009760 A1    Jan. 14, 2016

(30) Foreign Application Priority Data

Feb. 8, 2012   (EP) ..................... 12154471

(51) Int. Cl.
| C07K 1/22 | (2006.01) |
|---|---|
| C07D 417/12 | (2006.01) |
| C07D 513/04 | (2006.01) |
| C07D 403/12 | (2006.01) |
| C07D 413/12 | (2006.01) |
| C07D 231/56 | (2006.01) |
| C07K 16/06 | (2006.01) |
| C07K 16/22 | (2006.01) |
| C07K 16/28 | (2006.01) |
| C07K 16/10 | (2006.01) |
| B01J 20/289 | (2006.01) |
| B01J 20/32 | (2006.01) |
| B01D 15/38 | (2006.01) |
| C07D 417/14 | (2006.01) |
| C07D 405/14 | (2006.01) |
| C07D 417/04 | (2006.01) |

(52) U.S. Cl.
CPC ............ C07K 1/22 (2013.01); B01D 15/3804 (2013.01); B01D 15/3809 (2013.01); B01J 20/289 (2013.01); B01J 20/321 (2013.01); B01J 20/3204 (2013.01); B01J 20/3208 (2013.01); B01J 20/3212 (2013.01); B01J 20/3219 (2013.01); B01J 20/3274 (2013.01); C07D 231/56 (2013.01); C07D 403/12 (2013.01); C07D 405/14 (2013.01); C07D 413/12 (2013.01); C07D 417/04 (2013.01); C07D 417/12 (2013.01); C07D 417/14 (2013.01); C07D 513/04 (2013.01); C07K 16/065 (2013.01); C07K 16/1027 (2013.01); C07K 16/22 (2013.01); C07K 16/2863 (2013.01); C07K 16/2866 (2013.01)

(58) Field of Classification Search
CPC ............ B01D 15/3804; B01D 15/3809; B01J 20/289; B01J 20/3204; B01J 20/3208; B01J 20/321; B01J 20/3212; B01J 20/3219; B01J 20/3274; C07D 231/56; C07D 403/12; C07D 405/14; C07D 413/12; C07D 417/04; C07D 417/12
See application file for complete search history.

(56) References Cited

U.S. PATENT DOCUMENTS

| 6,479,531 B1 | 11/2002 | Kalindjian et al. | |
|---|---|---|---|
| 2001/0045384 A1* | 11/2001 | Stipanovic | ............... B01J 20/32 210/198.2 |
| 2005/0065066 A1 | 3/2005 | Kaarsholm et al. | |
| 2013/0131321 A1* | 5/2013 | Bittermann | ........ B01D 15/3804 530/387.3 |

FOREIGN PATENT DOCUMENTS

| WO | WO 97/41856 A1 | 11/1997 |
|---|---|---|
| WO | WO 01/83515 A2 | 11/2001 |

(Continued)

OTHER PUBLICATIONS

Chase, "Prediction of the Performance of Preparative Affinity Chromatography", Journal of Chromatography, vol. 297 (1984), pp. 179-202.

(Continued)

*Primary Examiner* — Galina Yakovleva

(74) *Attorney, Agent, or Firm* — Paul D. Strain, Esq.; Strain & Strain PLLC

(57) ABSTRACT

The present invention relates to the use, for affinity purification of an antibody or an fragment of an antibody, of a ligand-substituted matrix comprising a support material and at least one ligand covalently bonded to the support material, the ligand being represented by formula (I)

$$L-(Sp)_v-Ar^1-Am-Ar^2 \quad (I)$$

wherein L, SP, $Ar^1$, AM, $Ar^2$ and v are defined herein.

16 Claims, No Drawings

(56) References Cited

FOREIGN PATENT DOCUMENTS

| WO | WO 2007/117465 A2 | 10/2007 |
|---|---|---|
| WO | WO 2009/138714 A1 | 11/2009 |
| WO | WO 2009/141384 A2 | 11/2009 |
| WO | WO 2010/084425 A1 | 7/2010 |
| WO | WO 2011/104307 A2 | 9/2011 |

OTHER PUBLICATIONS

Arakawa et al., "MEP chromatography of antibody and Fc-fusion protein using aqueous arginine solution", Protein Expression and Purification, vol. 63 (2009), pp. 158-163.

Roque et al., "Antibodies and Genetically Engineered Related Molecules: Production and Purification", Biotechnol. Prog., vol. 20 (2004), pp. 639-654.

Carson, "Flexibility—the guiding principle for antibody manufacturing", Nature Biotechnology, vol. 23, No. 9 (2005), 6 pgs.

Coffman et al., "High-Throughput Screening of Chromatographic Separations: I. Method Development and Column Modeling", Biotechnology and Bioengineering, vol. 100, No. 4 (2008), pp. 605-618.

Heegaard et al., "Interactions of charged ligands with $\beta_2$-microglobulin conformers in affinity capillary electrophoresis", Biochimica et Biophysica Acta, vol. 1753 (2005), pp. 131-140.

Pignataro et al., "Rhodium-Catalyzed Asymmetric Hydrogenation of Olefins with PhthalaPhos, a New Class of Chiral Supramolecular Ligands", Chem. Eur. J., vol. 18 (2012), pp. 1383-1400.

Hober et al., "Protein A chromatography for antibody purification", Journal of Chromatography B, vol. 848 (2007), pp. 40-47.

Ghose et al., "Evaluation and comparison of alternatives to Protein A chromatography Mimetic and hydrophobic charge induction chromatographic stationary phases", Journal of Chromatography A, vol. 1122 (2006), pp. 144-152.

"Pyrazole", A print-out retrieved from http://en.wikipedia.org/wiki/Pyrazole on May 13, 2015.

Bittermann, U.S. PTO Office Action, U.S. Appl. No. 13/813,860, Jan. 15, 2016, 16 pgs.

Bittermann, U.S. PTO Office Action, U.S. Appl. No. 13/813,860, May 15, 2015, 21 pgs.

Bittermann, U.S. PTO Restriction Requirement, U.S. Appl. No. 13/813,860, Feb. 18, 2015, 12 pgs.

Dufresne et al., "Cholecystokinin and Gastrin Receptors", Pysiol. Rev., 2006, vol. 86, No. 3, pp. 805-847.

International Search Report, PCT/EP2011/063392, Mar. 16, 2012, 3 pgs.

International Search Report, PCT/EP2013/052564, May 23, 2013, 6 pgs.

\* cited by examiner

LIGANDS FOR ANTIBODY AND FC-FUSION PROTEIN PURIFICATION BY AFFINITY CHROMOTOGRAPHY IV

CROSS-REFERENCE TO RELATED PATENT APPLICATIONS

This application is a National Stage of International Application No. PCT/EP2013/052564, filed Feb. 8, 2013, which is based upon and claims the benefit of priority from prior European Patent Application No. 12154471.2, filed Feb. 8, 2012, the entire contents of all of which are incorporated herein by reference in their entirety.

BACKGROUND AND BRIEF DESCRIPTION

The present invention relates to the field of protein separation, preferably the purification of monoclonal and polyclonal antibodies and fusion proteins containing an immunoglobulin Fc segment, by affinity separation techniques, in particular chromatography using small molecule ligands.

Immunoglobulins are a class of soluble proteins found in body fluids of humans and other vertebrates. They are also termed "antibodies" and play a key role in the processes of recognition, binding and adhesion of cells. Antibodies are oligomeric glycoproteins which have a paramount role in the immune system by the recognition and elimination of antigens, in general bacteriae and viruses.

The polymeric chain of antibodies is constructed such that they comprise so-called heavy and light chains. The basic immunoglobulin unit consists of two identical heavy and two identical light chains connected by disulfide bridges. There are five types of heavy chains ($\alpha$, $\gamma$, $\delta$, $\epsilon$, $\mu$), which determine the immunoglobulin classes (IgA, IgG, IgD, IgE, IgM). The light chain group comprises two subtypes, $\lambda$ and $\kappa$.

IgGs are soluble antibodies, that can be found in blood and other body fluids. They are built by B-cell derived plasma cells as response to and to neutralize bacterial or other pathogens. An IgG is an Y-shaped glycoprotein with an approximate molecular weight of 150 kDa, consisting of two heavy and two light chains. Each chain is distinguished in a constant and in a variable region. The two carboxy terminal domains of the heavy chains are forming the Fc fragment ("constant fragment"), the amino terminal domains of the heavy and light chains are recognizing the antigen and are named Fab fragment ("antigen-binding fragment").

Fc fusion proteins are created through a combination of an antibody Fc fragment and a protein or protein domain that provides the specificity for a given drug target. Examples are domain antibody-Fc fusion proteins, where the two heavy chains of the Fc fragments are linked either to the variable domains of the heavy ($V_H$) or light chains ($V_L$) of specific antibodies. Other Fc fusion proteins are combinations of the Fc fragment with any type of therapeutic proteins or protein domains. The Fc part is considered to add stability and deliverability to the protein drug.

Therapeutic antibodies and Fc fusion proteins are used to treat various diseases, prominent examples include rheumatoid arthritis, psoriasis, multiple sclerosis and many forms of cancer. Therapeutic antibodies can be monoclonal or polyclonal antibodies. Monoclonal antibodies are derived from a single antibody producing cell line, showing identical specificity towards a single antigen. Possible treatments for cancer involve antibodies that are neutralizing tumour cell specific antigens. Bevacizumab (AVASTIN, Genentech) is a monoclonal antibody which neutralizes the vascular endothelial growth factor (VEGF), thereby preventing the growth of new blood vessels into the tumour tissue.

Therapeutic fusion proteins such as Etanercept (ENBREL, Amgen, TNF-Receptor domain linked to Fc fragment) or Alefacept (AMEVIVE, Biogen Idec, LFA-3 linked to Fc portion of human IgG1) are used or developed as drugs against autoimmune diseases.

Protein bioseparation which refers to the recovery and purification of protein products from various biological feed streams is an important unit operation in the food, pharmaceutical and biotechnological industry. More and more therapeutic monoclonal antibodies (Mabs) and fusion proteins are entering the market or are currently in clinical development. Such proteins require an exceptionally high purity which is achieved by elaborate multi-step purification protocols. Downstream processing and purification constitute about 50 to 80% of the manufacturing cost, hence considerable efforts are under way to develop new or improve existing purification strategies (1).

Affinity chromatography is one of the most effective chromatographic methods for protein purification. It is based on highly specific protein-ligand interactions. The ligand is immobilized covalently on the stationary phase which is used to capture the target protein from the feed stock solution. Affinity ligands can bind their target with high specificity and selectivity, enabling up to thousand fold higher enrichment at high yields even from complex mixtures.

Typically, affinity chromatography on protein A is the first step in most Mab and Fc fusion protein purification schemes. Protein A is a cell wall associated protein exposed on the surface of the bacterium *Staphylococcus aureus*. It binds with nanomolar affinity to the constant part (Fc domain) of immunoglobulins from various species, in particular to human subtypes $IgG_1$, $IgG_2$ and $IgG_4$ (2). However, the use of Protein A is limited by leaching into the product and poor stability under harsh conditions applied for sanitization and cleaning in place procedures. The chemical stability of Protein A can be improved by using genetically engineered Protein A variants for Mab purification. Yet, the high costs of Protein A resins have resulted in the search for suitable alternatives, in particular selected from small molecules.

MABSORBENT A2P (Prometic Biosciences) is a small molecule ligand for the purification of immunoglobulins. However, the ligand does not show an appropriate selectivity (3) and is not applied in process chromatography.

Another approach uses mixed mode chromatography as primary capture step in antibody purification. The most common material is based on immobilized 2-mercaptoethylpyridine (MEP HYPERCEL, Pall Corporation), which effectively captures IgG from fermentation broth but shows lower clearance of host cell proteins (HCP) in comparison to protein A. (4).

Synthetic small molecule affinity ligands are of particular interest for the purification of therapeutic proteins due to their generally higher chemical stability and their lower production costs. Synthetic affinity ligands that are more readily available, preferably cheaper than protein-based ligands, are more robust under stringent conditions and have a selectivity comparable to or even higher than Protein A would provide a suitable solution for antibody and Fc fusion protein purification. Depending on the target protein, such affinity ligands should preferably offer the same broad applicability as Protein A, recognizing the constant Fc region of IgG type immunoglobulins and Fc fusion proteins.

The problem underlying the present invention is the provision of a small affinity ligand (compound) binding to the Fc region of antibodies and Fc fusion proteins. Preferably, the small affinity ligand shall lend itself for binding to a matrix. A further problem underlying the invention is, therefore, the provision of a matrix comprising a small affinity ligand binding to the Fc region of antibodies and Fc fusion proteins.

The problem is solved by the embodiments of the present invention as laid out hereinafter.

DETAILED DESCRIPTION

The present invention is directed to the use, for affinity purification of a protein, preferably an antibody or fragment of an antibody, of a ligand-substituted matrix comprising a support material and at least one ligand covalently bonded to the support material, the ligand-substituted matrix according to the present invention or, respectively, the ligand according to the invention being represented by formula (I)

  (I)

wherein
L is the linking point on the support material to which the ligand is attached;
Sp is a spacer group;
v is 0 or 1;
Am is an amide group —NR$^1$—C(O)—, and wherein either NR$^1$ is attached to Ar$^1$ and —C(O)— is attached to Ar$^2$, or —C(O)— is attached to Ar$^1$ and NR$^1$ is attached to Ar$^2$; and R$^1$ is hydrogen or C$_1$ to C$_4$ alkyl, more preferably hydrogen or methyl; and most preferably hydrogen;
Ar$^1$ is a 5-, 6- or 7-membered mononuclear aromatic ring or partially saturated aromatic ring connected to Sp or L via a chemical bond and which is optionally furthermore
(a) attached to a further 5- or 6-membered mononuclear aromatic ring via a chemical bond; or
(b) fused to a mononuclear or binuclear aromatic ring as part of a multinuclear ring system;
wherein Ar$^1$ is directly connected to Am via a chemical bond present on the said 5-, 6- or 7-membered aromatic ring constituting Ar$^1$, or indirectly via a chemical bond which is either present at the further 5- or 6-membered aromatic ring attached to Ar$^1$, or on the further 5- or 6-membered aromatic ring fused to Ar$^1$;
and wherein Ar$^1$ is either not further substituted or attached to at least one substituent selected from C$_1$ to C$_4$ alkyl; C$_3$ and C$_4$ cycloalkyl; C$_2$ to C$_4$ alkenyl; C$_2$ to C$_4$ alkynyl; a halogen; C$_1$ to C$_4$ haloalkyl; hydroxyl-substituted C$_1$ to C$_4$ alkyl; C$_1$ to C$_4$ alkoxy; hydroxyl-substituted C$_1$ to C$_4$ alkoxy; halogen-substituted C$_1$ to C$_4$ alkoxy; C$_1$ to C$_4$ alkylamino; C$_1$ to C$_4$ alkylthio; —NO$_2$; =O; =S; =NH; —OH; and combinations thereof;
Ar$^2$ is a 5- or 6-membered mononuclear aromatic ring which is unsubstituted, or via a chemical bond attached to at least one substituent selected from C$_1$ to C$_6$ alkyl; C$_3$ to C$_6$ cycloalkyl; C$_2$ to C$_6$ alkenyl; C$_5$ and C$_6$ cycloalkenyl; C$_2$ to C$_6$ alkynyl; a halogen; C$_1$ to C$_6$ haloalkyl; hydroxyl-substituted C$_1$ to C$_6$ alkyl; C$_1$ to C$_6$ alkoxy; hydroxyl-substituted C$_1$ to C$_6$ alkoxy; halogen-substituted C$_1$ to C$_6$ alkoxy; C$_1$ to C$_6$ alkylamino; C$_1$ to C$_6$ alkylthio; carbamoyl; C$_1$ to C$_4$ alkylenedioxy, preferably methylenedioxy and ethylenedioxy; —OH; —SH;
a 5- or 6-membered mononuclear aromatic ring; and combinations thereof; and wherein Ar$^2$ optionally, further to the substituents to which it may be attached via a chemical bond as cited above, is fused to a 5- or 6-membered mononuclear aromatic ring as part of a multinuclear ring system.

Formula (I) may represent the ligand according to the invention or the ligand-substituted matrix according to the invention. In case L is regarded as being a part of the support material/matrix of the invention, then formula (I) represents the ligand-substituted matrix. In case L is not regarded as being a part of the support material/matrix, then formula (I) represents the ligand, after being attached to the matrix. In the context of the present invention, formula (I) preferably represents the ligand after attachment to the matrix. Within this interpretation, the ligand according to the invention, before being attached to the support material/matrix, is preferably represented by formula (II), see below.

The ligand according to the present invention (after attachment to the support material/matrix) or, respectively, the ligand-substituted support material/matrix of the present invention, in accordance with the formula (I), has the structure according to formula (Ia), in one embodiment of the invention. In a further embodiment of the invention, the ligand according to the present invention (after attachment to the support material/matrix) or, respectively, the ligand-substituted matrix of the present invention, in accordance with the formula (I), has the structure according to formula (Ib). In either formula (Ia) and (Ib), L, Sp, N, R$^1$, Ar$^1$ and Ar$^2$ and the integer v have the meanings defined above in connection with formula (I)

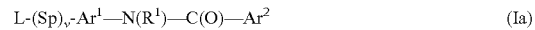  (Ia)

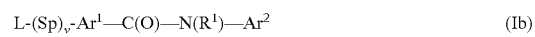  (Ib)

Ligands according to the present invention bind to polyclonal and monoclonal IgG of human origin, in particular human IgG$_1$, IgG$_2$, IgG$_3$ and IgG$_4$ and polyclonal and monoclonal IgGs from different animal species such as rabbit and mouse immunoglobulins.

As L is an appropriate entity on the support material/matrix, the ligand-substituted matrix can also be depicted as in Fig (Ic), with M being the matrix/support material and the other variables having the meaning as laid out in connection with formula (I).

  (Ic)

The present invention is also directed to the ligand-substituted matrix and the ligands (which may also be termed "compounds") before and after being attached to the matrix at the linking point L, optionally via a spacer group Sp. The matrix comprises the support material, i.e. the matrix is entirely composed of the support material, or the support material forms a part of the matrix, which comprises components further to the support material.

The present invention also includes the ligand-substituted matrix as specified in the context of the present invention, wherein the matrix furthermore comprises at least one protein, preferably an antibody or a fragment of an antibody, bound to the ligand. The antibody or the antibody fragment is, preferably, an IgG type antibody, or an Fc fusion protein. In a further preferred embodiment, the ligand binds to an Fc fragment or domain of the antibody or the fusion protein. In a further preferred embodiment, the Fc fragment or domain or the antibody belongs to the IgG antibody class, more preferably to human, IgG or to polyclonal or monoclonal IgG of human origin, in particular to IgG$_1$, IgG$_2$, IgG$_3$ and IgG$_4$.

The present invention thus comprises a ligand or compound, wherein the compound binds to a protein, preferably an antibody or fragment of an antibody, the ligand or compound, before attachment to the support material/matrix, having the formula $$(SpP)_v\text{—}Ar^1\text{—}Am\text{—}Ar^2 \quad (II)$$

wherein L, v, $Ar^1$, Am and $Ar^2$ have the meanings defined hereinafter in connection with formula (I), and wherein SpP is a spacer precursor, as specified below. The present invention is furthermore drawn to the use of the ligand for affinity purification of an antibody or an fragment of an antibody, preferably after attaching the ligand to an appropriate matrix as specified in the present application.

If v in formula (I) is 0, then the ligand is or will be directly bonded to L. In other embodiments the ligand is or will be bonded to the support material via a spacer group Sp. This applies when v in formula (I) is different from 0.

L in the above formula (I) is the linking point, also referred to as "point of attachment". The person skilled in the art is aware of appropriate linking points/points of attachment.

It is understood that the linking point L is either directly connected with the ligand/compound or via a spacer. L is an appropriate entity on the support material which lends itself for linking the ligands of the present invention to the support material. Appropriate entities are known to the person skilled in the art. Typically L is or may be part of an entity resulting from the reaction of an appropriate functional group on the support material with a corresponding functional group on the precursor compound of the ligand to form the matrix-bound ligand. The precursor compound of the ligand (which is reacted with the support matrix to form the ligand-substituted matrix) comprises, in one embodiment of the invention, a spacer precursor. "Spacer precursor" relates to the chemical entity which forms the part of the spacer remaining after formation of the ligand-substituted matrix and which contains an appropriate functional group (precursor group) for the formation of the linking point L by reaction with an appropriate group (precursor group) on the support material, see below. If the precursor compound of the ligand does not contain a spacer precursor (and will thus be directly connected to the support material via a bond), the appropriate functional group (precursor group) is attached to the ligand itself.

In one preferred embodiment, L is directly connected via a bond, preferably a single bond, to the ligand according to formula I. As L is an entity on the support material, the bound ligand is thus connected to the support material via L. In this context, the term "support material" refers to polymers known to the person skilled in the art and available on the market which lend themselves for the purposes of the present invention.

The ligands according to the present invention contain the structural unit $$\text{—}Ar^1\text{—}Am\text{—}Ar^2 \quad (III)$$

wherein $Ar^1$, Am and $Ar^2$ in formula (III) have the meanings and preferable meanings defined hereinafter and in other parts of the specification and the examples in connection with formulae (I) and (II). The structural unit as depicted in (III) is present in the ligands after being attached to the support material/matrix and before being attached to the support material/matrix.

A ligand as depicted in formula (I), and/or as depicted in formula (II), or containing the structural unit as depicted in formula (III), binds to proteins, preferably antibodies, preferably IgG type antibodies and to Fc fusion proteins, more particularly to an Fc fragment or domain of the antibody or the fusion protein, wherein most preferably the Fc fragment or domain or the antibody belongs to the IgG antibody class, more preferably to human, IgG or to polyclonal or monoclonal IgG of human origin, in particular to $IgG_1$, $IgG_2$, $IgG_3$ and $IgG_4$.

In a preferred embodiment, the ligand as defined above binds to the protein as defined above after being attached to the matrix/support material and before being attached to the matrix/support material.

In a further embodiment embodiment, the present application is directed to the use, for affinity purification of a protein, preferably an antibody or fragment of an antibody, of a ligand according to the invention as depicted in formula (I), including formulae (Ia), (Ib) and (Ic), and/or formula (II), and/or containing the structural unit as depicted in formula (III), wherein L, Sp, SpP, Am, $Ar^1$ $Ar^2$, $R^1$ and/or v have the meanings as defined in connection with formulae (I), (Ia), (Ib) (Ic), (II), and/or III), and/or defined in the present specification and examples, in particular in connection with preferred embodiments. In this embodiment, the protein, the antibody or the antibody fragment preferably have the properties laid out beforehand in connection with formula (I), (II) and III). In this embodiment, the ligand can be attached to the matrix or not attached to the matrix; preferably, in this embodiment the ligand is attached to the matrix.

A "bond" in the context of the present invention is preferably a covalent chemical bond, for example a single, double or triple bond, preferably a single bond.

In a preferred embodiment, L is a functional group or a chemical entity which is either present on the support material as such and before attaching the ligands of the invention to the support material/matrix, or which is formed in the course of attaching the ligands of the invention to the support material/matrix in the course of a chemical reaction ("new functional group").

In general, the support material comprises functional groups for the attachment of molecules, preferably the ligands of the present invention. In the context of the present invention, the functional groups are regarded as a part of the support material; this also applies in cases where the ligands of the present invention are connected to the support material via a bond (i.e. L is connected to the ligand directly via a bond, without a spacer group Sp being present, see below), and wherein the bond is directly formed between the respective ligand according to the invention and either the said functional group for the attachment of molecules on the support material or with the support material itself under transformation of said functional group to a bond, preferably a single bond.

If the bond is directly formed between the respective ligand according to the invention and the functional group for the attachment of molecules on the support material, said functional group may be interconverted to a new functional group which is subsequently attached to the support material. In the context of the present invention, the new functional group is regarded as a part of the support material/matrix and forms L, linking the ligand with the matrix via a bond, preferably a single bond.

Appropriate functional groups on the support material (or "precursor groups" i.e. present before the ligands according to the invention are attached) and, independently from each other, on the ligands of the present invention which allow the direct connection of the ligand to the support material include, but are not restricted to, —OH, —SH, —$NH_2$, >NH, methanesulphonate, trifluoromethyl sulphonate, arylsulphonate, carboxylic acid, sulphonic acid, phosphoric acid, phosphoramidite, epoxide, N-hydroxysuccinimidyl carboxylate, 1-hydroxybenzotriazolyl carboxylate, 1-hydroxy-7-azabenzotriazolyl carboxylate, fluoride, chloride, bromide, iodide, maleimide, acrylate, acrylamide, aldehyde, ketone, hydrazine, hydrazide, O-alkyl hydroxylamine, isocyanate, isothiocyanate, cyanate, thiocyanate, vinylsulphone.

Functional groups ("new functional group) to which the functional groups present on the support material may be interconverted upon linkage of the ligand include, but are not limited to, carbon-carbon single bond, carbon-nitrogen single bond, aryl alkyl ether, aryl alkyl thioether, diaryl ether, diaryl thioether, aryl alkyl amine, aryl dialkyl amine, amide, hydrazide, sulphonamide, sulphonic hydrazide, N-aryloxy amide, N-aryloxy sulphonamide, phosphate, phosphoric amide, phosphoric hydrazide, N-aryloxy phosphoric amide, hydrazone, oxime, urea, thiourea, isourea, imidocarbonate, isothiourea, imidothiocarbonate.

In a further embodiment of the invention, L is connected to a spacer group -Sp-. In this embodiment, L is a bond or a chemical unit resulting from the reaction of an appropriate functional group on the support material with an appropriate functional group (or a "precursor group") on the spacer group Sp. Accordingly, the chemical reaction between the functional group on the support material and the functional group (or "complementary group") on the spacer group Sp connects the ligand according to the invention with the support material via the linking point L.

The spacer group Sp preferably is a hydrocarbon group which may contain, in addition to C and H atoms, further atoms. Appropriate further atoms are known to the person skilled in the art. Preferred atoms include O, S, N, P, Si. The hydrocarbon group may be linear or branched or cyclic. A more detailed description of the spacer group Sp is provided below. Sp is linked to $Ar^1$ of the ligands according to the invention via a single, double or triple bond, preferably via a single bond. Furthermore, Sp is linked to a functional group (precursor group) by which the ligands of the invention can be covalently linked with functionals groups (precursor groups) present on the matrix in a chemical reaction under formation of a new functional group (also termed "final functional group", final chemical entity or connecting unit. Examples of such functional groups (precursor groups), which may be present, independently from each other, on the support material and on Sp include, but are not limited to, —OH, —SH, —$NH_2$, >NH, methanesulphonate, trifluoromethyl sulphonate, arylsulphonate, carboxylic acid, sulphonic acid, phosphoric acid, phosphoramidite, epoxide, N-hydroxysuccinimidyl carboxylate, 1-hydroxybenzotriazolyl carboxylate, 1-hydroxy-7-azabenzotriazolyl carboxylate, fluoride, chloride, bromide, iodide, maleimide, acrylate, acrylamide, aldehyde, ketone, hydrazine, hydrazide, O-alkyl hydroxylamine, isocyanate, isothiocyanate, cyanate, thiocyanate, vinylsulphone. Examples of appropriate connecting units derived from the reaction of a functional group on the support material with a functional group present on the spacer Sp include, but are not restricted to, carbon-carbon single bond, ether, aryl alkyl ether, aryl alkyl thioether, diaryl ether, thioether, diaryl thioether, dialkylamine, trialkylamine, aryl alkyl amine, aryl dialkyl amine, amide, ester, hydrazide, sulphonamide, sulphonic hydrazide, N-aryloxy amide, N-aryloxy sulphonamide, phosphate, phosphoric amide, phosphoric hydrazide, N-aryloxy phosphoric amide, hydrazone, oxime, urea, thiourea, isourea, imidocarbonate, isothiourea, imidothiocarbonate.

The spacer group Sp, generally, connects $Ar^1$ of the ligand according to formula (I) and the functional group (precursor group) that can undergo a chemical reaction with a functional group (precursor group) present on the support material, forming a final functional group (connecting unit) as described before. Generally, Sp is a linear or branched hydrocarbon which may also contain cyclic subunits. The hydrocarbon may be saturated or unsaturated, i.e. it may contain double or triple bonds. If Sp is a linear hydrocarbon, it allows the connection of one ligand moiety to one precursor group present on the support material; in contrast, if Sp is a branched hydrocarbon, it may allow the connection of more than one ligand moieties to one precursor group present on the support material. Additionally to C and H, the hydrocarbon may contain other atoms such as N, O, P, and S, preferably N and O. The carbon chain may be interrupted by other atoms or atom groups. Sp may contain combinations of different atoms or atom groups interrupting the hydrocarbon chain. Examples of atoms or atom groups that may interrupt the carbon chain of the hydrocarbon are —O—, >N—, —C(=O)N(H)—, —C(=O)N<, —O—P(=O)(—O—)$_2$. It is understood that if the hydrocarbon is interrupted by a trivalent atom or atom group such as —N<(tertiary amino), —C(=O)—N< (tertiary amide) or —O—(P=O)(—O—)$_2$ (phosphoric ester), said atom group may serve as a branching point connecting more than one ligand-connected subunits of Sp with the subunit of Sp carrying the functional group which undergoes a chemical reaction with a functional group present on the support material, ultimately resulting in the formation of the connecting unit as described before. Examples of additional suitable atom groups that may allow the introduction of a branching point into Sp include natural or unnatural trifunctional amino acids such as glutamic acid, aspartic acid, aminomalonic acid, lysine, ornithine, and diaminopropionic acid. In these cases, one of the functional groups of said trivalent moieties may serve as the functional group intended to undergo a chemical reaction with the functional group present on the support material. Typically, the total length of Sp is below 100 atoms, preferably below 50 atoms and more preferably below 30 atoms. If Sp is branched, the length as defined by the distance from the atom connecting Sp with the functional group intended to undergo a chemical reaction with a functional group on the support material to the most distant atom directly connected to a $Ar^1$ moiety, is below 100 atoms, preferably below 50 atoms and more preferably below 40 atoms.

Examples of appropriate entities of linear Sp connected to a carbon-based functional group (FG) (like, for example, carboxylic acid, aldehyde, epoxide, carboxylic acid active esters) intended to undergo a chemical reaction with a chemical group present on the support material include, but are not restricted to:

FG-$(CH_2)_n$— (alkylene) with $1 \le n \le 100$, preferably $1 \le n \le 50$, and more preferably $1 \le n \le 30$;

FG-$(CH_2)_n$—O— (alkyleneoxy) with $1 \le n \le 99$, preferably $1 \le n \le 49$, and more preferably $1 \le n \le 29$;

FG-$(CH_2)_n$—N(H)— (alkyleneamino) with $1 \le n \le 99$, preferably $1 \le n \le 49$, and more preferably $1 \le n \le 29$;

FG-$CH_2$(—O—$CH_2$—$CH_2$)$_n$— (oligoethyleneglycol) with $1 \le n \le 30$, preferably $1 \le n \le 15$, and more preferably $1 \le n \le 9$;

FG-$CH_2$(—O—$CH_2$—$CH_2$)$_n$—O— (oligoethyleneglycoloxy) with $1 \le n \le 30$, preferably $1 \le n \le 15$, and more preferably $1 \le n \le 9$;

FG-$CH_2$(—O—$CH_2$—$CH_2$)$_n$—N(H)— (oligoethyleneglycolylamino) with $1 \le n \le 30$, preferably $1 \le n \le 15$, and more preferably $1 \le n \le 9$;

FG-CH$_2$(—O—CH$_2$—CH$_2$)$_2$—N(H)—C(=O)—CH$_2$(—O—CH$_2$—CH$_2$)$_2$— (oligoethyleneglycol interrupted by amide);
FG-CH$_2$(—O—CH$_2$—CH$_2$)$_2$—N(H)—C(=O)—CH$_2$(—O—CH$_2$—CH$_2$)$_2$—O— (oligoethyleneglycolyloxy interrupted by amide);
FG-CH$_2$(—O—CH$_2$—CH$_2$)$_2$—N(H)—C(=O)—CH$_2$(—O—CH$_2$—CH$_2$)$_2$—N(H)— (oligoethyleneglycolylamino interrupted by amide).

Examples of appropriate entities of linear Sp attached to a non-carbon-based functional group (FG) (like, for example, NH$_2$, OH, SH, chloride, bromide, iodide, isocyanate, isothiocyanate) intended to undergo a chemical reaction with a chemical group present on the support material include, but are not restricted to:
FG-(CH$_2$)$_n$— (alkylene) with $1 \leq n \leq 100$, preferably $1 \leq n \leq 50$, and more preferably $1 \leq n \leq 30$;
FG-(CH$_2$)$_n$—O— (alkyleneoxy) with $1 \leq n \leq 99$, preferably $1 \leq n \leq 49$, and more preferably $1 \leq n \leq 29$;
FG-(CH$_2$)$_n$—N(H)— (alkyleneamino) with $1 \leq n \leq 99$, preferably $1 \leq n \leq 49$, and more preferably $1 \leq n \leq 29$;
FG-CH$_2$CH$_2$(—O—CH$_2$—CH$_2$)$_n$— (oligoethyleneglycol) with $1 \leq n \leq 30$, preferably $1 \leq n \leq 15$, and more preferably $1 \leq n \leq 9$;
FG-CH$_2$CH$_2$(—O—CH$_2$—CH$_2$)$_n$—O— (oligoethyleneglycolyloxy) with $1 \leq n \leq 30$, preferably $1 \leq n \leq 15$, and more preferably $1 \leq n \leq 9$;
FG-CH$_2$CH$_2$(—O—CH$_2$—CH$_2$)$_n$—N(H)— (oligoethyleneglycolylamino) with $1 \leq n \leq 30$, preferably $1 \leq n \leq 15$, and more preferably $1 \leq n \leq 9$;
FG-CH$_2$CH$_2$(—O—CH$_2$—CH$_2$)$_2$—N(H)—C(=O)—CH$_2$(—O—CH$_2$—CH$_2$)$_2$— (oligoethyleneglycol interrupted by amide);
FG-CH$_2$CH$_2$(—O—CH$_2$—CH$_2$)$_2$—N(H)—C(=O)—CH$_2$(—O—CH$_2$—CH$_2$)$_2$—O— (oligoethyleneglycolyloxy interrupted by amide);
FG-CH$_2$CH$_2$(—O—CH$_2$—CH$_2$)$_2$—N(H)—C(=O)—CH$_2$(—O—CH$_2$—CH$_2$)$_2$—N(H)— (oligoethyleneglycolylamino interrupted by amide).

Examples of appropriate entities of branched Sp including a trifunctional atom group of which one functional group serves as the functionality intended to react with the functional group present on the support material, include, but are not restricted to:
H$_2$N—C(H)(—C(=O)—N(H)—CH$_2$CH$_2$(—O—CH$_2$CH$_2$)$_2$—)(—CH$_2$—C(=O)—N(H)—CH$_2$CH$_2$(—O—CH$_2$CH$_2$)$_2$—) (glutamic acid bis(3,5-dioxa-1-octyl) amide; the NH$_2$ group is intended to react with the functional group present on the support material);
H$_2$N—C(H)(—C(=O)—N(H)—CH$_2$CH$_2$CH$_2$—)(—CH$_2$—C(=O)—N(H)—CH$_2$CH$_2$CH$_2$—) (glutamic acid bis(n-propyl) amide; the NH$_2$ group is intended to react with the functional group present on the support material);
HO—C(=O)—C(H)(—N(H)—C(=O)—CH$_2$(—O—CH$_2$CH$_2$)$_2$—)(—CH$_2$—N(H)—C(=O)—CH$_2$(—O—CH$_2$CH$_2$)$_2$—) (N,N'-bis(3,5-dioxaoctanoyl)diaminopropionic acid; the carboxylic acid group is intended to react with the functional group present on the support material);

In an embodiment of the present invention, $R^1$ is selected from: hydrogen; and $C_1$ to $C_4$ alkyl, typically linear and branched $C_1$ to $C_4$ alkyl which may comprise a cycloalkyl unit such as methyl, ethyl, n-propyl, i-propyl, n-butyl, i-butyl, sec-butyl, tert-butyl, cyclopropyl, methylcyclopropyl.

Preferably $R^1$ is selected from hydrogen, ethyl and methyl. More preferably, $R^1$ is hydrogen, or methyl. Most preferably, $R^1$ is hydrogen.

$Ar^1$ is an alicyclic or heterocyclic mononuclear aromatic ring or partially saturated aromatic ring which can have 5, 6 or 7 members. $Ar^1$ is connected to Sp or L via a chemical bond. The bond of $Ar^1$ to Sp or L can be a single bond, a double bond or a triple bond. Preferably, the bond is a single bond. $Ar^1$ can have bonds to substituents further to the chemical bond to Sp or L.

If $Ar^1$ is a heterocyclic aromatic ring or partially saturated heterocyclic aromatic ring, it contains at least one heteroatom from the group N, S and O, preferably from the group N and S, even more preferably one or more N-atoms. In all these embodiments, $Ar^1$ preferably is a 5- or 6-membered ring.

If $Ar^1$ is not attached to a further 5- or 6-membered mononuclear aromatic ring via a chemical bond or not fused to a further mononuclear or binuclear aromatic ring system, $Ar^1$ is preferably a 6-membered alicyclic aromatic ring (e.g. benzene) or a 6-membered heterocyclic ring having a N-atom (e.g. pyridine, pyrimidine, pyridazine). In this embodiment, $Ar^1$ is preferably benzene or pyridine, with pyridine being more preferred.

In one embodiment, $Ar^1$ is attached to a further 5- or 6-membered mononuclear aromatic ring via a chemical bond. The bond of $Ar^1$ to the further 5- or 6-membered aromatic ring can be a single bond or a double bond. Preferably, the bond is a single bond. The further 5- or 6-membered mononuclear aromatic ring can be alicyclic or heterocyclic, i.e. it can contain one or more heteroatoms selected from N; O; and S.

If $Ar^1$ is attached to a 5- or 6-membered mononuclear aromatic ring via a chemical bond, $Ar^1$ is preferably thiazole, oxazole, isothiazole, isoxazole or triazole, with triazole and thiazole being more preferred. The 5- or 6-membered ring attached to $Ar^1$ is preferably benzene or pyridine. The pyridine or benzene ring may be unsubstituted or be substituted by at least one entity from the group —OH, methyl, ethyl, ethoxy, monofluoromethyl, difluoromethyl, trifluoromethyl, methoxy, monofluoromethoxy, difluoromethoxy, trifluoromethoxy. Preferred units for $Ar^1$ attached to a 5- or 6-membered mononuclear aromatic ring are 4-triazolylbenzene, 5-triazolylbenzene, 2-thiazolylbenzene, 4-thiazolylbenzene, 5-thiazolylbenzene, 2-oxazolylbenzene, 4-oxazolylbenzene, 5-oxazolylbenzene, 3-isothiazolylbenzene, 4-isothiazolylbenzene, 5-isothiazolylbenzene, 3-isoxazolylbenzene, 4-isoxazolylbenzene, 5-isoxazolylbenzene, 3-isothiazolylbenzene, 4-isothiazolylbenzene, 5-isothiazolylbenzene. Further preferred units for $Ar^1$ attached to a 5- or 6-membered mononuclear aromatic ring are triazolylpyridine, thiazolylpyridine, oxazolylpyridine, isoxazolylpyridine, isothiazolylpyridine, where the pyridine unit may be attached at different positions of $Ar^1$ and the pyridine nitrogen atom may be located at different positions. More preferred units for $Ar^1$ attached to a 5- or 6-membered mononuclear aromatic ring are 4-triazolylbenzene, 4-thiazolylbenzene, 2-(4-thiazolyl)pyridine and 3-(4-thiazolyl)pyridine, with 4-triazolylbenzene being most preferred.

In the present application, the term "partially saturated aromatic ring" designates a 5, 6- or 7-membered aromatic ring of which one or more double bonds are replaced by single bonds. It is understood that the ring is not entirely saturated, i.e. at least two $sp^2$ atoms remain. One or more atoms of the partially saturated ring system may be substituted by =O.

In another embodiment, $Ar^1$ is fused to a mononuclear or binuclear aromatic ring system as part of a multinuclear aromatic ring system ring system or a partially saturated multinuclear ring system. A multinuclear ring system is a binuclear or trinuclear ring system, preferably a binuclear ring system.

In the present application, the term "partially saturated multinuclear ring system" designates a 5, 6- or 7-membered aromatic ring being fused to another mono- or binuclear aromatic ring and of which one or more double bonds are replaced by single bonds. It is understood that the ring is not entirely saturated, i.e. at least two sp$^2$ atoms remain. As the aromatic ring system to which said ring is fused is unsaturated, at least those atoms of the partially saturated ring of Ar$^1$ that are also part of the additional ring system are sp$^2$ atoms. One or more atoms of the partially saturated ring system may be substituted by =O.

If Ar$^1$ is fused to a further mononuclear or binuclear aromatic ring system, Ar$^1$ is preferably imidazole, triazole, oxazole, thiazole, isoxazole, isothiazole, pyrazole, pyrrole, imidazoline, oxazoline, tetrahydropyrazine or tetrahydro [1H]-1,4-oxazepine, with imidazole, imidazoline and pyrazole being more preferred, and imidazole and imidazoline being most preferred. The further aromatic ring system is, preferably, mononuclear. The further aromatic ring system is preferably benzene, thiophene, pyridine, pyrimidine, pyridazine, furan, thiazole or oxazole, with benzene, thiophene and pyridine being more preferred, and benzene being most preferred. The preferred, more preferred and most preferred further aromatic ring system can be unsubstituted or be substituted by at least one entity from the group —OH, methyl, ethyl, ethoxy, monofluoromethyl, difluoromethyl, trifluoromethyl, methoxy, monofluoromethoxy, difluoromethoxy, trifluoromethoxy. Units formed from Ar$^1$ fused to a further aromatic ring system are binuclear or trinuclear ring systems, preferably binuclear ring systems.

Preferred unit are benzimidazole, 2-methylbenzimidazole, 2-ethylbenzimidazole, 2-methoxybenzimidazole, benzotriazole, 2,3-dihydro[1H]benzimidazol-2-one, indazole, 1,2,3,4-tetrahydroquinoxalin-2-3-one, 2,3,4,5-tetrahydrobenzo[f][1,4]oxazepin-5-one, benzothiazole, and benzoxazole, with benzimidazole, 2-methylbenzimidazole, 2-ethylbenzimidazole, 2-methoxybenzimidazole, and 2,3-dihydro[1H]benzimidazol-2-one being more preferred and benzimidazole and 2-methylbenzimidazole being most preferred.

Ar$^1$ is directly connected to Am via a chemical bond present on the said 5-, 6- or 7-membered aromatic ring or the partially saturated aromatic ring constituting Ar$^1$, or indirectly via a chemical bond which is either present at the further 5- or 6-membered aromatic ring attached to Ar$^1$, or on the further aromatic ring fused to Ar$^1$. The direct connection of Ar$^1$ to Am can take place in all 3 alternatives described beforehand, i.e. when Ar$^1$ is attached to a further 5- or 6-membered mononuclear aromatic ring, or when Ar$^1$ is fused to a further 5- or 6-membered ring as part of a multinuclear ring system, or when none of these two alternatives applies.

In a further embodiment of the invention, Ar$^1$ is not further substituted. The term "not further substituted" denotes that besides the chemical bond to Sp or L and the one or more chemical bond(s) optionally present on Ar$^1$ (these are selected from the optional bond to Am, the bond to the further 5- or 6-membered aromatic ring and the bonds fusing Ar$^1$ to the aromatic ring), only hydrogen atoms are present on Ar$^1$ besides the above-specified bonded species.

In another embodiment, Ar$^1$ is attached to at least one substituent as specified below. The at least one substituent can be present in all alternatives described beforehand, i.e. when Ar$^1$ is directly connected to Am, or when Ar$^1$ is attached to a further 5- or 6-membered mononuclear aromatic ring, or when Ar$^1$ is fused to a further 5- or 6-membered ring as part of a multinuclear ring system, or when none of these alternatives applies (in which case Ar$^1$ must be directly connected to Am).

The at least one substituent is selected from $C_1$ to $C_4$ alkyl; $C_3$ and $C_4$ cycloalkyl; $C_2$ to $C_4$ alkenyl; $C_2$ to $C_4$ alkynyl; a halogen; $C_1$ to $C_4$ haloalkyl; hydroxyl-substituted $C_1$ to $C_4$ alkyl; $C_1$ to $C_4$ alkoxy; hydroxyl-substituted $C_1$ to $C_4$ alkoxy; halogen-substituted $C_1$ to $C_4$ alkoxy; $C_1$ to $C_4$ alkylamino; $C_1$ to $C_4$ alkylthio; —NO$_2$; =O; =S; =NH; —OH; and combinations thereof.

$C_1$ to $C_4$ alkyl includes methyl, ethyl, n-propyl, i-propyl, n-butyl, i-butyl, sec-butyl, t-butyl. $C_1$ to $C_4$ alkoxy includes methoxy, ethoxy, n-propyloxy, i-propyloxy, n-butyloxy, i-butyloxy, sec-butyloxy, t-butyloxy. $C_3$ and $C_4$ cycloalkyl is cyclopropyl, cyclobutyl and methylcyclpropyl. $C_1$ to $C_4$ haloalkyl includes: fluoro-, difluoro- and trifluoromethyl, and ethyl, n-propyl, i-propyl, n-butyl, i-butyl, sec-butyl, t-butyl substituted by one or more fluoro; chloro-, dichloro- and trichloromethyl; and ethyl, n-propyl, i-propyl, n-butyl, i-butyl, sec-butyl, t-butyl substituted by one or more chloro. Halogen-substituted $C_1$ to $C_4$ alkoxy includes: fluoro-, difluoro- and trifluoromethoxy, and ethoxy, n-propyloxy, i-propyloxy, n-butyloxy, i-butyloxy, sec-butyloxy, t-butyloxy substituted by one or more fluoro; chloro-, dichloro- and trichloromethyl; and ethoxy, n-propyloxy, i-propyloxy, n-butyloxy, i-butyloxy, sec-butyloxy, t-butyloxy substituted by one or more chloro.

Preferred substituents are methyl, ethyl, propyl, methoxy, ethoxy, difluoromethyl, trifluoromethyl, trifluoromethoxy, difluoromethoxy; cyclopropyl, hydroxymethyl, —NO$_2$, =O, with methyl, ethyl, methoxy and =O being most preferred.

The bond of Ar$^1$ to the at least one substituent can be a single bond or a double bond.

Ar$^1$ or the unit resulting from attachment of a further 5- or 6-membered aromatic ring to Ar$^1$ or the unit resulting from fusing a further 5- or 6-membered aromatic ring to Ar$^1$ is attached to Sp or L, as well as to Am.

Depending on the orientation of Am, attachment to Ar$^1$ or the unit resulting from attachment or fusing a further 5- or 6-membered aromatic ring to Ar$^1$ may be accomplished via the C=O group of Am or the NR$^1$ group of Am. Examples for appropriate entities for Ar$^1$ with no further 5- or 6-membered aromatic ring attached or fused to include but are not restricted to benzene, thiophene, pyridine, pyrimidine, pyrazine or pyridazine.

In a preferred embodiment, Ar$^1$ is benzene. In this embodiment, the NR$^1$ group or the C=O group of Am and Sp or L may be oriented ortho, meta or para towards each other, with meta or para being preferred and para being more preferred. In another preferred embodiment, Ar$^1$ is pyridine. In this embodiment, the NR$^1$ group or the C=O group of Am and Sp or L may be oriented ortho, meta or para towards each other, with meta or para being preferred and para being more preferred, while the pyridine N atom may be located in different positions.

Examples of appropriate entities resulting from Ar$^1$ attached to a further 5- or 6-membered aromatic ring include but are not restricted to 4-triazolylbenzene, 5-triazolylbenzene, 2-thiazolylbenzene, 4-thiazolylbenzene, 5-thiazolylbenzene, 2-oxazolylbenzene, 4-oxazolylbenzene, 5-oxazolylbenzene, 3-isothiazolylbenzene, 4-isothiazolylbenzene, 5-isothiazolylbenzene, 3-isoxazolylbenzene, 4-isoxazolylbenzene, 5-isoxazolylbenzene, 3-isothiazolylbenzene, 4-isothiazolylbenzene, 5-isothiazolylbenzene. In these cases the $NR^1$ group or the C=O group of Am is typically attached to the benzene moiety and may be located ortho, meta or para, preferably meta or para, relative to the 5-membered aromatic ring of $Ar^1$, while Sp or L are typically attached to the 5-membered aromatic ring of $Ar^1$ via a ring atom of $Ar^1$ which is not adjacent to the ring atom to which the benzene moiety is attached.

Further examples of appropriate entities resulting from $Ar^1$ attached to a further 5- or 6-membered aromatic ring include but are not restricted to triazolylpyridine, thiazolylpyridine, oxazolylpyridine, isoxazolylpyridine, isothiazolylpyridine, where the pyridine unit may be attached at different positions of $Ar^1$ and the pyridine nitrogen atom may be located at different positions. In these cases the $NR^1$ group or the C=O group of Am is typically attached to the pyridine moiety and may be located ortho, meta or para, preferably meta or para, relative to the 5-membered aromatic ring of $Ar^1$, while Sp or L are typically attached to the 5-membered aromatic ring of $Ar^1$ via a ring atom of $Ar^1$ which is not adjacent to the ring atom to which the pyridine moiety is attached.

Examples of appropriate units resulting from $Ar^1$ fused to a further 5- or 6-membered aromatic ring include but are not restricted to benzimidazole, benzotriazole, 2,3-dihydro[1H] benzimidazole, indazole, 1,2,3,4-tetrahydroquinoxaline, 2,3,4,5-tetrahydrobenzo[f][1,4]oxazepine, benzothiazole, benzoxazole, with benzimidazole and 2,3-dihydro[1H] benzimidazole being more preferred and benzimidazole being most preferred.

If the unit resulting from fusing $Ar^1$ to a further 5- or 6-membered aromatic ring is benzimidazole, L or Sp are typically attached in the 1- or 2-position, while the $NR^1$ group or the C=O group of Am is typically attached in the 5- or 6-position, preferably in the 5-position. If the unit resulting from fusing $Ar^1$ to a further 5- or 6-membered aromatic ring is benzotriazole, L or Sp are typically attached in the 1-position, while the $NR^1$ group or the C=O group of Am is typically attached in the 5-position. If the unit resulting from fusing $Ar^1$ to a further 5- or 6-membered aromatic ring is 2,3-dihydro[1H]benzimidazole, L or Sp are typically attached in the 1-position, while the $NR^1$ group or the C=O group of Am is typically attached in the 5-position. If the unit resulting from fusing $Ar^1$ to a further 5- or 6-membered aromatic ring is indazole, L or Sp are typically attached in the 1-position, while the $NR^1$ group or the C=O group of Am is typically attached in the 3- or in the 5-position. If the unit resulting from fusing $Ar^1$ to a further 5- or 6-membered aromatic ring is tetrahydroquinoxaline, L or Sp are typically attached in the 1-position, while the $NR^1$ group or the C=O group of Am is typically attached in the 6- or in the 7-position, preferably in the 6-position. If the unit resulting from fusing $Ar^1$ to a further 5- or 6-membered aromatic ring is 2,3,4,5-tetrahydrobenzo[f][1,4]oxazepine, L or Sp are typically attached in the 4-position, while the $NR^1$ group or the C=O group of Am is typically attached in the 7-position. If the unit resulting from fusing $Ar^1$ to a further 5- or 6-membered aromatic ring is benzothiazole, L or Sp are typically attached in the 2-position, while the $NR^1$ group or the C=O group of Am is typically attached in the 5- or 6-position. If the unit resulting from fusing $Ar^1$ to a further 5- or 6-membered aromatic ring is benzoxazole, L or Sp are typically attached in the 2-position, while the $NR^1$ group or the C=O group of Am is typically attached in the 5- or 6-position.

$Ar^2$ is an alicyclic or heterocyclic mononuclear aromatic ring which can have 5 or 6 members. $Ar^2$ is connected to Am via a chemical bond. In one embodiment, $Ar^2$ is connected to the N atom of Am; in another embodiment, $Ar^2$ is connected to the C atom of Am. Preferably, $Ar^2$ is connected to the N atom of Am. Further to the chemical bond to Am, $Ar^2$ can be attached to at least one further chemical entity, namely to at least one substituent or fused to a 5- or 6-membered mononuclear aromatic ring as part of a multinuclear ring system.

If $Ar^2$ is a heterocyclic aromatic ring, it contains at least one heteroatom from the group N, S and O, preferably from the group N and S, even more preferably at least one N-atom and at least one S-atom, most preferably two N-atoms and one S-atom. In all these embodiments, $Ar^2$ preferably is a 5- or 6-membered ring, even more preferably a 5-membered ring.

If $Ar^2$ is not fused to a further mononuclear or binuclear aromatic ring system, in one embodiment, $Ar^2$ is a 6-membered alicyclic aromatic ring (e.g. benzene) or a 6-membered heterocyclic ring having at least one N-atom (e.g. pyridine, pyrimidine, pyridazine, pyrazine or triazine). In this embodiment, $Ar^2$ is preferably benzene, pyridine, pyrazine, pyridazine or pyrimidine, with benzene and pyridazine being more preferred. In another embodiment, $Ar^2$ is a 5-membered heterocylic aromatic ring containing at least one heteroatom from the group N, S, and O, with N and S being preferred. Appropriate examples for $Ar^2$ include but are not restricted to oxazole, isoxazole, thiazole, isothiazole, 1,2,4-oxadiazole, 1,2,4-thiadiazole, 1,3,4-oxadiazole, 1,3,4-thiadiazole, pyrrole, pyrazole, imidazole, thiophene, furan. Preferred examples for $Ar^2$ are thiazole, 1,2,4-thiadiazole and 1,3,4-thiadiazole, with 1,2,4-thiadiazole and 1,3,4-thiadiazole being most preferred.

In another embodiment, $Ar^2$ is fused to a mononuclear or binuclear aromatic ring system as part of a multinuclear ring system. A multinuclear ring system is a binuclear or trinuclear ring system, preferably a binuclear ring system;

If $Ar^2$ is fused to a further mononuclear or binuclear aromatic ring system, $Ar^2$ is preferably 1H-pyrazole, thiazole, oxazole, or imidazole. If $Ar^2$ is 1H-pyrazole, the second aromatic ring system is fused to $Ar^2$ via the 4- and 5-position, while Am is attached in the 3-position. If $Ar^2$ is thiazole, the second aromatic ring is fused to $Ar^2$ via the 4- and 5-position, while Am is attached in the 2-position. If $Ar^2$ is oxazole, the second aromatic ring system is fused to $Ar^2$ via the 4- and 5-position, while Am is attached in the 2-position. If $Ar^2$ is imidazole, the second aromatic ring system is attached to $Ar^2$ via the 1- and 2-position, while Am is attached in the 4-position. Alternatively, the second aromatic ring system is attached to $Ar^2$ via the 4- and 5-position, while Am is attached in the 2-position. The further aromatic ring system is, preferably, mononuclear. The further aromatic ring system is preferably benzene, thiophene, pyridine, furan, thiazole, oxazole or imidazole. More preferably, the further aromatic ring system is benzene or thiazole. If the further aromatic ring system is thiazole, it is fused to $Ar^2$ via the 2- and 3-position. The units formed from $Ar^2$ fused to a further aromatic ring system are preferably benzoxazole (Am attached to the 2-position), benzothiazole (Am attached to the 2-position), indazole (Am attached to the 3-position) or imidazo-[2,1-b]thiazole (Am attached to the 6-position).

Instead of being fused to a second aromatic ring system, if $Ar^2$ is oxazole or thiazole, it may be fused to cyclopentene via the 4- and 5-position. The resulting units, which are also preferred units, are 5,6-dihydro-4H-cyclopentaoxazole (Am attached to the 2-position) and 5,6-dihydro-4H-cyclopentathiazole (Am attached to the 2-position), with 5,6-dihydro-4H-cyclopentathiazole being more preferred.

In a further embodiment of the invention, $Ar^2$ is not further substituted. The term "not further substituted" denotes that besides the chemical bond to Am and optionally present bonds fusing $Ar^2$ to the aromatic ring, only hydrogen atoms are present on $Ar^2$ besides the above-specified bonded species.

In another embodiment, $Ar^2$ is attached to at least one substituent as specified below. The at least one substituent can be present in all 2 alternatives described beforehand, i.e. when $Ar^2$ is fused to a further 5- or 6-membered ring as part of a multinuclear ring system, or when $Ar^2$ is not fused to a further ring. The bond of $Ar^2$ to the at least one substituent can be a single bond or a double bond. Preferably, the bond is a single bond.

$Ar^2$, via a chemical bond, can be attached to at least one substituent selected from $C_1$ to $C_6$ alkyl; $C_3$ to $C_6$ cycloalkyl; $C_2$ to $C_6$ alkenyl; $C_5$ and $C_6$ cycloalkenyl; $C_2$ to $C_6$ alkynyl; a halogen; $C_1$ to $C_6$ haloalkyl; hydroxyl-substituted $C_1$ to $C_6$ alkyl; $C_1$ to $C_6$ alkoxy; hydroxyl-substituted $C_1$ to $C_6$ alkoxy; halogen-substituted $C_1$ to $C_6$ alkoxy; $C_1$ to $C_6$ alkylamino; $C_1$ to $C_6$ alkylthio; —OH; SH; carbamoyl; $C_1$ to $C_4$ alkylenedioxy; a 5- or 6-membered mononuclear aromatic ring; and combinations thereof; and wherein $Ar^2$ optionally, further to the substituents to which it may be attached via a chemical bond as cited above, is fused to a 5- or 6-membered mononuclear aromatic ring as part of a multinuclear ring system.

$C_1$ to $C_6$ alkyl includes methyl, ethyl, n-propyl, i-propyl, n-butyl, i-butyl, sec-butyl, t-butyl, pentyl and hexyl. $C_1$ to $C_6$ alkoxy includes methoxy, ethoxy, n-propyloxy, i-propyloxy, n-butyloxy, i-butyloxy, sec-butyloxy, t-butyloxy, pentyloxy and hexyloxy. $C_3$ to $C_6$ cycloalkyl includes cyclopropyl, cyclobutyl, cyclopentyl, cyclohexyl, methylcyclpropyl, dimethylcyclopropyl, trimethylcyclopropyl, ethylcyclopropyl, propylcyclopropyl, methylethylcyclopropyl, methylcyclobutyl, dimethylcyclobutyl, ethylcyclobutyl, and methylcyclopentyl. $C_1$ to $C_6$ haloalkyl includes: fluoro-, difluoro- and trifluoromethyl, and ethyl, n-propyl, i-propyl, n-butyl, i-butyl, sec-butyl, t-butyl, propyl and hexyl substituted by one or more fluoro; chloro-, dichloro- and trichloromethyl; and ethyl, n-propyl, i-propyl, n-butyl, i-butyl, sec-butyl, t-butyl, propyl and hexyl substituted by one or more chloro. Halogen-substituted $C_1$ to $C_4$ alkoxy includes: fluoro-, difluoro- and trifluoromethoxy, and ethoxy, n-propyloxy, i-propyloxy, n-butyloxy, i-butyloxy, sec-butyloxy, t-butyloxy substituted by one or more fluoro; chloro-, dichloro- and trichloromethyl; and ethoxy, n-propyloxy, i-propyloxy, n-butyloxy, i-butyloxy, sec-butyloxy, t-butyloxy substituted by one or more chloro; $C_1$ to $C_4$ alkylenedioxy include methylenedioxy; ethylenedioxy, propylenedioxy, butylenedioxy, preferably methylenedioxy, ethylenedioxy.

Preferred substituents are methyl, ethyl, n-propyl, isopropyl, methoxy, ethoxy, difluoromethyl, trifluoromethyl, trifluoromethoxy, difluoromethoxy, cyclopropyl, hydroxymethyl, t-butyl, i-butyl, sec-butyl, fluro, chloro, carbamoyl, ethylthio, methylthio, with methyl, ethyl, carbamoyl, methoxy, ethylthio, and cyclopropyl being most preferred.

In one embodiment, the substituent to which $Ar^2$ is attached via a chemical bond is a 5- or 6-membered mononuclear aromatic ring. The bond of $Ar^2$ to the 5- or 6-membered aromatic ring can be a single bond or a double bond. Preferably, the bond is a single bond. The further 5- or 6-membered mononuclear aromatic ring can be alicylic or heterocyclic, i.e. it can contain one or more heteroatoms selected from N; O; and S.

If $Ar^2$ is attached to a 5- or 6-membered mononuclear aromatic ring via a chemical bond, $Ar^2$ is preferably oxazole, isoxazole, imidazole, pyrazole, pyrrole, thiazole, isothiazole, 1,2,4-thiadiazole, 1,3,4-thiadiazole, pyridine, pyridazine or pyrimidine. More preferably, $Ar^2$ is pyrazole, thiazole, isothiazole, 1,2,4-thiadiazole, 1,3,4-thiadiazole, or pyridazine. Most preferably, $Ar^2$ is pyrazole, thiazole, 1,2,4-thiadiazole or 1,3,4-thiadiazole. If $Ar^2$ is oxazole, Am is attached to the 2-position and the further mononuclear aromatic ring is attached to the 4- or 5-position. Alternatively, Am is attached to the 4- or 5-position, and the further mononuclear aromatic ring is attached to the 2-position. If $Ar^2$ is isoxazole, Am is attached to the 3-position, and the further mononuclear aromatic ring is attached to the 5-position. Alternatively, Am is attached to the 5-position and the further aromatic ring is attached to the 3-position. If $Ar^2$ is imidazole, Am is attached to the 2-position and the further mononuclear aromatic ring is attached to the 4-position. Alternatively, Am is attached to the 4-position and the further mononuclear aromatic ring is attached to the 2-position. If $Ar^2$ is pyrazole, Am is attached to the 3-position and the further mononuclear aromatic ring is attached to the 5-position. Alternatively, Am is attached to the 3- or 4-position and the further mononuclear aromatic ring is attached to the 1-position. If $Ar^2$ is pyrrole, Am is attached to the 2-position and the further mononuclear aromatic ring is attached to the 4-position. Alternatively, Am is attached to the 4-position and the further mononuclear aromatic ring is attached to the 2-position. Still alternatively, Am is attached to the 3-position and the further mononuclear aromatic ring is attached to the 1-position. If $Ar^2$ is thiazole, Am is attached to the 2-position and the further mononuclear aromatic ring is attached to the 4- or 5-position. Alternatively, Am is attached to the 4- or 5-position, and the further mononuclear aromatic ring is attached to the 2-position. If $Ar^2$ is isothiazole, Am is attached to the 3-position, and the further mononuclear aromatic ring is attached to the 5-position. Alternatively, Am is attached to the 5-position and the further aromatic ring is attached to the 3-position. If $Ar^2$ is 1,2,4-thiadiazole, Am is attached to the 3-position and the further mononuclear aromatic ring is attached to the 5-position. Alternatively, Am is attached to the 5-position and the further mononuclear aromatic ring is attached to the 3-position. If $Ar^2$ is 1,3,4-thiadiazole, Am is attached to the 2-position and the further mononuclear aromatic ring is attached to the 5-position. If $Ar^2$ is pyridine, Am and the further mononuclear aromatic ring are located meta or para, preferably para, relative to each other, while the nitrogen atom of the pyridine core may be located in different positions. If $Ar^2$ is pyridazine, Am is attached to the 3-position and the further mononuclear aromatic ring is attached to the 6-position. Alternatively, Am is attached to the 5-position and the further mononuclear aromatic ring is attached to the 3-position. Still alternatively, Am is attached to the 3-position and the further mononuclear aromatic ring is attached to the 5-position. If $Ar^2$ is pyrimidine, Am and the further mononuclear aromatic ring are located meta or para, preferably para, relative to each other, while the nitrogen atoms of the pyrimidine core may have different positions.

The further mononuclear 5- or 6-membered aromatic ring attached to $Ar^2$ is preferably benzene, furan, thiophene, oxazole, isoxazole, thiazole, isothiazole, or pyridine. More preferably, the further mononuclear 5- or 6-membered aromatic ring attached to $Ar^2$ is furan, oxazole, isoxazole or pyridine, with furan being most preferred. If the further mononuclear aromatic ring is furan, it is attached to $Ar^2$ via the 2- or 3-position. If the further mononuclear aromatic ring is thiophene, it is attached to $Ar^2$ via the 2- or 3-position. If the further mononuclear aromatic ring is oxazole, it is attached to $Ar^2$ via the 2-, 4- or 5-position. If the further mononuclear aromatic ring is isoxazole, it is attached to $Ar^2$ via the 3-, 4- or 5-position. If the further mononuclear aromatic ring is thiazole, it is attached to $Ar^2$ via the 2-, 4- or 5-position. If the further mononuclear aromatic ring is isothiazole, it is attached to $Ar^2$ via the 3-, 4- or 5-position. If the further mononuclear aromatic ring is pyridine, it is attached to $Ar^2$ via the 2-, 3- or 4-position.

Preferred units for $Ar^2$ attached to a 5- or 6-membered mononuclear aromatic ring are 1-phenylpyrazole (attachment to Am via the 3-position), 2-(2-furyl)pyrazole (attachment to Am via the 5-position), 4-phenylthiazole (attachment to Am via the 2-position), 5-phenylthiazole (attachment to Am via the 2-position), 2-(2-furyl)-1,3,4-thiadiazole (attachment to Am via the 5-position), 2-(3-furyl)-1,3,4-thiadiazole (attachment to Am via the 5-position), 2-(2-pyridyl)-1,3,4-thiadiazole (attachment to Am via the 5-position), 2-(3-pyridyl)-1,3,4-thiadiazole (attachment to Am via the 5-position), 2-(4-pyridyl)-1,3,4-thiadiazole (attachment to Am via the 5-position), 3-(2-furyl)-1,2,4-thiadiazole (attachment to Am via the 5-position), 4-(2-furyl)thiazole (attachment to Am via the 2-position), 5-(2-furyl)thiazol (attachment to Am via the 2-position), 2-phenyl-1,3,4-thiadiazole (attachment to Am via the 5-position), 3-phenyl-1,2,4-thiadiazole (attachment to Am via the 5-position), 4-(2-pyridyl)thiazole (attachment to Am via the 2-position), 4-(3-pyridyl)thiazole (attachment to Am via the 2-position), 4-(4-pyridyl)thiazole (attachment to Am via the 2-position) 5-(2-pyridyl)thiazole (attachment to Am via the 2-position), 5-(3-pyridyl)thiazole (attachment to Am via the 2-position), 5-(4-pyridyl)thiazole (attachment to Am via the 2-position), 3-(2-furyl)pyridazine (attachment to Am via the 6-position), 2-(5-isoxazolyl)-1,3,4-thiadiazole (attachment to Am via the 5-position), 2-(5-oxazolyl)-1,3,4-thiadiazole (attachment to Am via the 5-position), 2-(2-oxazolyl)-1,3,4-thiadiazole (attachment to Am via the 5-position).

More preferred units for $Ar^2$ attached to a 5- or 6-membered mononuclear aromatic ring are 2-(2-furyl)-1,3,4-thiadiazole (attachment to Am via the 5-position), 2-(3-furyl)-1,3,4-thiadiazole (attachment to Am via the 5-position), 3-(2-furyl)-1,2,4-thiadiazole (attachment to Am via the 5-position), 4-(2-furyl)thiazole (attachment to Am via the 2-position), 5-(2-furyl)thiazole (attachment to Am via the 2-position), 4-(2-pyridyl)thiazole (attachment to Am via the 2-position), 4-(3-pyridyl)thiazole (attachment to Am via the 2-position), 4-(4-pyridyl)thiazole (attachment to Am via the 2-position), 3-(2-furyl)pyridazine (attachment to Am via the 6-position), 2-(5-isoxazolyl)-1,3,4-thiadiazole (attachment to Am via the 5-position), 2-(5-oxazolyl)-1,3,4-thiadiazole (attachment to Am via the 5-position), 2-(2-oxazolyl)-1,3,4-thiadiazole (attachment to Am via the 5-position). Most preferred units for $Ar^2$ attached to a 5- or 6-membered mononuclear aromatic ring are 2-(2-furyl)-1,3,4-thiadiazole (attachment to Am via the 5-position), 3-(2-furyl)-1,2,4-thiadiazole (attachment to Am via the 5-position), 4-(2-pyridyl)thiazole (attachment to Am via the 2-position), 4-(3-pyridyl)thiazole (attachment to Am via the 2-position), 4-(4-pyridyl)thiazole (attachment to Am via the 2-position).

The unit resulting from $Ar^2$ being attached to a further 5- or 6-membered mononuclear aromatic ring may be, in addition to the attachment to Am, be attached to one or more substituents selected from: methyl, ethyl, methoxy, methylenedioxy (in this case, the substituent is attached to two atoms of the unit resulting from $Ar^2$ being attached to a further 5- or 6-membered mononuclear aromatic ring), ethoxy, difluoromethyl, trifluoromethyl, difluoromethoxy, trifluoromethoxy, —F, —Cl, —Br. Preferred substituents are methyl and methylenedioxy.

$Ar^2$ is either attached to a C=O group (see formula Ia) or to the $NR^1$ group (see formula Ib)

All the definitions cited beforehand in respect to various meanings of the variables L, Sp, $Ar^1$, Am, $R^1$ and $Ar^2$ depicted in formula (I) refer to embodiments of the present invention and include general embodiments, preferred embodiments, more preferred embodiments and even more preferred embodiments of each variable, independent of the fact if any one or all of the other variables besides the one under consideration refers to its general, preferred, more preferred or even more preferred embodiment. In consequence, a general embodiment of one variable can be combined with a preferred, more preferred, and even more preferred embodiment of any of the other variables.

There will now follow definitions of preferred definitions for the general formula (I).

In all the embodiments as defined below (i.e. preferred, more preferred and even more preferred), $R^1$ is hydrogen or methyl; and most preferably hydrogen.

In a preferred embodiment of the present invention, the variables of formula (I) have the following meanings:
$Ar^1$ is a 5- or 6-membered mononuclear aromatic ring or partially saturated aromatic ring containing 1, 2 or 3 N atoms or benzene; wherein the said mononuclear ring or benzene is connected to Sp or L via a chemical bond, optionally furthermore
(a) attached to benzene or thiophene via a chemical bond; or
(b) fused to benzene or thiophene as part of a multinuclear ring system;
wherein $Ar^1$ is directly connected to Am via a chemical bond present on the said aromatic ring or benzene constituting $Ar^1$, or indirectly via a chemical bond which is either present at the benzene ring or thiophene ring attached to $Ar^1$, or on the benzene ring or thiophene ring fused to $Ar^1$;
and wherein $Ar^1$ is either not further substituted or attached to at least one substituent selected from: methyl, ethyl, propyl, methoxy, ethoxy, difluoromethyl, trifluoromethyl, trifluoromethoxy, difluoromethoxy; cyclopropyl, hydroxymethyl, —$NO_2$, =O, =S; and combinations thereof; and/or
$Ar^2$ is a 5-membered mononuclear aromatic ring which is unsubstituted, or via a chemical bond attached to at least one substituent selected from: methyl, ethyl, n-propyl, isopropyl, methoxy, ethoxy, difluoromethyl, trifluoromethyl, trifluoromethoxy, difluoromethoxy, cyclopropyl, hydroxymethyl, t-butyl, i-butyl, sec-butyl, fluro, chloro, carbamoyl, ethylthio, methylthio, a 5- or 6-membered mononuclear aromatic ring; and combinations thereof; and wherein $Ar^2$ optionally, further to the substituents to which it may be attached via a chemical bond as cited above, is fused to benzene or thiazole as part of a multinuclear ring system.

In an even more preferred embodiment of the present invention, the variables of formula (I) have the following meanings:
$Ar^1$ is a 5- or 6-membered mononuclear aromatic ring or partially saturated aromatic ring selected from: imidazole, benzene, pyridine, 2,3-dihydro-1H-imidazole, and triazole, which is connected to Sp or L via a chemical bond and which is optionally furthermore
(a) attached to benzene via a chemical bond; or
(b) fused to benzene as part of a multinuclear ring system
wherein $Ar^1$ is directly connected to Am via a chemical bond present on the 5- or 6-membered aromatic ring or partially saturated aromatic ring constituting $Ar^1$, or indirectly via a chemical bond which is either present at the benzene ring attached to $Ar^1$, or on the benzene ring fused to $Ar^1$;
and wherein $Ar^1$ is either not further substituted or attached to at least one substituent selected from: methyl, ethyl, propyl, methoxy, ethoxy, difluoromethyl, trifluoromethyl, trifluoromethoxy, difluoromethoxy; cyclopropyl, hydroxymethyl, $—NO_2$, $=O$, $=S$; and combinations thereof; and/or $Ar^2$ is a 5-membered mononuclear aromatic ring containing at least one atom selected from N, S, O, preferably from N, S, which is unsubstituted, or via a chemical bond attached to at least one substituent selected from: methyl, ethyl, n-propyl, isopropyl, methoxy, ethoxy, difluoromethyl, trifluoromethyl, trifluoromethoxy, difluoromethoxy, cyclopropyl, hydroxymethyl, t-butyl, i-butyl, sec-butyl, fluro, chloro, carbamoyl, ethylthio, methylthio, preferably methyl, ethyl, methoxy, ethylthio, and cyclopropyl; a 5- or 6-membered mononuclear aromatic ring; and combinations thereof; and wherein $Ar^2$ optionally, further to the substituents to which it may be attached via a chemical bond as cited above, is fused to benzene or thiazole as part of a multinuclear ring system.

In an even more preferred embodiment of the present invention, the variables of formula (I) have the following meanings: $Ar^1$ is selected from benzimidazole, 2,3-dihydrobenzimidazole, pyridine and 4-triazolylbenzene;
wherein $Ar^1$ is connected to Sp or L via a chemical bond attached to the 1- or 2-position of benzimidazole, the 1-position of 2,3-dihydrobenzimidazole, the 2-position of pyridine or to the 1-position of the triazole part of 4-triazolylbenzene;
wherein $Ar^1$ is connected to Am via a chemical bond attached to the 5- or 6-position of benzimidazole, the 5- or 6-position of 2,3-dihydrobenzimidazole, to the 5-position of pyridine or to the 4-position of the benzene part of 4-triazolylbenzene;
and wherein $Ar^1$ is either not further substituted or attached to at least one substituent selected from: methyl, ethyl, methoxy $=S$ and $=O$; and combinations thereof and/or $Ar^2$ is a 5-membered mononuclear aromatic ring selected from 1,2,4-thiadiazole, 1,3,4-thiadiazole, and thiazole; which is unsubstituted, or via a chemical bond attached to at least one substituent selected from: methyl, ethyl, methoxy, ethylthio, and cyclopropyl; a 5- or 6-membered mononuclear aromatic ring selected from pyridine, furan, isoxazole, oxazole, isothiazole, thiazole; and combinations thereof.

The present invention also includes the ligands of the present invention (which, after being attached to the support material) form together with the support material the ligand-substituted matrix which is used in the method of the present invention. The ligands, before being attached to the matrix/support material are in accordance with the following formulae (II), (IIa) and (IIb) wherein the symbols Sp, $Ar^1$, $Ar^2$ and Am have the meanings defined above, including the preferred meanings:

$(SpP)_v—Ar^1—Am—Ar^2$ (II)

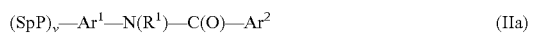

$(SpP)_v—Ar^1—N(R^1)—C(O)—Ar^2$ (IIa)

$(SpP)_v—Ar^1—C(O)—N(R^1)—Ar^2$ (IIb)

The ligands according to the present invention contain the structural unit

$—Ar^1—Am—Ar^2$ (III)

wherein $Ar^1$, Am and $Ar^2$ have the meanings defined throughout the present specification and the examples in connection with formula (I). The structural unit as depicted in (III) is present in the ligands after being attached to the support material/matrix and before being attached to the support material/matrix.

A ligand as depicted in formula (I), and/or as depicted in formula (II), and/or containing the structural unit as depicted in formula (III), binds to proteins, preferably antibodies, preferably IgG type antibodies and to Fc fusion proteins, more particularly to an Fc fragment or domain of the antibody or the fusion protein, wherein most preferably the Fc fragment or domain or the antibody belongs to the IgG antibody class, more preferably to human, IgG or to polyclonal or monoclonal IgG of human origin, in particular to $IgG_1$, $IgG_2$, $IgG_3$ and $IgG_4$.

In a preferred embodiment, the ligand as defined above binds to the protein as defined above after being attached to the matrix/support material and before being attached to the matrix/support material.

The ligands according to formulae (II), (IIa) and (IIb) comprise the spacer precursor group SpP attached to the ligand.

The ligands according to formulae (II), (IIa) and (IIb) can serve as precursors for the synthesis of further compounds not having the spacer group attached. The named compounds are generated after cleavage of the spacer group and, as the case may be, conversion of the functionality present in the ligands which is connected to SpP, to any other appropriate functionality known to the person skilled in the art. Appropriate reactions to that end are known to person skilled in the art. The resulting compounds are also included in the present invention.

Preferred ligands of the matrix according to the present invention are depicted below wherein in each formula the very left N atom is connected to the linking point L which is not shown. All formulae below show the spacer precursor group (SpP) attached to the ligands:

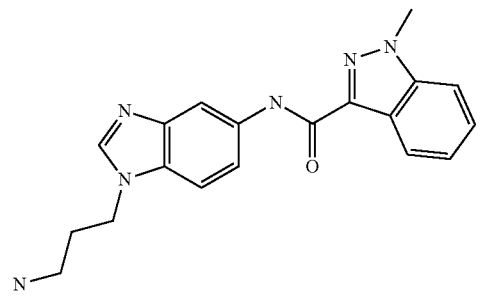 [SMILES: Cn1nc(C(=O)Nc2ccc3c(c2)ncn3CCCN)c2ccccc21]

1-(3-Amino-1-propyl)-5-[(1-methylindazol-3-yl)carboxamido]benzimidazole (L01)

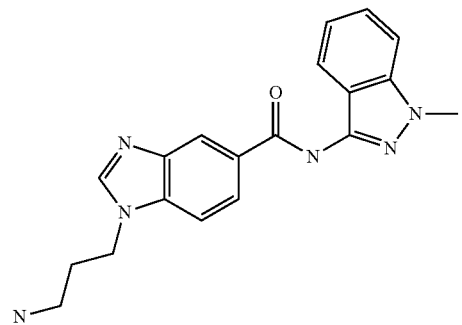 [SMILES: Cn1nc(NC(=O)c2ccc3c(c2)ncn3CCCN)c2ccccc21]

1-(3-Amino-1-propyl)benzimidazole-5-carboxylic acid N-(1-methyl-3-indazolyl) amide (L02)

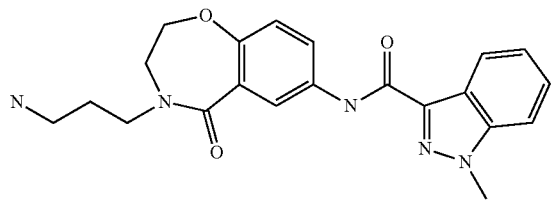 [SMILES: Cn1nc(C(=O)Nc2ccc3c(c2)C(=O)N(CCCN)CCO3)c2ccccc21]

4-(3-Amino-1-propyl)-7-[(1-methylindazol-3-yl)carboxamido]-2,3,4,5-tetrahydrobenzo[f][1,4]oxazepin-5-one (L03)

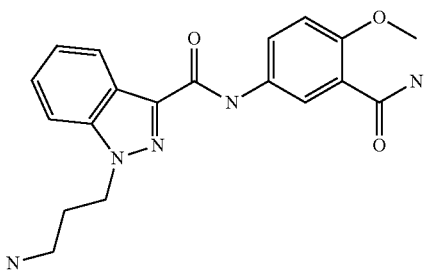 [SMILES: COc1ccc(NC(=O)c2nn(CCCN)c3ccccc23)cc1C(N)=O]

1-(3-Amino-1-propyl)indazole-3-carboxylic acid N-(3-carbamoyl-4-methoxyphenyl) amide (L04)

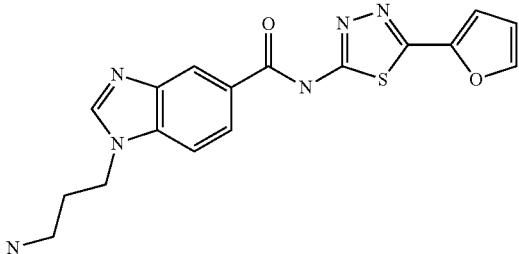 [SMILES: NCCCn1cnc2cc(C(=O)Nc3nnc(-c4ccco4)s3)ccc21]

1-(3-Amino-1-propyl)benzimidazole-5-carboxylic acid N-[5-(2-furyl)-1,3,4-thiadiazol-2-yl]amide (L05)

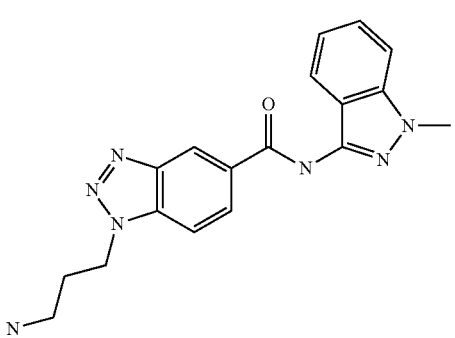 [SMILES: Cn1nc(NC(=O)c2ccc3c(c2)nnn3CCCN)c2ccccc21]

1-(3-Amino-1-propyl)benzotriazole-5-carboxylic acid N-(1-methylindazol-3-yl) amide (L06)

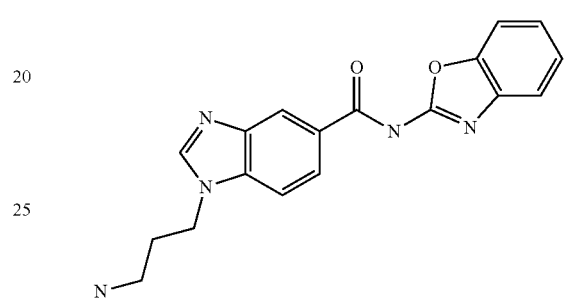

1-(3-Amino-1-propyl)benzimidazole-5-carboxylic acid N-(2-ethyl-1,3,4-thiadiazol-5-yl) amide (L07)

1-(3-Amino-1-propyl)benzimidazole-5-carboxylic acid N-(benzoxazol-2-yl) amide (L08)

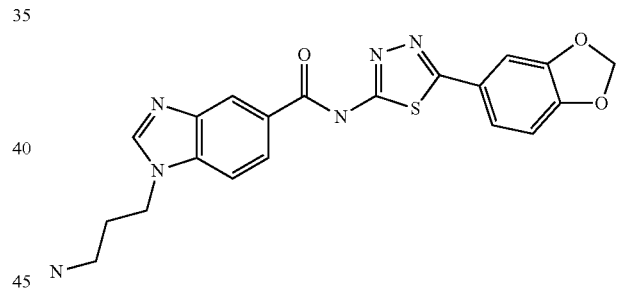

1-(3-Amino-1-propyl)benzimidazole-5-carboxylic acid N-[2-(3,4-methylenedioxyphenyl)-1,3,4-thiadiazol-5-yl] amide (L09)

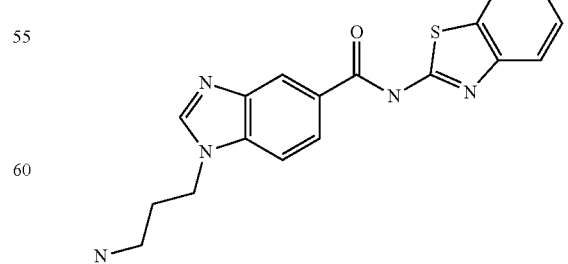

1-(3-Amino-1-propyl)benzimidazole-5-carboxylic acid N-(benzothiazol-2-yl) amide (L10)

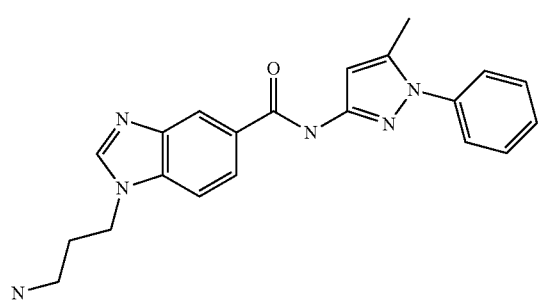 [SMILES: Cc1cc(NC(=O)c2ccc3c(c2)ncn3CCCN)nn1-c1ccccc1]

1-(3-Amino-1-propyl)benzimidazole-5-carboxylic acid N-(5-methyl-1-phenylpyrazol-3-yl) amide (L11)

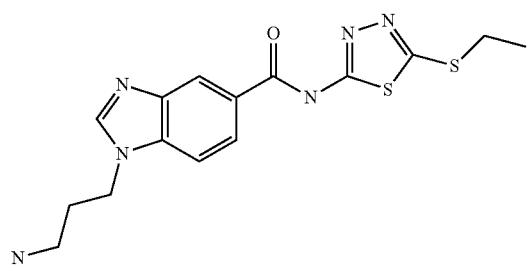 [SMILES: CCSc1nnc(NC(=O)c2ccc3c(c2)ncn3CCCN)s1]

1-(3-Amino-1-propyl)benzimidazole-5-carboxylic acid N-(2-ethylthio-1,3,4-thiadiazol-5-yl) amide (L12)

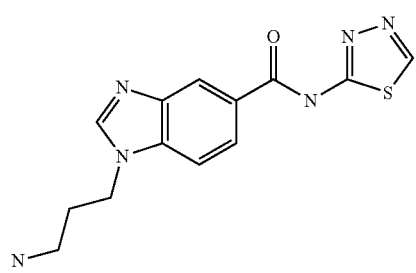 [SMILES: NCCCn1cnc2cc(C(=O)Nc3nncs3)ccc21]

1-(3-Amino-1-propyl)benzimidazole-5-carboxylic acid N-(1,3,4-thiadiazol-2-yl) amide (L13)

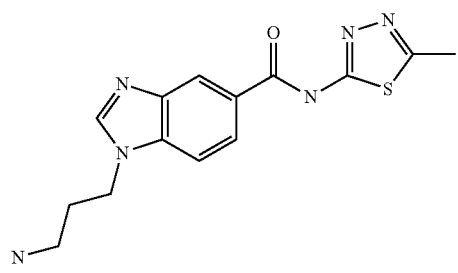 [SMILES: Cc1nnc(NC(=O)c2ccc3c(c2)ncn3CCCN)s1]

1-(3-Amino-1-propyl)benzimidazole-5-carboxylic acid N-(2-methyl-1,3,4-thiadiazol-5-yl) amide (L14)

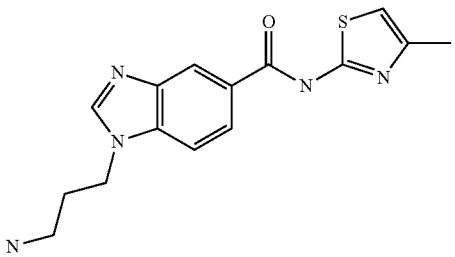 [SMILES: Cc1csc(NC(=O)c2ccc3c(c2)ncn3CCCN)n1]

1-(3-Amino-1-propyl)benzimidazole-5-carboxylic acid N-(4-methylthiazol-2-yl) amide (L15)

1-(3-Amino-1-propyl)benzimidazole-5-carboxylic acid N-(thiazol-2-yl) amide (L16)

1-(3-Amino-1-propyl)benzimidazole-5-carboxylic acid N-(5-methylthiazol-2-yl) amide (L17)

4-[(3-Amino-1-propyl)amino]-3-nitrobenzoic acid N-[5-(2-furyl)-1,3,4-thiadiazol-2-yl]amide (L18)

6-[(3-Amino-1-propyl)amino]nicotinic acid N-[5-(2-furyl)-1,3,4-thiadiazol-2-yl]amide (L19)

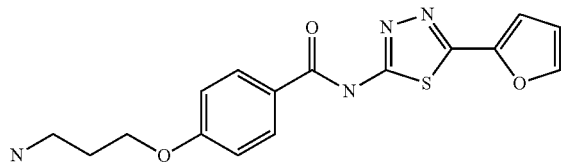 [SMILES: NCCCOc1ccc(C(=O)Nc2nnc(-c3ccco3)s2)cc1]

4-[(1-Amino-3-propyl)oxy]benzoic acid N-[5-(2-furyl)-1,3,4-thiadiazol-2-yl] amide (L20)

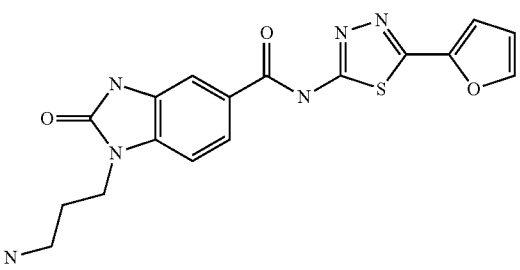

1-(3-Amino-1-propyl)-2-oxo-2,3-dihydrobenzimidazole-5-carboxylic acid N-[5-(2-furyl)-1,3,4-thiadiazol-2-yl] amide (L24)

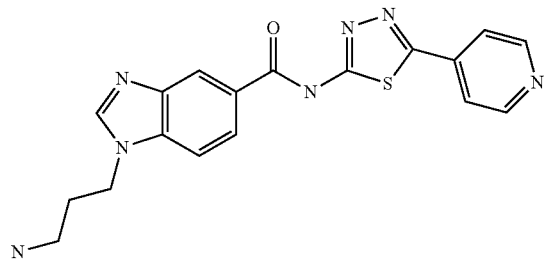 [SMILES: NCCCn1cnc2cc(C(=O)Nc3nnc(-c4ccncc4)s3)ccc21]

1-(3-Amino-1-propyl)benzimidazole-5-carboxylic acid N-[5-(4-pyridyl)-1,3,4-thiadiazol-2-yl]amide (L21)

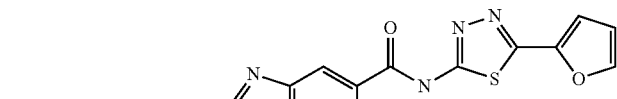

1-(8-Amino-3,5-dioxa-1-octyl)benzimidazole-5-carboxylic acid N-[5-(2-furyl)-1,3,4-thiadiazol-2-yl] amide (L25)

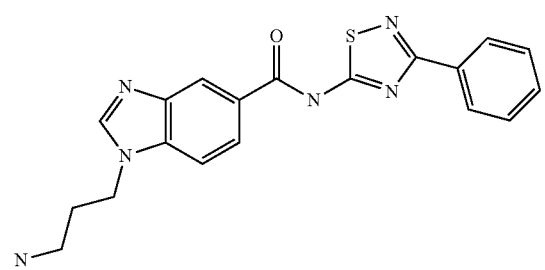 [SMILES: NCCCn1cnc2cc(C(=O)Nc3nc(-c4ccccc4)ns3)ccc21]

1-(3-Amino-1-propyl)benzimidazole-5-carboxylic acid N-(3-phenyl-1,2,4-thiadiazol-5-yl) amide (L22)

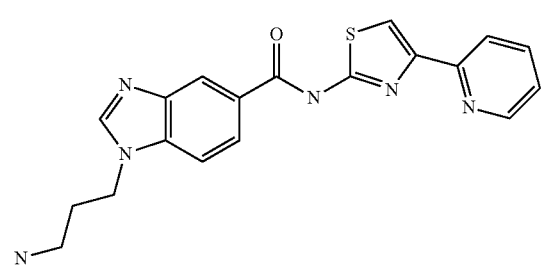 [SMILES: NCCCn1cnc2cc(C(=O)Nc3nc(-c4ccccn4)cs3)ccc21]

1-(3-Amino-1-propyl)benzimidazole-5-carboxylic acid N-[4-(2-pyridyl)thiazol-2-yl] amide (L23)

1-(8-Amino-3,5-dioxa-1-octyl)benzimidazole-5-carboxylic acid N-(5-methyl-1,3,4-thiadiazol-2-yl) amide (L26)

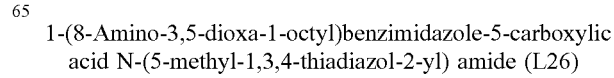

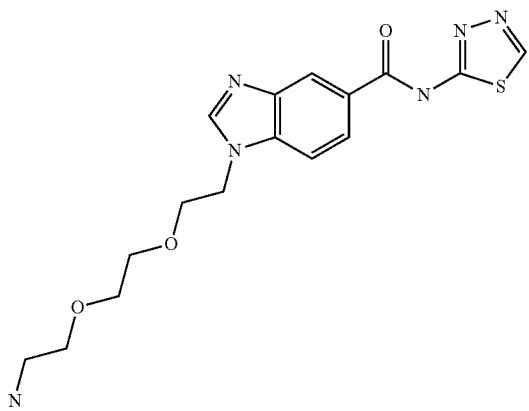 [SMILES: NCCOCCOCCn1cnc2cc(C(=O)Nc3nncs3)ccc21]

1-(8-Amino-3,5-dioxa-1-octyl)benzimidazole-5-carboxylic acid N-(1,3,4-thiadiazol-2-yl) amide (L27)

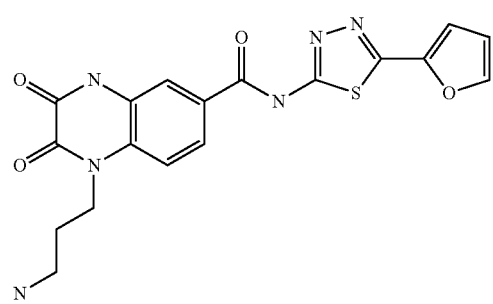 [SMILES: NCCCn1c(=O)c(=O)[nH]c2cc(C(=O)Nc3nnc(-c4ccco4)s3)ccc21]

1-(3-Amino-1-propyl)-2,3-dioxo-1,2,3,4-tetrahydroquinoxaline-6-carboxylic acid N-[5-(2-furyl)-1,3,4-thiadiazol-2-yl]amide (L28)

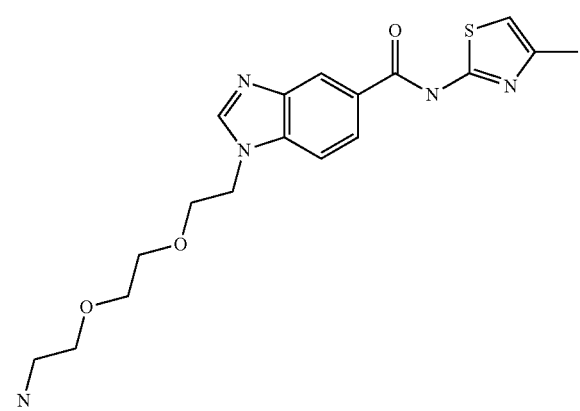 [SMILES: Cc1csc(NC(=O)c2ccc3c(c2)ncn3CCOCCOCCN)n1]

1-(8-Amino-3,5-dioxa-1-octyl)benzimidazole-5-carboxylic acid N-(4-methylthiazol-2-yl) amide (L29)

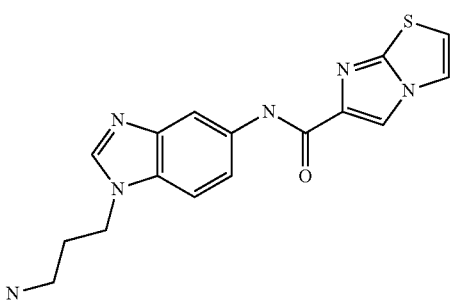 [SMILES: NCCCn1cnc2cc(NC(=O)c3cn4ccsc4n3)ccc21]

1-(3-Amino-1-propyl)-5-[(imidazo-[2,1-b]thiazol-6-yl)carboxamido]benzimidazole (L30)

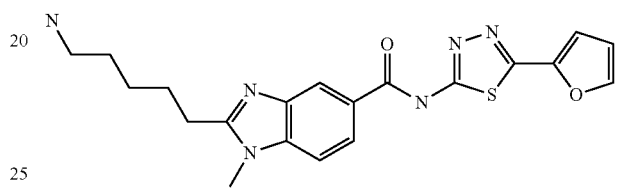

2-(5-Amino-1-pentyl)-1-methylbenzimidazole-5-carboxylic acid N-[5-(2-furyl)-1,3,4-thiadiazol-2-yl]amide (L31)

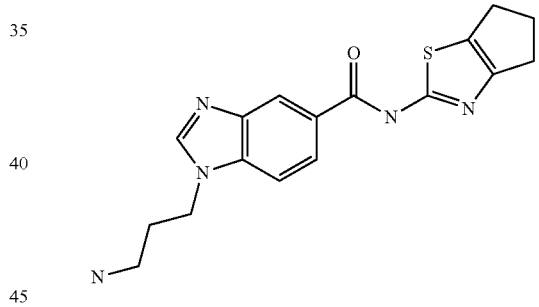

1-(3-Amino-1-propyl)benzimidazole-5-carboxylic acid N-(5,6-dihydro-(4H)-cyclopentathiazol-2-yl) amide (L32)

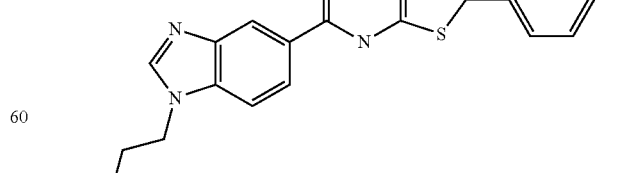

1-(3-Amino-1-propyl)benzimidazole-5-carboxylic acid N-(2-phenyl-1,3,4-thiadiazol-5-yl) amide (L33)

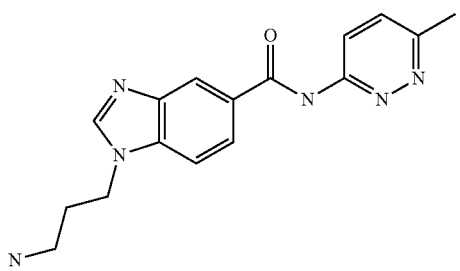 [SMILES: Cc1ccc(NC(=O)c2ccc3c(c2)ncn3CCCN)nn1]

1-(3-Amino-1-propyl)benzimidazole-5-carboxylic acid N-(6-methylpyridazin-3-yl) amide (L34)

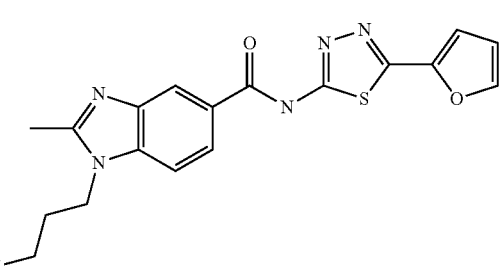

1-(3-Amino-1-propyl)-2-methylbenzimidazole-5-carboxylic acid N-[5-(2-furyl)-1,3,4-thiadiazol-2-yl] amide (L39)

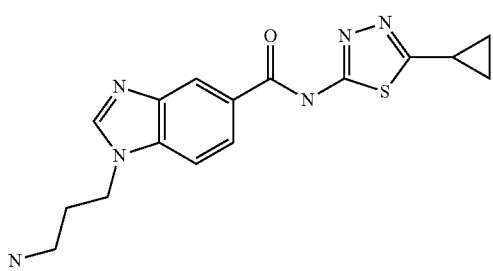 [SMILES: NCCCn1cnc2cc(C(=O)Nc3nnc(C4CC4)s3)ccc21]

1-(3-Amino-1-propyl)benzimidazole-5-carboxylic acid N-(2-cyclopropyl-1,3,4-thiadiazol-5-yl) amide (L35)

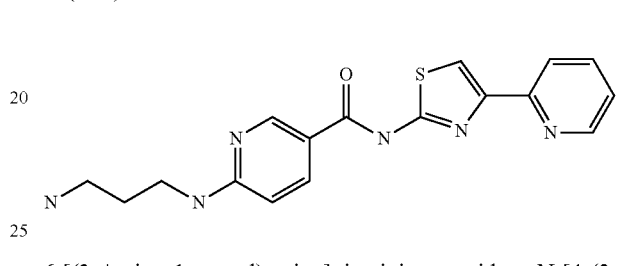

6-[(3-Amino-1-propyl)amino]nicotinic acid N-[4-(2-pyridyl)thiazol-2-yl] amide (L40)

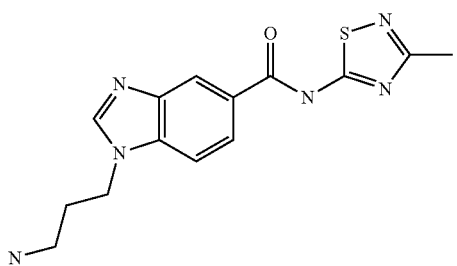 [SMILES: Cc1nsc(NC(=O)c2ccc3c(c2)ncn3CCCN)n1]

1-(3-Amino-1-propyl)benzimidazole-5-carboxylic acid N-(3-methyl-1,2,4-thiadiazol-5-yl) amide (L36)

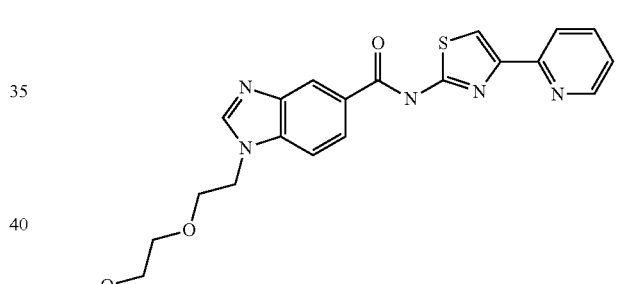

1-(8-Amino-3,5-dioxa-1-octyl)benzimidazole-5-carboxylic acid N-[4-(2-pyridyl)thiazol-2-yl]amide (L41)

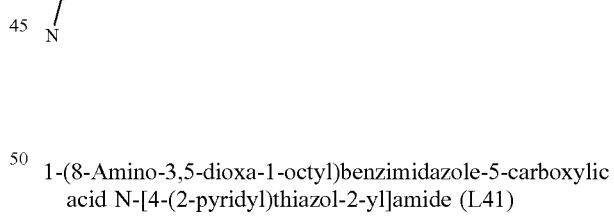

4-(5-Amino-3-oxa-1-pentyloxy)benzoic acid N-[5-(2-furyl)-1,3,4-thiadiazol-2-yl] amide (L37)

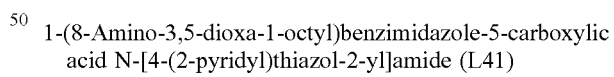

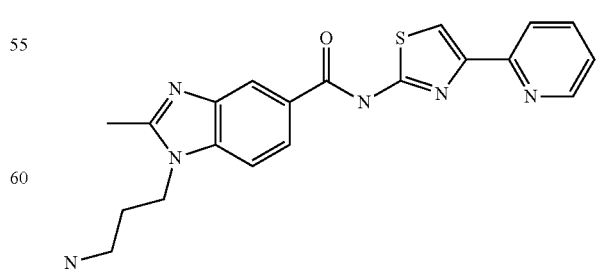

4-[(1-Amino-3-propyl)oxy]benzoic acid N-[4-(2-pyridyl)thiazol-2-yl] amide (L38)

1-(3-Amino-1-propyl)-2-methylbenzimidazole-5-carboxylic acid N-[4-(2-pyridyl)thiazol-2-yl] amide (L42)

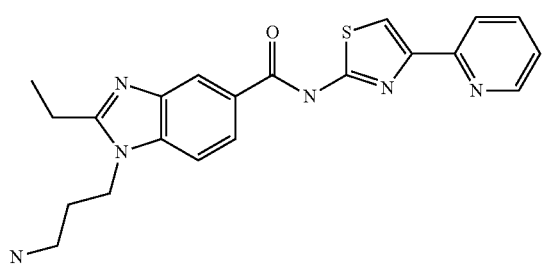 [SMILES: CCc1nc2cc(C(=O)Nc3nc(-c4ccccn4)cs3)ccc2n1CCCN]

1-(3-Amino-1-propyl)-2-ethylbenzimidazole-5-carboxylic acid N-[4-(2-pyridyl)thiazol-2-yl] amide (L43)

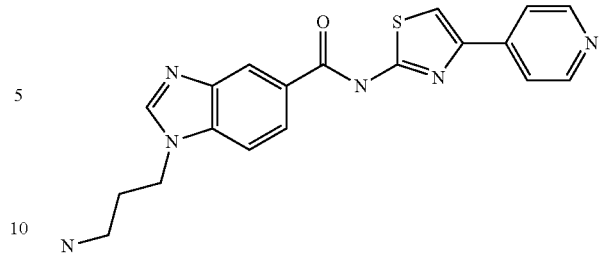

1-(3-Amino-1-propyl)benzimidazole-5-carboxylic acid N-[4-(4-pyridyl)thiazol-2-yl] amide (L47)

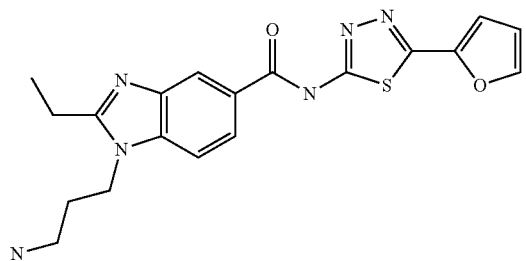 [SMILES: CCc1nc2cc(C(=O)Nc3nnc(-c4ccco4)s3)ccc2n1CCCN]

1-(3-Amino-1-propyl)-2-ethylbenzimidazole-5-carboxylic acid N-[5-(2-furyl)-1,3,4-thiadiazol-2-yl] amide (L44)

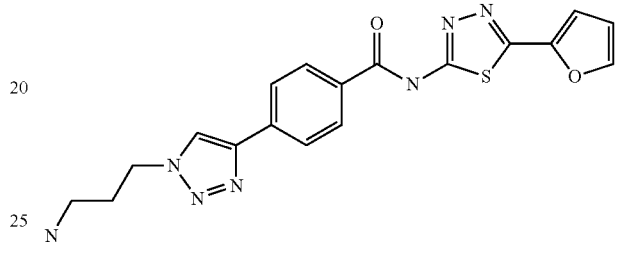

6-[1-(3-Amino-1-propyl)triazol-4-yl]benzoic acid N-[5-(2-furyl)-1,3,4-thiadiazol-2-yl]amide (L48)

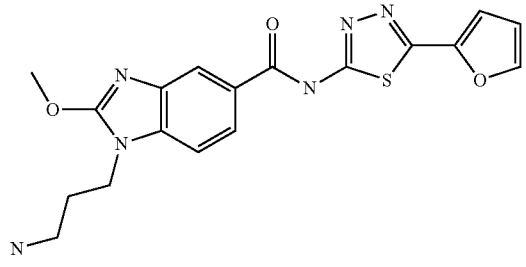

1-(3-Amino-1-propyl)-2-methoxybenzimidazole-5-carboxylic acid N-[5-(2-furyl)-1,3,4-thiadiazol-2-yl] amide (L45)

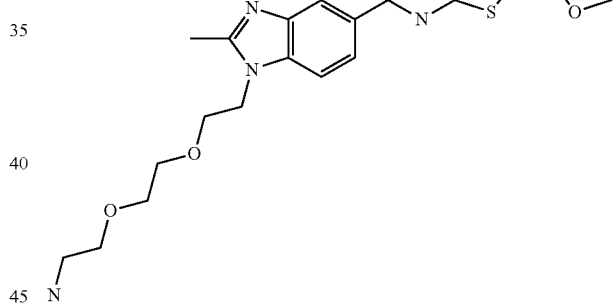

1-(8-Amino-3,5-dioxa-1-octyl)-2-methylbenzimidazole-5-carboxylic acid N-[5-(2-furyl)-1,3,4-thiadiazol-2-yl] amide (L49)

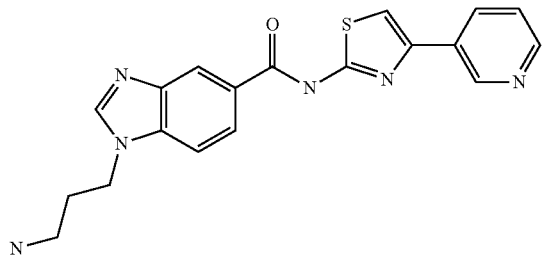 [SMILES: NCCCn1cnc2cc(C(=O)Nc3nc(-c4cccnc4)cs3)ccc21]

1-(3-Amino-1-propyl)benzimidazole-5-carboxylic acid N-[4-(3-pyridyl)thiazol-2-yl] amide (L46)

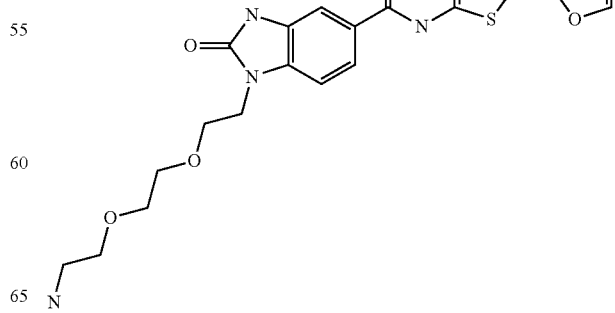

33
1-(8-Amino-3,5-dioxa-1-octyl)-2-oxo-2,3-dihydrobenzimidazole-5-carboxylic acid N-[5-(2-furyl)-1,3,4-thiadiazol-2-yl] amide (L50)
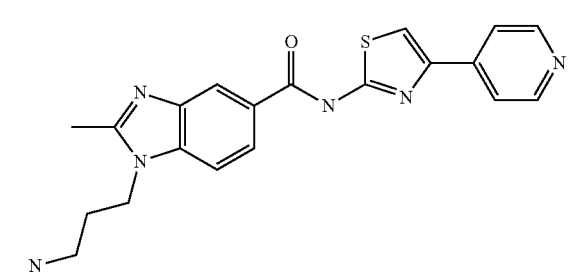 [SMILES: Cc1nc2cc(C(=O)Nc3nc(-c4ccncc4)cs3)ccc2n1CCCN]
1-(3-Amino-1-propyl)-2-methylbenzimidazole-5-carboxylic acid N-[4-(4-pyridyl)thiazol-2-yl] amide (L51)
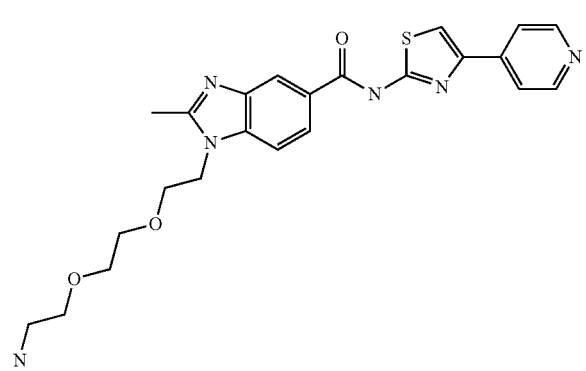 [SMILES: Cc1nc2cc(C(=O)Nc3nc(-c4ccncc4)cs3)ccc2n1CCOCCOCCN]
34
1-(8-Amino-3,5-dioxa-1-octyl)-2-methylbenzimidazole-5-carboxylic acid N-[4-(4-pyridyl)thiazol-2-yl] amide (L52)
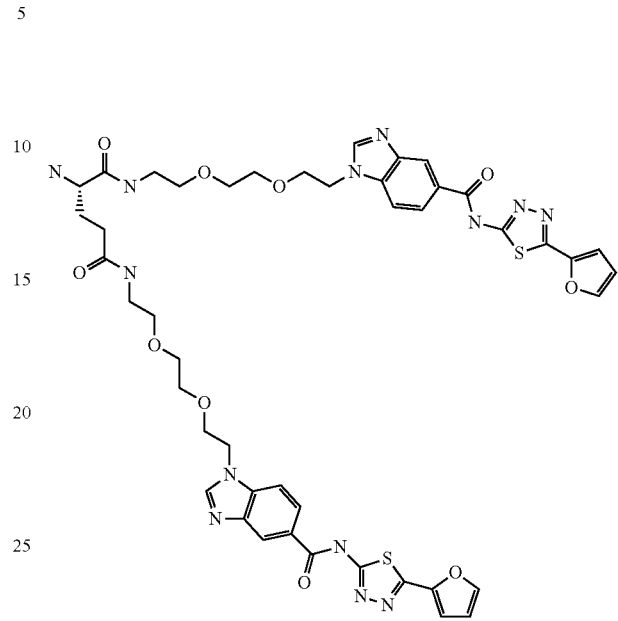
(S)-Glutamic acid N,N'-bis{8-{5-[5-(2-furyl)-1,3,4-thiadiazol-2-ylcarbamoyl]benzimidazol-1-yl}-3,5-dioxa-1-octyl} amide (L53)
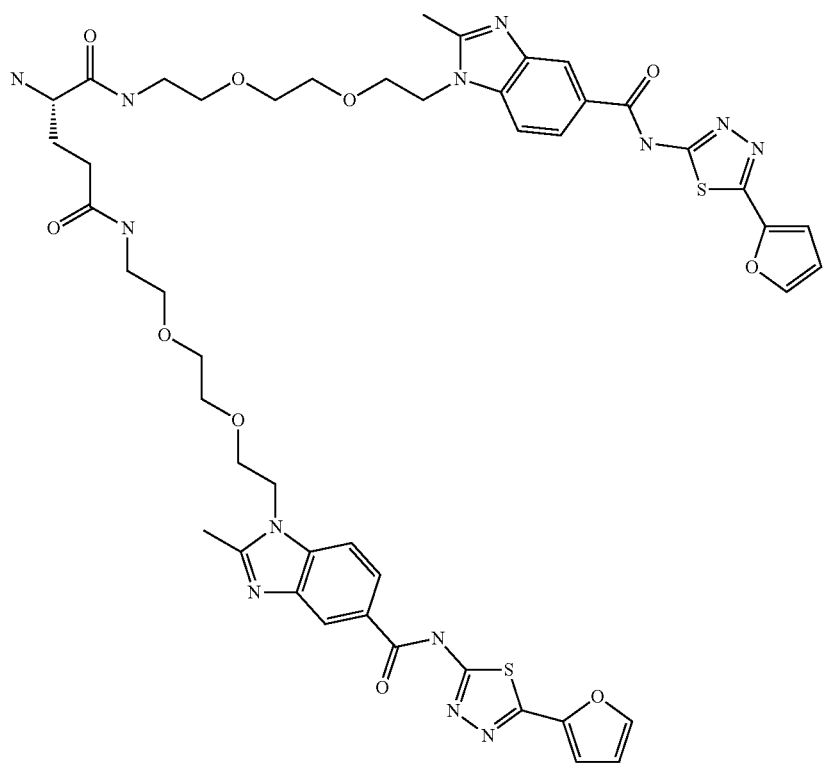 [SMILES: Cc1nc2cc(C(=O)Nc3nnc(-c4ccco4)s3)ccc2n1CCOCCOCCNC(=O)CC[C@H](N)C(=O)NCCOCCOCCn1c(C)nc2cc(C(=O)Nc3nnc(-c4ccco4)s3)ccc21]

(S)-Glutamic acid N,N'-bis{8-{5-[5-(2-furyl)-1,3,4-thiadiazol-2-ylcarbamoyl]-2-methylbenzimidazol-1-yl}-3,5-dioxa-1-octyl} amide (L54)

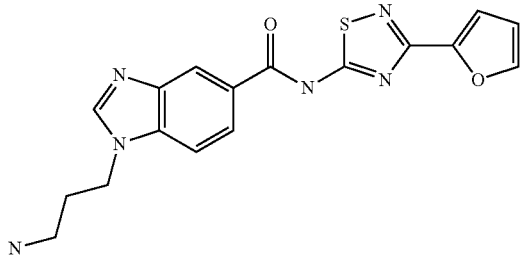 [SMILES: NCCCn1cnc2cc(C(=O)Nc3nc(-c4ccco4)ns3)ccc21]

1-(3-Amino-1-propyl)benzimidazole-5-carboxylic acid N-[3-(2-furyl)-1,2,4-thiadiazol-5-yl] amide (L55)

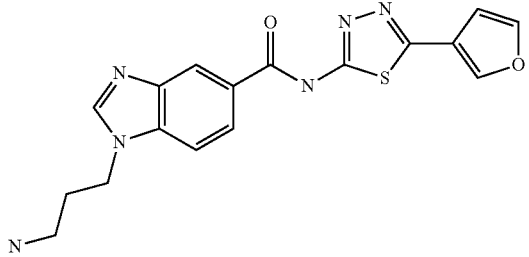

1-(3-Amino-1-propyl)benzimidazole-5-carboxylic acid N-[5-(3-furyl)-1,3,4-thiadiazol-2-yl] amide (L56)

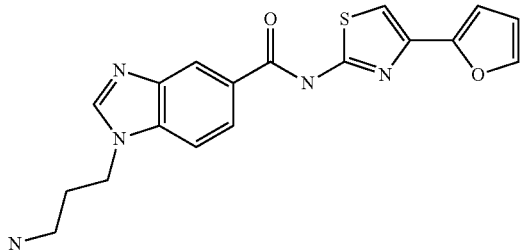 [SMILES: NCCCn1cnc2cc(C(=O)Nc3nc(-c4ccco4)cs3)ccc21]

1-(3-Amino-1-propyl)benzimidazole-5-carboxylic acid N-[4-(2-furyl)thiazol-2-yl] amide (L57)

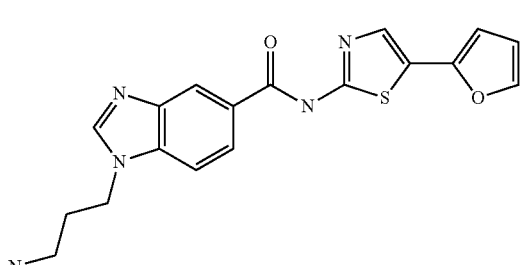

1-(3-Amino-1-propyl)benzimidazole-5-carboxylic acid N-[5-(2-furyl)thiazol-2-yl] amide (L58)

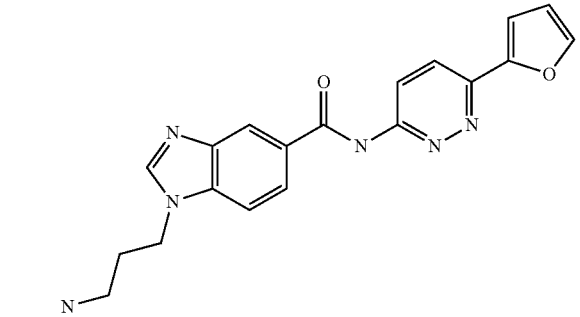 [SMILES: NCCCn1cnc2cc(C(=O)Nc3ccc(-c4ccco4)nn3)ccc21]

1-(3-Amino-1-propyl)benzimidazole-5-carboxylic acid N-[6-(2-furyl)pyridazin-3-yl] amide (L59)

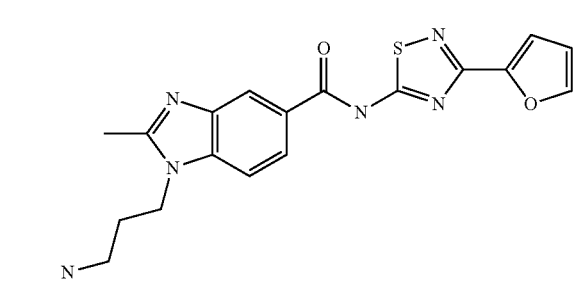 [SMILES: Cc1nc2cc(C(=O)Nc3nc(-c4ccco4)ns3)ccc2n1CCCN]

1-(3-Amino-1-propyl)-2-methylbenzimidazole-5-carboxylic acid N-[3-(2-furyl)-1,2,4-thiadiazol-5-yl] amide (L60)

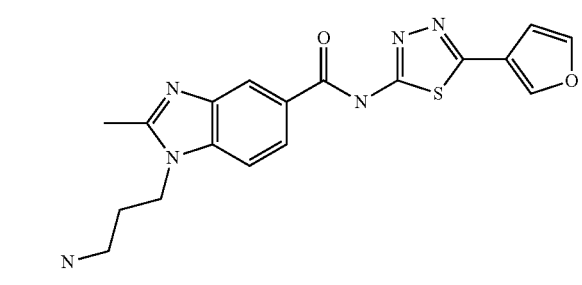 [SMILES: Cc1nc2cc(C(=O)Nc3nnc(-c4ccoc4)s3)ccc2n1CCCN]

1-(3-Amino-1-propyl)-2-methylbenzimidazole-5-carboxylic acid N-[5-(3-furyl)-1,3,4-thiadiazol-2-yl] amide (L61)

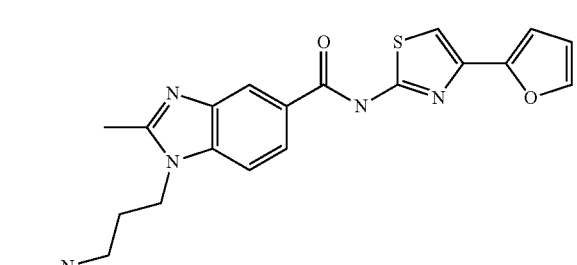

1-(3-Amino-1-propyl)-2-methylbenzimidazole-5-carboxylic acid N-[4-(2-furyl)thiazol-2-yl] amide (L62)

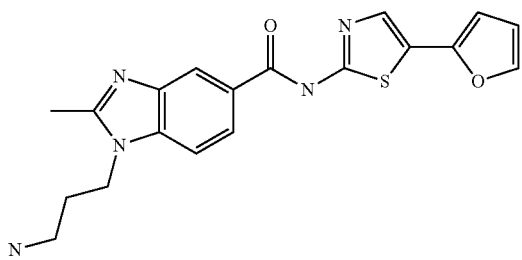 [SMILES: Cc1nc2cc(C(=O)Nc3ncc(-c4ccco4)s3)ccc2n1CCCN]

1-(3-Amino-1-propyl)-2-methylbenzimidazole-5-carboxylic acid N-[5-(2-furyl)thiazol-2-yl] amide (L63)

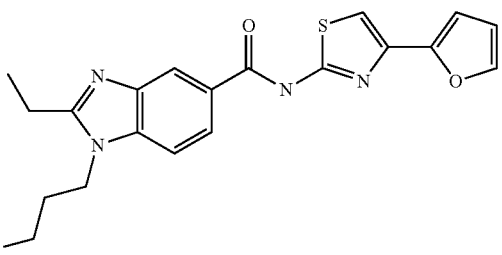

1-(3-Amino-1-propyl)-2-ethylbenzimidazole-5-carboxylic acid N-[4-(2-furyl)thiazol-2-yl] amide (L67)

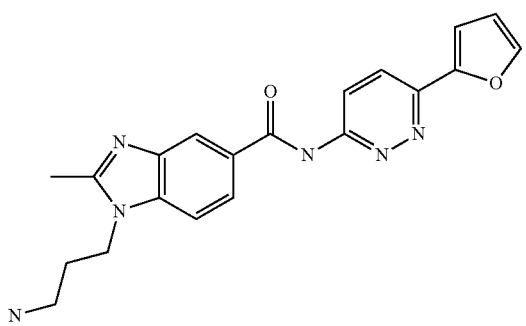 [SMILES: Cc1nc2cc(C(=O)Nc3ccc(-c4ccco4)nn3)ccc2n1CCCN]

1-(3-Amino-1-propyl)-2-methylbenzimidazole-5-carboxylic acid N-[6-(2-furyl)pyridazin-3-yl] amide (L64)

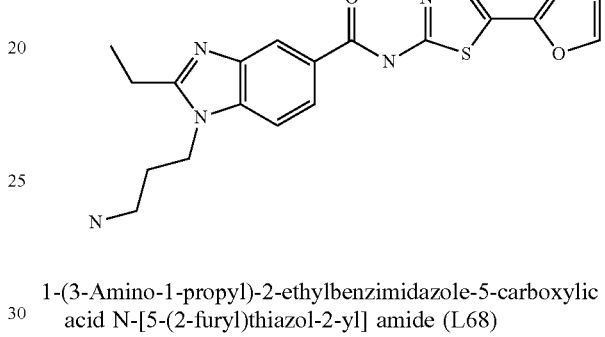

1-(3-Amino-1-propyl)-2-ethylbenzimidazole-5-carboxylic acid N-[5-(2-furyl)thiazol-2-yl] amide (L68)

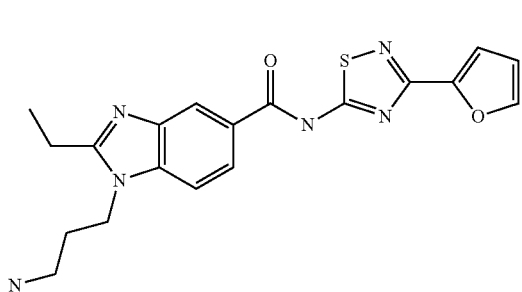 [SMILES: CCc1nc2cc(C(=O)Nc3nc(-c4ccco4)ns3)ccc2n1CCCN]

1-(3-Amino-1-propyl)-2-ethylbenzimidazole-5-carboxylic acid N-[3-(2-furyl)-1,2,4-thiadiazol-5-yl] amide (L65)

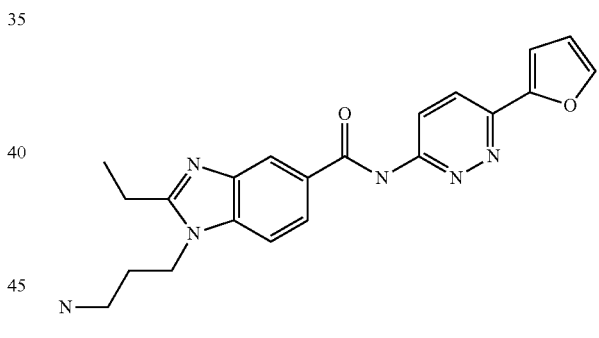

1-(3-Amino-1-propyl)-2-ethylbenzimidazole-5-carboxylic acid N-[6-(2-furyl)pyridazin-3-yl]amide (L69)

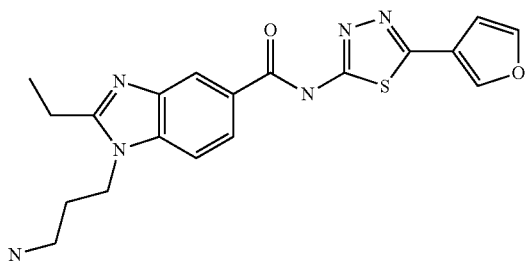 [SMILES: CCc1nc2cc(C(=O)Nc3nnc(-c4ccoc4)s3)ccc2n1CCCN]

1-(3-Amino-1-propyl)-2-ethylbenzimidazole-5-carboxylic acid N-[5-(3-furyl)-1,3,4-thiadiazol-2-yl] amide (L66)

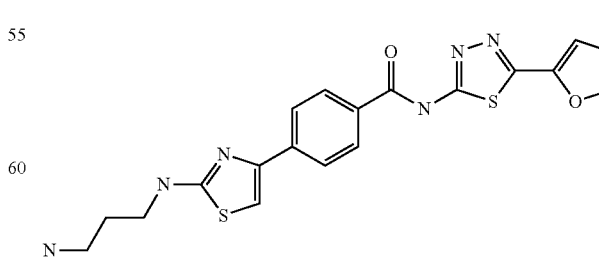

4-[2-(3-Amino-1-propylamino)thiazol-4-yl]benzoic acid N-[5-(2-furyl)-1,3,4-thiadiazol-2-yl]amide (L70)

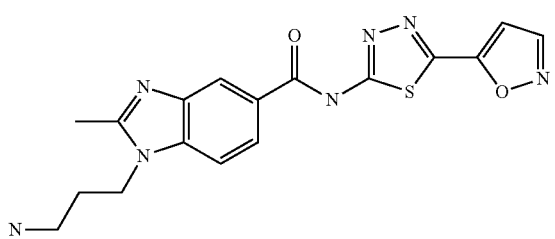 [SMILES: Cc1nc2cc(C(=O)Nc3nnc(-c4ccno4)s3)ccc2n1CCCN]

1-(3-Amino-1-propyl)-2-methylbenzimidazole-5-carboxylic acid N-[5-(5-isoxazolyl)-1,3,4-thiadiazol-2-yl] amide (L71)

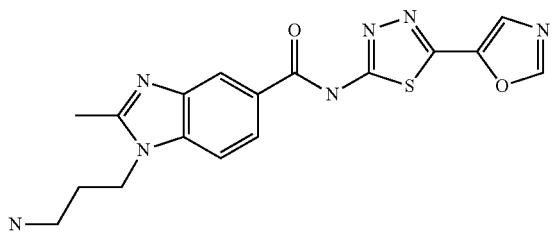 [SMILES: Cc1nc2cc(C(=O)Nc3nnc(-c4cnco4)s3)ccc2n1CCCN]

1-(3-Amino-1-propyl)-2-methylbenzimidazole-5-carboxylic acid N-[5-(5-oxazolyl)-1,3,4-thiadiazol-2-yl] amide (L72)

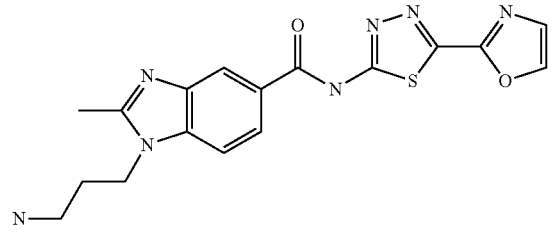 [SMILES: Cc1nc2cc(C(=O)Nc3nnc(-c4ncco4)s3)ccc2n1CCCN]

1-(3-Amino-1-propyl)-2-methylbenzimidazole-5-carboxylic acid N-[5-(2-oxazolyl)-1,3,4-thiadiazol-2-yl] amide (L73)

The synthesis of the ligands (II) can, for example, be carried out in a solution-phase synthesis by assembly of a carboxylic acid component and an amine component, ultimately forming the amide Am. The coupling can be accomplished by activation of the carboxylic acid component using an activating agent known to the person skilled in the art and by subsequent reaction of the activated carboxylic acid with the amine component, if necessary at elevated temperature which may be reached either by conventional heating of the reaction mixture or by microwave irradiation. In the course of this reaction, the amino group which, lateron, serves as the precursor group enabling the attachment of the ligands to the support material, needs to be protected by a suitable protecting group like tert-butoxycarbonyl. After successful coupling of the two components, the protecting group needs to be removed under suitable conditions. For the assembly of the individual components, additional solution phase synthesis steps may be applied which are known to the person skilled in the art. The deprotected ligands including the spacer group are purified by chromatographic methods also known to the person skilled in the art.

If a suitable solution-phase synthesis protocol should not be applicable to a particular ligand, the synthesis can alternatively be carried out on insoluble supports, also known as resins, e.g. polystyrene resins, preferably pre-loaded with a suitable spacer bearing a reactive group (functional group), e.g. a hydroxyl group, to which additional molecules may be attached by reactions known to the person skilled in the art. Finally, the ligands including the spacer group are released from the said insoluble support/resin by a suitable cleavage protocol known to the person skilled in the art and purified by chromatographic methods also known to the person skilled in the art.

The term "antibody" means an immunoglobulin, including both natural and wholly or partially synthetically produced and furthermore comprising all fragments and derivatives thereof which maintain specific binding ability. Typical fragments are Fc, Fab, heavy chain, and light chain. The term also comprises any polypeptide having a binding domain which is homologous or largely homologous, such as at least 95% identical when comparing the amino acid sequence, to an immunoglobulin binding domain. These polypeptides may be derived from natural sources, or partly or wholly synthetically produced. An antibody may be monoclonal or polyclonal and may be of human or non-human origin or a chimeric protein where the human Fc part is fused to murine Fab fragments (therapeutic antibodies with ending . . . ximab, e.g. Rituximab) or to Fab fragments comprising human and murine sequences (therapeutic antibodies with the ending . . . zumab, e.g. Bevacizumab) or linked to different Fab fragments (bispecific antibodies). The antibody may be a member of any immunoglobulin class, preferentially IgG, in case of human antibodies more preferentially $IgG_1$, $IgG_2$, $IgG_3$ and $IgG_4$.

In the most preferred embodiment of the present invention, the antibody comprises an Fc fragment or domain, as it is supposed that the ligands according to the present invention bind to an antibody's Fc part. Accordingly, an antibody of the present invention most preferably is an antibody containing an Fc fragment or domain of an immunoglobulin class, preferably IgG, more preferably of human IgG or of polyclonal or monoclonal IgG of human origin, in particular of $IgG_1$, $IgG_2$, $IgG_3$ and $IgG_4$.

The term "Fc fusion protein" refers to any combination of an Fc fragment with one or more proteins or protein domains. Examples of Fc fusion proteins include, but are not limited to, chimers of the human $IgG_1$ Fc domain with soluble receptor domains (therapeutic proteins with the ending . . . cept) such as Etanercept (human $IgG_1$ Fc combined with two tumor necrosis factor receptor domains) or Rilonacept (human $IgG_1$ fused with interleukin-1-receptor domain). The Fc fusion protein may be produced by any means. For instance, the Fc fusion protein may be enzymatically or chemically produced by coupling the Fc fragment to the appropriate protein or protein domain or it may be recombinantly produced from a gene encoding the Fc and the protein/protein domain sequence. Alternatively, the Fc fusion protein may be wholly or partially synthetically produced. The Fc fusion protein may also optionally be a multimolecular complex. A functional Fc fusion protein will typically comprise at least about 50 amino acids and more typically will comprise at least about 200 amino acids.

The present invention is drawn to the affinity purification, preferably by affinity chromatography, of antibodies or Fc fusion proteins from complex mixtures e.g. fermentation supernatants or plasma of human or animal origin, making use of the affinity ligands of formula (I) and preferred embodiments thereof, as disclosed elsewhere in the specification.

Accordingly, in a preferred embodiment, the present invention comprises a method for purifying a protein, preferably an immunoglobulin or Fc fusion protein, by affinity purification, preferably affinity chromatography. The affinity ligands according to the present invention bind to the Fc region of an antibody.

Bevacizumab (AVASTIN®, Genentech/Roche) is a humanized monoclonal antibody. It stops tumor growth by preventing the formation of new blood vessels by targeting and inhibiting the function of the protein vascular endothelial growth factor-A (VEGF-A) that stimulates new blood vessel formation (angiogenesis).

Tocilizumab (RoActemra®, Genentech/Roche) is a humanized monoclonal antibody. It is directed against the Interleukin-6 receptor and blocks the action of the proinflammatory cytokine Interleukin-6. It is approved for the treatment of rheumatoid arthritis.

Palivizumab (Synagis®, Abbott) is a humanized monoclonal antibody directed against the A-epitope of the respiratory syncytial virus (RSV) F-protein. It is used in the prevention of RSV infections.

Cetuximab (Erbitux®, Merck Serono) is a chimeric monoclonal antibody directed against the epidermal growth factor receptor. It is indicated for the treatment of colorectal cancer and squamous cell carcinoma of the head and neck Polyclonal human IgGs are investigated to demonstrate the universal applicability of the described ligands for the affinity purification of immunoglobulins via the Fc part.

When practicing the invention, the ligands according to the general formula (I) are attached to a support material of an appropriate support material, resulting in a ligand-substituted matrix, typically a matrix for affinity purification, preferably affinity chromatography (also referred to as affinity matrix in the context of the present invention) for protein separation. The ligands of the general formula are attached to the support material via L, optionally including a spacer -Sp-.

Accordingly, the present invention includes a ligand-substituted matrix (an affinity matrix) for protein separation, comprising a support material and at least one ligand as specified in the specification beforehand, wherein the ligand is attached thereto via L.

The matrix—which may be denoted M—may comprise or consist of any appropriate support material which is known to the person skilled in the art. The material may be soluble or insoluble, particulate or non-particulate, or of a monolithic structure, including fibers and membranes, porous or non-porous. It provides a convenient means of separating ligands of the invention from solutes in a contacting solution. Examples of support materials include carbohydrate and crosslinked carbohydrate matrices such as agarose, SEPHAROSE, SEPHADEX, cellulose, dextran, starch, alginate or carrageenan; synthetic polymer matrices such as polystyrene, styrene-divinylbenzene copolymers, polyacrylates, PEG polyacrylate copolymers, polymethacrylates, (e.g. poly(hydroxyethylmethacrylate), polyvinyl alcohol, polyamides or perfluorocarbons; inorganic matrices such as glass, silica or metal oxides; and composite materials.

The affinity matrix is prepared by providing a matrix of an appropriate support material and attaching a ligand of formula (I) (including formula (Ia), (Ib and (Ic) and/or formula (II), and/or having the structural element of formula (III) thereto. Methods for attaching the ligand (I) to the support material are known to the person skilled in the art.

The present application thus includes the use, of a ligand of formula (I) (including formula (Ia), (Ib and (Ic) and/or formula (II,) and/or having the structural element of formula (III), and wherein the variables wherein L, Sp, SpP, Am, $Ar^1$ $Ar^2$, $R^1$ and/or v have the meanings as defined in connection with formulae (I), (Ia), (Ib) (Ic), (II), and/or III), and/or defined in the present specification, in particular in connection with preferred embodiments, for the preparation/synthesis of a ligand-substituted matrix as preferably defined in formulae (I), (Ia), (Ib) (Ic), (II), more preferably formula (II).

The present invention also relates to a method for affinity purification, preferably affinity chromatography, of a protein wherein a protein to be purified is contacted with the ligand-substituted matrix as described before.

The term "affinity purification" (which is used interchangeably with the term "affinity separation") refers to any separation technique involving molecular recognition of a protein by a ligand of formula (I). The ligand may be immobilized on a solid support material facilitating separation of the ligand-antibody complex later on. Separation techniques may include, but are not limited to, affinity chromatography on packed columns, monolithic structures or membranes. The term further includes adsorption in batch-mode or affinity precipitation.

Independently of the flavor, purification techniques are composed by an initial recognition phase where ligand is contacted with antibody in crude. In a second phase, either impurities are separated from the ligand-antibody complex (e.g. column chromatography) or ligand-antibody complex is separated from impurities (e.g. affinity precipitation). In a third step, the antibody is released from the ligand-antibody complex by alteration of chemical and/or physical conditions like change in pH, ionic strength and/or addition of modifiers like organic solvents, detergents or chaotropes.

The invention will now be illustrated by the following examples, which shall not be construed to limit the invention.

Documents cited in the specification:
1. A. Cecilia, A. Roque, C. R. Lowe, M. A. Taipa: Antibodies and Genetically Engineered Related Molecules: Production and Purification, Biotechnol. Prog. 2004, 20, 639-654
2. K. L. Carson: Flexibility—the guiding principle for antibody manufacturing, Nature Biotechnology, 2005, 23, 1054-1058; S. Hober, K. Nord, M. Linhult: Protein A chromatography for antibody purification, J. Chromatogr. B. 2007, 848, 40-47
3. T. Arakawa, Y. Kita, H. Sato, D. Ejima, Protein Expression and Purification. 2009, 63, 158-163
4. S. Ghose, B. Hubbard, S. M. Cramer, Journal of Chromatography A, 2006, 1122, 144-152

EXAMPLES

Materials and Methods

If not otherwise stated, all chemicals and solvents were of analytical grade, with the exception of Example 1. Reagents used in Example 1 were of preparative to analytical grade depending on particulate requirements and availability.

96 and 384-well filter plates having hydrophilic membrane filters with 0.45 μm average pore size were purchased from Pall GmbH (Dreieich/Germany). Top frits made from polyethylene with 10 μm average pore size were provided by Porex (Bautzen/Germany). General purpose microtiterplates for collection of fractions and analytical assays were ordered from Greiner Bio One GmbH (Frickenhausen/Germany). Analytical assays were read out using a Fluostar Galaxy plate reader from BMG Labtech GmbH (Offenburg/Germany).

Column chromatography with antibody and purification of antibody fragments was conducted on a Waters HPLC system (Waters GmbH, Eschborn/Germany). Omnifit column housings (Diba Industries Ltd, Cambridge/United Kingdom) were used for packing of columns. NHS-activated SEPHAROSE 4 FF, rProtein A SEPHAROSE FF and Superdex 70 chromatography media were bought from GE Healthcare (Uppsala/Sweden). MABSORBENT A2P HF was purchased from Prometic Life Sciences (Cambridge/United Kingdom) and MEP HYPERCEL from Pall Corporation (Port Washington N.Y., USA).

Analytical chromatography of ligands was conducted on a Shimadzu HPLC system (Shimadzu Deutschland GmbH, Duisburg/Germany) including a diode array detector and single-quad mass spectrometer. The monolithic C18 reversed phase column was purchased from Merck KGaA (Darmstadt/Germany). Solvents used in analyses were of mass spectrometry grade.

Antibodies used in the present invention were Bevacizumab (AVASTIN, F. Hoffmann-La Roche, Switzerland), Tocilizumab (RoActemra, F. Hoffmann-La Roche, Switzerland), Palivizumab (Synagis, Abbott, USA), Cetuximab (Erbitux, Merck Serono GmbH, Germany), and poly-IgG from human serum (Sigma-Aldrich, USA).

Flowthrough from protein A chromatography (referred to as host cell proteins) was derived from the supernatant of antibody-producing CHO cell culture in serum-free medium. Coomassie brilliant blue dye reagent for Bradford assay was purchased from Thermo Scientific (Bonn/Germany).

Example 1: Synthesis of Ligands

General Procedure A: Coupling of Aromatic Carboxylic Acids to Aromatic Amines Under Microwave Irradiation; Deprotection.

The (tert-butoxycarbonylamino)alkyl or (tert-butoxycarbonylamino)alkoxy-alkoxy-alkyl substituted aromatic carboxylic acid (0.1 to 0.5 mmol, typically 0.1 mmol) and HATU (1 equivalent relative to the carboxylic acid) were dissolved in acetonitrile (1 to 5 mL, typically 1 mL) and DIPEA (2 equivalent relative to the carboxylic acid). After agitating for 5 to 10 min (typically 10 min), the solution was added to the aromatic amine (1 equivalent relative to the carboxylic acid) in a microwave vial. After flushing with argon, the vial was sealed and the mixture was heated to 100 to 120° C. (typically 120° C.) for 60 to 90 min (typically 90 min) under microwave irradiation. A small sample was taken out and subjected to HPLC-MS analysis. If the reaction was complete (i.e. no active ester visible in HPLC-MS), the mixture was worked up. If both active ester and aromatic amine were detectable, heating was continued for up to 12 h. If unreacted active ester, but no residual aromatic amine was detectable, excess aromatic amine (typically 0.5 equivalents relative to the carboxylic acid) in a minute amount of acetonitrile (typically 0.5 mL) was added and heating was continued until complete consumption of the active ester.

In most cases, the product precipitated almost quantitatively upon cooling of the reaction mixture to room temperature. In these cases, the solid was separated and washed with ethyl acetate (once to twice, typically once) or methanol (once), followed by TBME (once), and dried cautiously with a stream of nitrogen.

If the product did not precipitate or it did so only partially, the solvent was removed with a stream of nitrogen. The residue was treated with aqueous citric acid (5%), followed by multiple extractions with ethyl acetate. The combined organic layers were washed with water and evaporated to dryness.

In all cases, deprotection of the tert-butoxycarbonyl protecting group was accomplished by treatment of the residue with dichloromethane (typically 2 mL) and trifluoroacetic acid (typically 1 mL), typically for 1 h, followed by thorough evaporation of the solvents. The crude products were purified by preparative reverse-phase HPLC-MS (acetonitrile in water gradient elution) or by flash column chromatography (amino functionalized stationary phase, methanol in dichloromethane gradient elution).

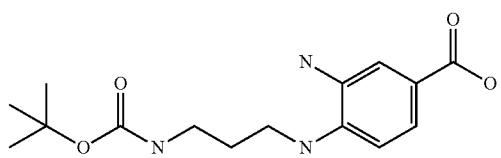 [SMILES: CC(C)(C)OC(=O)NCCCNc1ccc(C(=O)O)cc1N]

Synthesis of 3-amino-4-[(3-tert-butyloxycarbonylamino-1-propyl)amino]benzoic acid N-tert-butoxycarbonyl-1,3-diaminopropane (5 mmol) and DIPEA (10 mmol) in dioxane (5 mL) were added to 4-fluoro-3-nitrobenzoic acid (5 mmol) in dioxane (5 mL). The mixture was heated to reflux for 90 min, subsequently, the solvent was removed in vacuo and the residue was treated with aqueous citric acid (5%) and extracted twice with ethyl acetate. The combined organic layers were washed with water, evaporated to dryness, co-evaporated with ethyl acetate, and the residue was dried in high vacuum.

To the residue was added palladium on activated carbon (5%, moistened with 50% water; Degussa Type E 101 NO/W; 50 mg) and methanol (20 mL) under argon. Triethylsilane (4 mL) was added dropwise over 10 min. Subsequently, the mixture was filtered through celite, the filtrate was evaporated to dryness and the residue was dried in high vacuum and used without further purification. The reaction was repeated successfully several times.

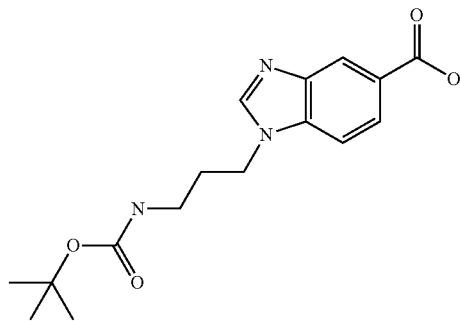 [SMILES: CC(C)(C)OC(=O)NCCCn1cnc2cc(C(=O)O)ccc21]

Synthesis of 1-(3-tert-butyloxycarbonylamino-1-propyl)benzimidazole-5-carboxylic acid Trimethylorthoformate (10 mL) was added to the complete amount of 3-amino-4-[(3-tert-butyloxycarbonylamino-1-propyl)amino]benzoic acid obtained by the procedure described before. The mixture was heated to reflux for 35 min, whereupon the solvent was removed and the residue was dried in high vacuum and purified by flash column chromatography (SiO$_2$ stationary phase, methanol in dichloromethane gradient elution), furnishing 1-(3-tert-butyloxycarbonylamino-1-propyl)benzimidazole-5-carboxylic acid as a brownish solid.

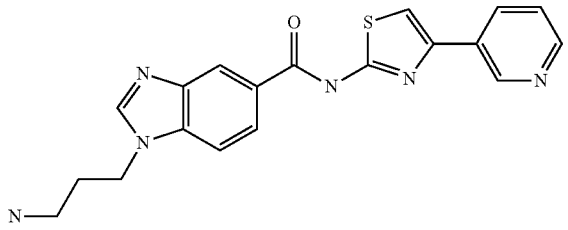 [SMILES: NCCCn1cnc2cc(C(=O)Nc3nc(-c4cccnc4)cs3)ccc21]

Synthesis of 1-(3-amino-1-propyl)benzimidazole-5-carboxylic acid N-[4-(3-pyridyl)thiazol-2-yl] amide (L46)

Prepared from 1-(3-tert-butyloxycarbonylamino-1-propyl)benzimidazole-5-carboxylic acid and 2-amino-4-(3-pyridyl)thiazole following General Procedure A. ESI-MS: 379 (M+1).

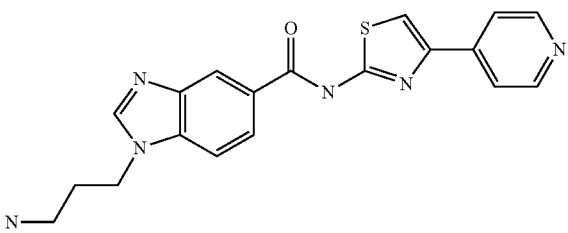 [SMILES: NCCCn1cnc2cc(C(=O)Nc3nc(-c4ccncc4)cs3)ccc21]

Synthesis of 1-(3-amino-1-propyl)benzimidazole-5-carboxylic acid N-[4-(4-pyridyl)thiazol-2-yl] amide (L47)

Prepared from 1-(3-tert-butyloxycarbonylamino-1-propyl)benzimidazole-5-carboxylic acid and 2-amino-4-(4-pyridyl)thiazole following General Procedure A. ESI-MS: 379 (M+1).

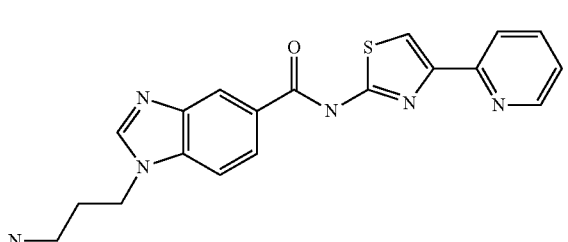

Synthesis of 1-(3-amino-1-propyl)benzimidazole-5-carboxylic acid N-[4-(2-pyridyl)thiazol-2-yl] amide (L23)

Prepared from 1-(3-tert-butyloxycarbonylamino-1-propyl)benzimidazole-5-carboxylic acid and 2-amino-4-(2-pyridyl)thiazole following General Procedure A. ESI-MS: 379 (M+1).

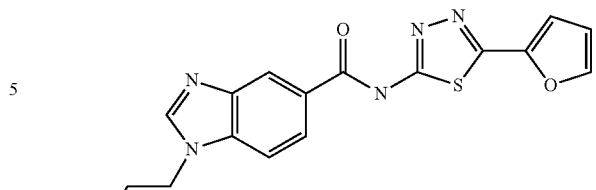

Synthesis of 1-(3-amino-1-propyl)benzimidazole-5-carboxylic acid N-[5-(2-furyl)-1,3,4-thiadiazol-2-yl] amide (L05)

Prepared from 1-(3-tert-butyloxycarbonylamino-1-propyl)benzimidazole-5-carboxylic acid and 2-amino-5-(2-furyl)-1,3,4-thiadiazole following General Procedure A. ESI-MS: 369 (M+1).

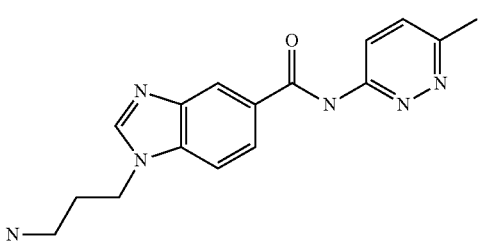 [SMILES: Cc1ccc(NC(=O)c2ccc3c(c2)ncn3CCCN)nn1]

Synthesis of 1-(3-amino-1-propyl)benzimidazole-5-carboxylic acid N-(6-methylpyridazin-3-yl) amide (L34)

Prepared from 1-(3-tert-butyloxycarbonylamino-1-propyl)benzimidazole-5-carboxylic acid and 3-amino-6-methylpyridazine following General Procedure A. ESI-MS: 311 (M+1).

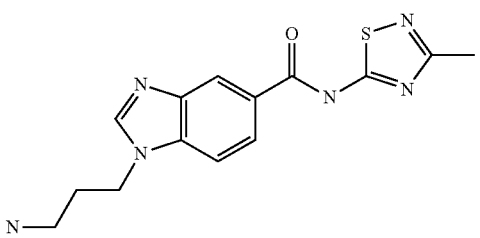 [SMILES: Cc1nsc(NC(=O)c2ccc3c(c2)ncn3CCCN)n1]

Synthesis of 1-(3-amino-1-propyl)benzimidazole-5-carboxylic acid N-(3-methyl-1,2,4-thiadiazol-5-yl) amide (L36)

Prepared from 1-(3-tert-butyloxycarbonylamino-1-propyl)benzimidazole-5-carboxylic acid and 5-amino-3-methyl-1,2,4-thiadiazole following General Procedure A. ESI-MS: 317 (M+1).

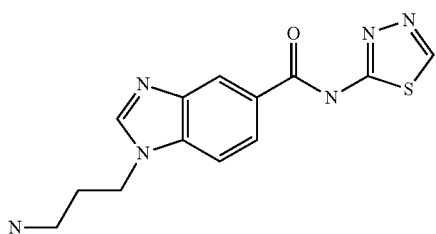 [SMILES: NCCCn1cnc2cc(C(=O)Nc3nncs3)ccc21]

Synthesis of 1-(3-amino-1-propyl)benzimidazole-5-carboxylic acid N-(1,3,4-thiadiazol-2-yl) amide (L13)

Prepared from 1-(3-tert-butyloxycarbonylamino-1-propyl)benzimidazole-5-carboxylic acid and 2-amino-1,3,4-thiadiazole following General Procedure A. ESI-MS: 303 (M+1).

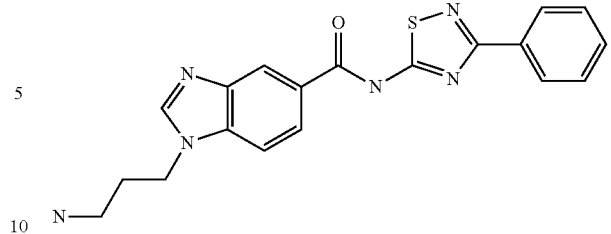

Synthesis of 1-(3-amino-1-propyl)benzimidazole-5-carboxylic acid N-(3-phenyl-1,2,4-thiadiazol-5-yl) amide (L22)

Prepared from 1-(3-tert-butyloxycarbonylamino-1-propyl)benzimidazole-5-carboxylic acid and 5-amino-3-phenyl-1,2,4-thiadiazole following General Procedure A. ESI-MS: 379 (M+1).

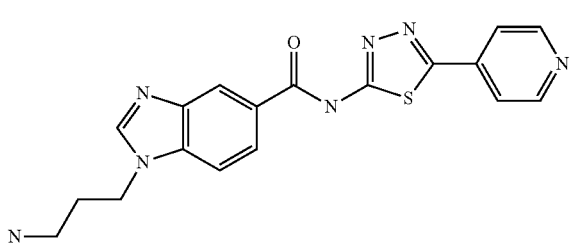 [SMILES: NCCCn1cnc2cc(C(=O)Nc3nnc(-c4ccncc4)s3)ccc21]

Synthesis of 1-(3-amino-1-propyl)benzimidazole-5-carboxylic acid N-[5-(4-pyridyl)-1,3,4-thiadiazol-2-yl] amide (L21)

Prepared from 1-(3-tert-butyloxycarbonylamino-1-propyl)benzimidazole-5-carboxylic acid and 2-amino-5-(4-pyridyl)-1,3,4-thiadiazole following General Procedure A. ESI-MS: 380 (M+1).

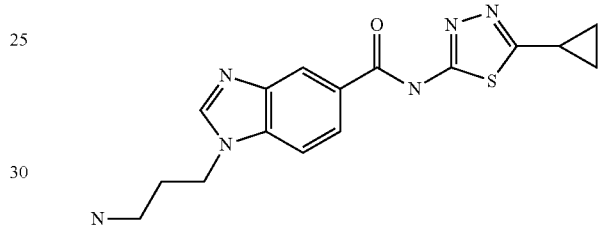

Synthesis of 1-(3-amino-1-propyl)benzimidazole-5-carboxylic acid N-(2-cyclopropyl-1,3,4-thiadiazol-5-yl) amide (L35)

Prepared from 1-(3-tert-butyloxycarbonylamino-1-propyl)benzimidazole-5-carboxylic acid and 2-amino-5-cyclopropyl-1,3,4-thiadiazole following General Procedure A. ESI-MS: 343 (M+1).

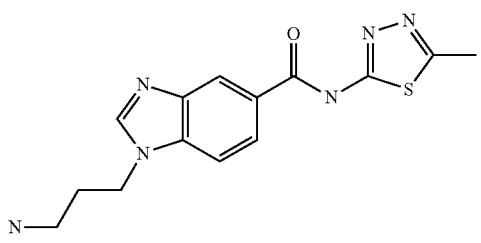 [SMILES: Cc1nnc(NC(=O)c2ccc3c(c2)ncn3CCCN)s1]

Synthesis of 1-(3-amino-1-propyl)benzimidazole-5-carboxylic acid N-(2-methyl-1,3,4-thiadiazol-5-yl) amide (L14)

Prepared from 1-(3-tert-butyloxycarbonylamino-1-propyl)benzimidazole-5-carboxylic acid and 2-amino-5-methyl-1,3,4-thiadiazole following General Procedure A. ESI-MS: 317 (M+1).

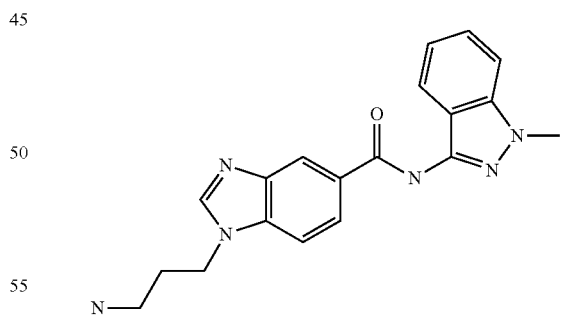

Synthesis of 1-(3-amino-1-propyl)benzimidazole-5-carboxylic acid N-(1-methyl-3-indazolyl) amide (L02)

Prepared from 1-(3-tert-butyloxycarbonylamino-1-propyl)benzimidazole-5-carboxylic acid and 3-amino-1-methylindazole following General Procedure A. ESI-MS: 349 (M+1).

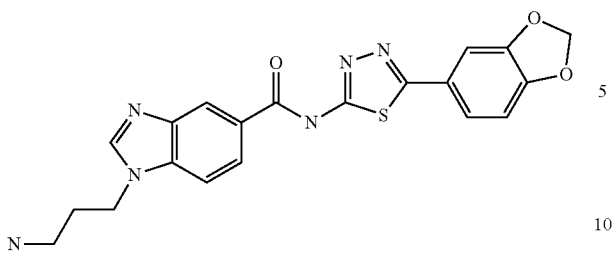

Synthesis of 1-(3-amino-1-propyl)benzimidazole-5-carboxylic acid N-[2-(3,4-methylenedioxyphenyl)-1,3,4-thiadiazol-5-yl] amide (L09)

Prepared from 1-(3-tert-butyloxycarbonylamino-1-propyl)benzimidazole-5-carboxylic acid and 2-amino-5-(3,4-methylenedioxyphenyl)-1,3,4-thiadiazole following General Procedure A. ESI-MS: 423 (M+1).

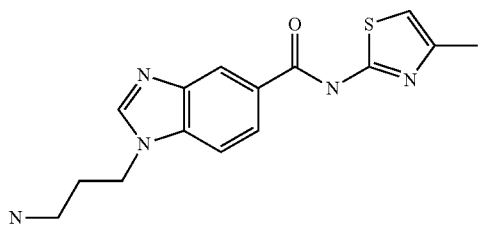

Synthesis of 1-(3-amino-1-propyl)benzimidazole-5-carboxylic acid N-(4-methylthiazol-2-yl) amide (L15)

Prepared from 1-(3-tert-butyloxycarbonylamino-1-propyl)benzimidazole-5-carboxylic acid and 2-amino-4-methylthiazole following General Procedure A. ESI-MS: 316 (M+1).

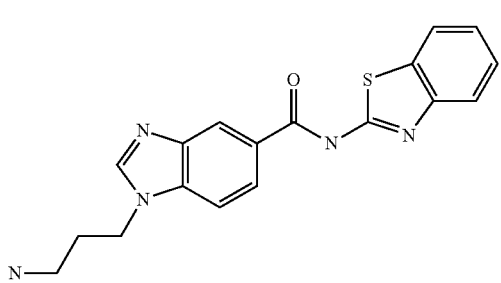 [SMILES: NCCCn1cnc2cc(C(=O)Nc3nc4ccccc4s3)ccc21]

Synthesis of 1-(3-amino-1-propyl)benzimidazole-5-carboxylic acid N-(benzothiazol-2-yl) amide (L10)

Prepared from 1-(3-tert-butyloxycarbonylamino-1-propyl)benzimidazole-5-carboxylic acid and 2-aminobenzothiazole following General Procedure A. ESI-MS: 352 (M+1).

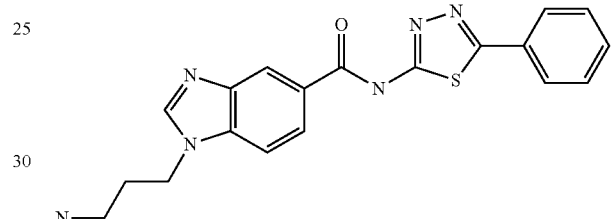

Synthesis of 1-(3-amino-1-propyl)benzimidazole-5-carboxylic acid N-(2-phenyl-1,3,4-thiadiazol-5-yl) amide (L33)

Prepared from 1-(3-tert-butyloxycarbonylamino-1-propyl)benzimidazole-5-carboxylic acid and 2-amino-5-phenyl-1,3,4-thiadiazole following General Procedure A. ESI-MS: 379 (M+1).

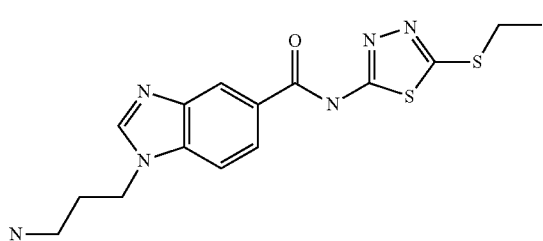 [SMILES: CCSc1nnc(NC(=O)c2ccc3c(c2)ncn3CCCN)s1]

Synthesis of 1-(3-amino-1-propyl)benzimidazole-5-carboxylic acid N-(2-ethylthio-1,3,4-thiadiazol-5-yl) amide (L12)

Prepared from 1-(3-tert-butyloxycarbonylamino-1-propyl)benzimidazole-5-carboxylic acid and 2-amino-5-ethylthio-1,3,4-thiadiazole following General Procedure A. ESI-MS: 363 (M+1).

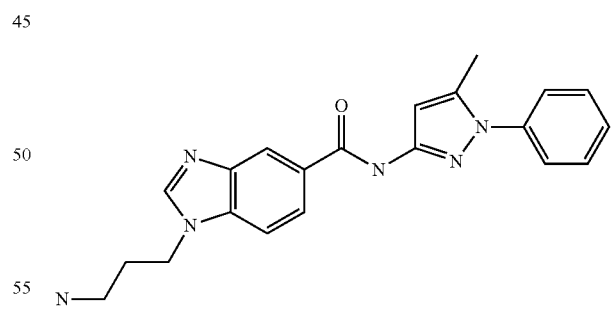

Synthesis of 1-(3-amino-1-propyl)benzimidazole-5-carboxylic acid N-(5-methyl-1-phenylpyrazol-3-yl) amide (L11)

Prepared from 1-(3-tert-butyloxycarbonylamino-1-propyl)benzimidazole-5-carboxylic acid and 3-amino-5-methyl-1-phenylpyrazole following General Procedure A. ESI-MS: 375 (M+1).

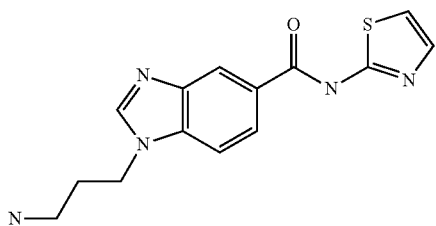 [SMILES: NCCCn1cnc2cc(C(=O)Nc3nccs3)ccc21]

Synthesis of 1-(3-amino-1-propyl)benzimidazole-5-carboxylic acid N-(thiazol-2-yl) amide (L16)

Prepared from 1-(3-tert-butyloxycarbonylamino-1-propyl)benzimidazole-5-carboxylic acid and 2-aminothiazole following General Procedure A. ESI-MS: 302 (M+1).

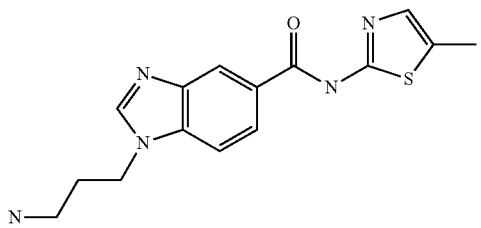 [SMILES: Cc1cnc(NC(=O)c2ccc3c(c2)ncn3CCCN)s1]

Synthesis of 1-(3-amino-1-propyl)benzimidazole-5-carboxylic acid N-(5-methylthiazol-2-yl) amide (L17)

Prepared from 1-(3-tert-butyloxycarbonylamino-1-propyl)benzimidazole-5-carboxylic acid and 2-amino-5-methylthiazole following General Procedure A. ESI-MS: 316 (M+1).

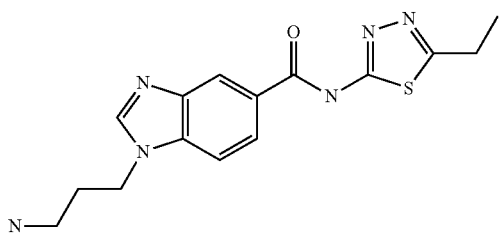 [SMILES: CCc1nnc(NC(=O)c2ccc3c(c2)ncn3CCCN)s1]

Synthesis of 1-(3-amino-1-propyl)benzimidazole-5-carboxylic acid N-(2-ethyl-1,3,4-thiadiazol-5-yl) amide (L07)

Prepared from 1-(3-tert-butyloxycarbonylamino-1-propyl)benzimidazole-5-carboxylic acid and 2-amino-5-ethyl-1,3,4-thiadiazole following General Procedure A. ESI-MS: 331 (M+1).

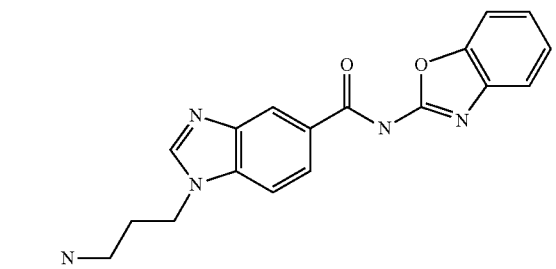 [SMILES: NCCCn1cnc2cc(C(=O)Nc3nc4ccccc4o3)ccc21]

Synthesis of 1-(3-amino-1-propyl)benzimidazole-5-carboxylic acid N-(benzoxazol-2-yl) amide (L08)

Prepared from 1-(3-tert-butyloxycarbonylamino-1-propyl)benzimidazole-5-carboxylic acid and 2-aminobenzoxazole following General Procedure A. ESI-MS: 336 (M+1).

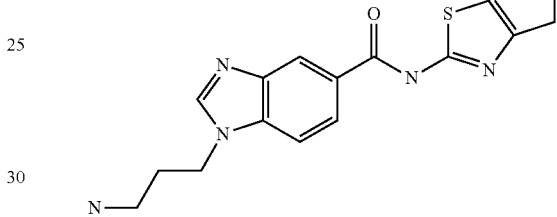

Synthesis of 1-(3-amino-1-propyl)benzimidazole-5-carboxylic acid N-(5,6-dihydro-(4H)-cyclopentathiazol-2-yl) amide (L32)

Prepared from 1-(3-tert-butyloxycarbonylamino-1-propyl)benzimidazole-5-carboxylic acid and 2-amino-5,6-dihydro-(4H)-cyclopentathiazole following General Procedure A. ESI-MS: 342 (M+1).

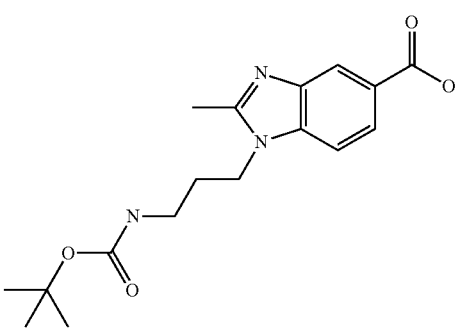 [SMILES: Cc1nc2cc(C(=O)O)ccc2n1CCCNC(=O)OC(C)(C)C]

Synthesis of 1-(3-tert-butyloxycarbonylamino-1-propyl)-2-methylbenzimidazole-5-carboxylic acid To 3-amino-4-[(3-tert-butyloxycarbonylamino-1-propyl)amino]benzoic acid (synthesis, see before; 0.5 mmol) in dioxane (2 mL) was added trimethylorthoacetate (2 mmol) in a glass vial. The vial was thoroughly closed and the mixture was heated to 100° C. for 1 h, whereupon the solvents were evaporated. The residue was purified by flash

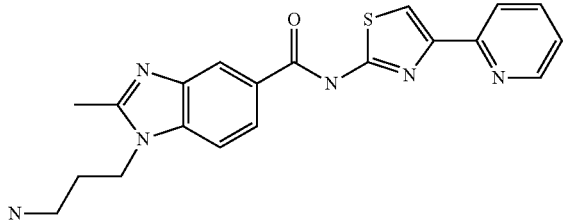 [SMILES: Cc1nc2cc(C(=O)Nc3nc(-c4ccccn4)cs3)ccc2n1CCCN]

Synthesis of 1-(3-amino-1-propyl)-2-methylbenzimidazole-5-carboxylic acid N-[4-(2-pyridyl)thiazol-2-yl] amide (L42)

Prepared from 1-(3-tert-butyloxycarbonylamino-1-propyl)-2-methylbenzimidazole-5-carboxylic acid and 2-amino-4-(2-pyridyl)thiazole following General Procedure A. ESI-MS: 393 (M+1).

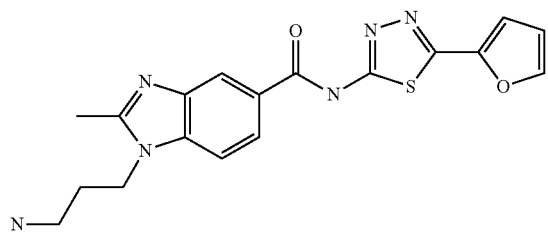 [SMILES: Cc1nc2cc(C(=O)Nc3nnc(-c4ccco4)s3)ccc2n1CCCN]

Synthesis of 1-(3-amino-1-propyl)-2-methylbenzimidazole-5-carboxylic acid N-[5-(2-furyl)-1,3,4-thiadiazol-2-yl] amide (L39)

Prepared from 1-(3-tert-butyloxycarbonylamino-1-propyl)-2-methylbenzimidazole-5-carboxylic acid and 2-amino-5-(2-furyl)-1,3,4-thiadiazole following General Procedure A. ESI-MS: 383 (M+1).

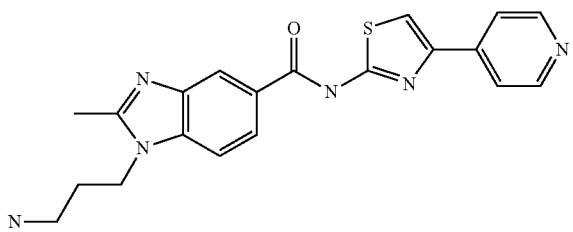 [SMILES: Cc1nc2cc(C(=O)Nc3nc(-c4ccncc4)cs3)ccc2n1CCCN]

Synthesis of 1-(3-amino-1-propyl)-2-methylbenzimidazole-5-carboxylic acid N-[4-(4-pyridyl)thiazol-2-yl] amide (L51)

Prepared from 1-(3-tert-butyloxycarbonylamino-1-propyl)-2-methylbenzimidazole-5-carboxylic acid and 2-amino-4-(4-pyridyl)thiazole following General Procedure A. ESI-MS: 393 (M+1).

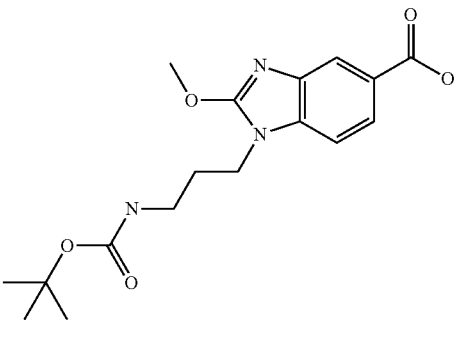 [SMILES: COc1nc2cc(C(=O)O)ccc2n1CCCNC(=O)OC(C)(C)C]

Synthesis of 1-(3-tert-butyloxycarbonylamino-1-propyl)-2-methoxybenzimidazole-5-carboxylic acid To 3-amino-4-[(3-tert-butyloxycarbonylamino-1-propyl)amino]benzoic acid (synthesis, see before; 0.5 mmol) in dioxane (2 mL) was added tetramethylorthocarbonate (2 mmol) in a glass vial. The vial was thoroughly closed and the mixture was heated to 100° C. for 1 h, whereupon the solvents were evaporated. The residue was purified by flash column chromatography (SiO₂ stationary phase, methanol in dichloromethane gradient elution), furnishing 1-(3-tert-butyloxycarbonylamino-1-propyl)-2-methoxybenzimidazole-5-carboxylic acid as a brownish solid.

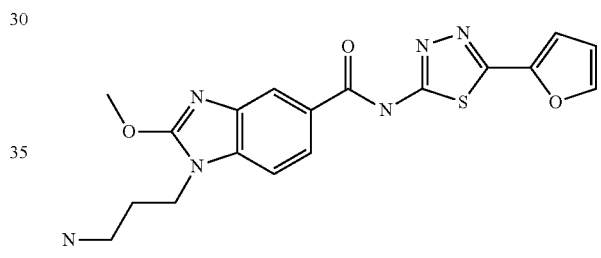

Synthesis of 1-(3-amino-1-propyl)-2-methoxybenzimidazole-5-carboxylic acid N-[5-(2-furyl)-1,3,4-thiadiazol-2-yl] amide (L45)

Prepared from 1-(3-tert-butyloxycarbonylamino-1-propyl)-2-methoxybenzimidazole-5-carboxylic acid and 2-amino-5-(2-furyl)-1,3,4-thiadiazole following General Procedure A (protecting group cleavage was conducted with lower concentration of trifluoroacetic acid and minimal reaction time to avoid acidic cleavage/hydrolysis of the methoxy group). ESI-MS: 399 (M+1).

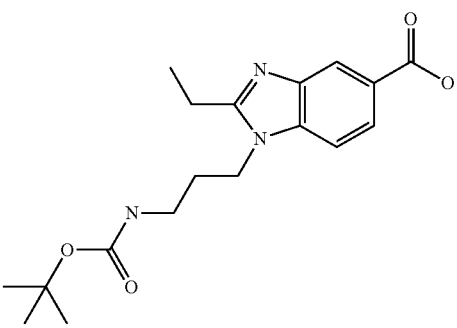 [SMILES: CCc1nc2cc(C(=O)O)ccc2n1CCCNC(=O)OC(C)(C)C]

Synthesis of 1-(3-tert-butyloxycarbonylamino-1-propyl)-2-ethylbenzimidazole-5-carboxylic acid To 3-amino-4-[(3-tert-butyloxycarbonylamino-1-propyl)amino]benzoic acid (synthesis, see before; 0.5 mmol) in dioxane (2 mL) was added triethylorthopropionate (2 mmol) in a glass vial. The vial was thoroughly closed and the mixture was heated to 100° C. for 1 h, whereupon the solvents were evaporated. The residue was purified by flash column chromatography (SiO$_2$ stationary phase, methanol in dichloromethane gradient elution), furnishing 1-(3-tert-butyloxycarbonylamino-1-propyl)-2-ethylbenzimidazole-5-carboxylic acid as a brownish solid.

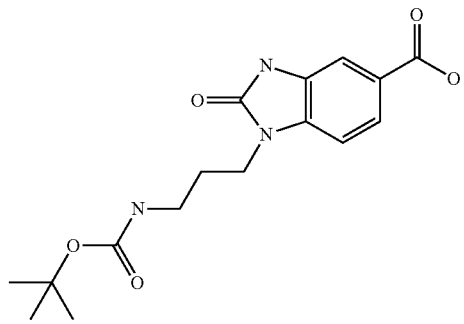

Synthesis of 1-(3-tert-butyloxycarbonylamino-1-propyl)-2-oxo-2,3-dihydrobenzimidazole-5-carboxylic acid To 3-amino-4-[(3-tert-butyloxycarbonylamino-1-propyl)amino]benzoic acid (synthesis, see before; 0.2 mmol) in dichloromethane (2 mL) was added DIPEA (1 mmol) and chlorotrimethylsilane (0.6 mmol). After agitating for 5 min, a solution of bis(trichloromethyl)carbonate (0.1 mmol) in dichloromethane (1 mL) was added dropwise and agitating was continued for 5 min. Saturated aqueous sodium bicarbonate (200 µL) was added and the mixture was shaken for 2 min, then aqueous citric acid (5%) was added and the organic layer was separated. The aqueous layer was extracted once again with dichloromethane, and the combined organic layers were washed with aqueous citric acid (5%) and water, subsequently the suspension that had formed was evaporated to dryness. The residue was extracted with ethyl acetate (1 mL) and TBME (0.5 mL), followed by additional extraction with TBME. The combined organic layers were evaporated to dryness and dried in high vacuum. The crude 1-(3-tert-butyloxycarbonylamino-1-propyl)-2-oxo-2,3-dihydrobenzimidazole-5-carboxylic acid was used without further purification.

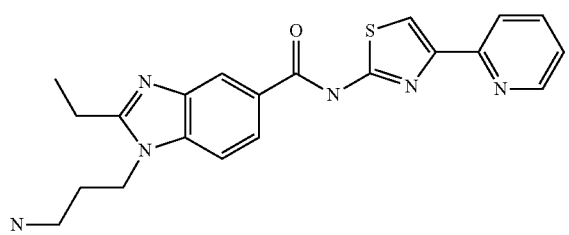 [SMILES: CCc1nc2cc(C(=O)Nc3nc(-c4ccccn4)cs3)ccc2n1CCCN]

Synthesis of 1-(3-amino-1-propyl)-2-ethylbenzimidazole-5-carboxylic acid N-[4-(2-pyridyl)thiazol-2-yl] amide (L43)

Prepared from 1-(3-tert-butyloxycarbonylamino-1-propyl)-2-ethylbenzimidazole-5-carboxylic acid and 2-amino-4-(2-pyridyl)thiazole following General Procedure A. ESI-MS: 407 (M+1).

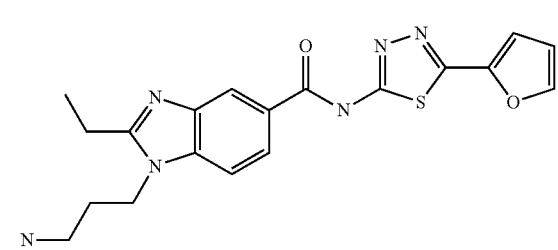 [SMILES: CCc1nc2cc(C(=O)Nc3nnc(-c4ccco4)s3)ccc2n1CCCN]

Synthesis of 1-(3-amino-1-propyl)-2-ethylbenzimidazole-5-carboxylic acid N-[5-(2-furyl)-1,3,4-thiadiazol-2-yl] amide (L44)

Prepared from 1-(3-tert-butyloxycarbonylamino-1-propyl)-2-ethylbenzimidazole-5-carboxylic acid and 2-amino-5-(2-furyl)-1,3,4-thiadiazole following General Procedure A. ESI-MS: 397 (M+1).

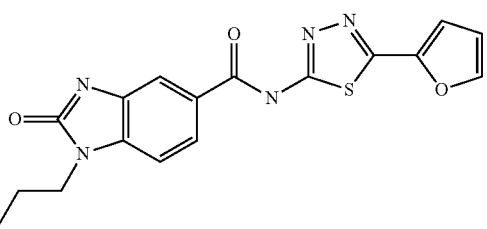

Synthesis of 1-(3-amino-1-propyl)-2-oxo-2,3-dihydrobenzimidazole-5-carboxylic acid N-[5-(2-furyl)-1,3,4-thiadiazol-2-yl] amide (L24)

Prepared from 1-(3-tert-butyloxycarbonylamino-1-propyl)-2-oxo-2,3-dihydrobenzimidazole-5-carboxylic acid and 2-amino-5-(2-furyl)-1,3,4-thiadiazole following General Procedure A. ESI-MS: 385 (M+1).

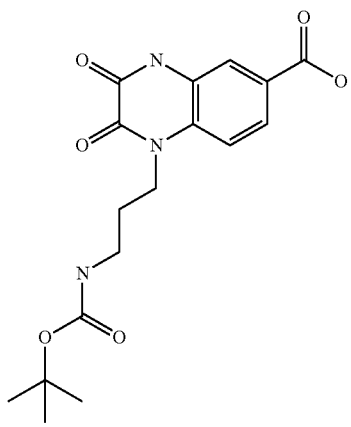 [SMILES: CC(C)(C)OC(=O)NCCCn1c(=O)c(=O)[nH]c2cc(C(=O)O)ccc21]

Synthesis of 1-(3-tert-butoxycarbonylamino-1-propyl)-2,3-dioxo-1,2,3,4-tetrahydroquinoxaline-6-carboxylic acid To 3-amino-4-[(3-tert-butyloxycarbonylamino-1-propyl)amino]benzoic acid (synthesis, see before; 0.2 mmol) in dichloromethane (2 mL) was added DIPEA (1 mmol) and chlorotrimethylsilane (0.6 mmol). After agitating for 5 min, a solution of oxalyl chloride (0.3 mmol) in dichloromethane (1 mL) was added dropwise and agitating was continued for 5 min. Saturated aqueous sodium bicarbonate (200 μL) was added and the mixture was shaken for 2 min, then aqueous citric acid (5%) was added and the organic layer was separated. The aqueous layer was extracted once again with dichloromethane, and the combined organic layers were washed with aqueous citric acid (5%) and water, subsequently the suspension that had formed was evaporated to dryness. The residue was dried in high vacuum. The crude 1-(3-tert-butoxycarbonylamino-1-propyl)-2,3-dioxo-1,2,3,4-tetrahydroquinoxaline-6-carboxylic acid was used without further purification.

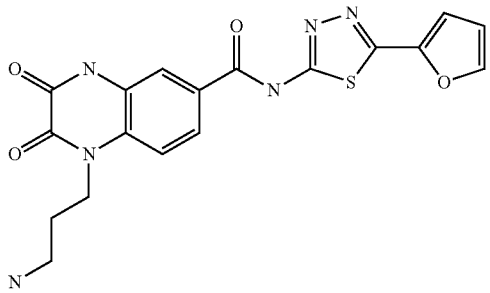 [SMILES: NCCCn1c(=O)c(=O)[nH]c2cc(C(=O)Nc3nnc(-c4ccco4)s3)ccc21]

Synthesis of 1-(3-amino-1-propyl)-2,3-dioxo-1,2,3,4-tetrahydroquinoxaline-6-carboxylic acid N-[5-(2-furyl)-1,3,4-thiadiazol-2-yl]amide (L28)

Prepared from 1-(3-tert-butoxy carbonylamino-1-propyl)-2,3-dioxo-1,2,3,4-tetrahydroquinoxaline-6-carboxylic acid and 2-amino-5-(2-furyl)-1,3,4-thiadiazole following General Procedure A. ESI-MS: 413 (M+1).

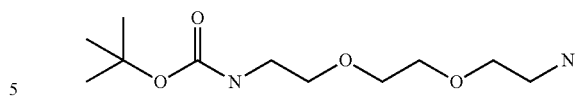

Synthesis of 1-amino-8-(tert-butoxycarbonyl)amino-3,5-dioxaoctane 1,8-Diamino-3,5-dioxaoctane (135 mmol) was dissolved in dichloromethane (100 mL). A solution of di-tert-butyldicarbonate (45 mmol) in dichloromethane (50 mL) was slowly added while stirring. After 1 h the solvent was removed and the residue was diluted with ethyl acetate (200 mL), washed three times with aqueous sodium carbonate (10%), dried with sodium sulphate, filtered and evaporated to dryness. After drying the colorless oil in high vacuum, the crude product was used without further purification.

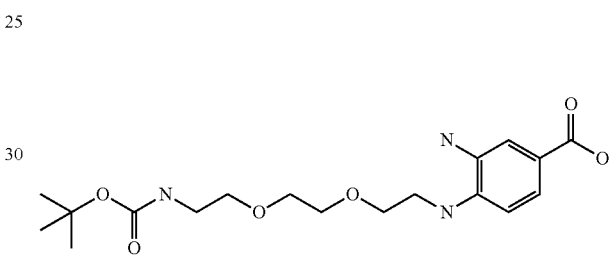

Synthesis of 4-amino-3-[8-(tert-butoxycarbonyl)amino-3,5-dioxa-1-octyl]aminobenzoic acid 1-Amino-8-(tert-butoxycarbonyl)amino-3,5-dioxaoctane (6 mmol) and DIPEA (10 mmol) were dissolved in dioxane (5 mL). A solution of 4-fluoro-3-nitrobenzoic acid (5 mmol) in dioxane (5 mL) was added and the mixture was heated to reflux for 2 h, whereupon another portion of 1-amino-8-(tert-butoxycarbonyl)amino-3,5-dioxaoctane (2 mmol) in dioxane (2 mL) was added and heating was continued for 1 h. The solvent was evaporated and the residue was dissolved in ethyl acetate (50 mL) and washed with aqueous citric acid (5%) and water. The solvent was removed and the residue was dried in high vacuum.

To the residue was added palladium on activated carbon (5%, moistened with 50% water; Degussa Type E 101 NO/W; 50 mg) and methanol (20 mL) under argon. Triethylsilane (4 mL) was added dropwise over 10 min. After stirring for 20 min, additional triethylsilane (1 mL) was added over 2 min, then stirring was continued for 10 min. Subsequently, the mixture was filtered through celite, the filtrate was evaporated to dryness and the residue was dried in high vacuum and used without further purification. The synthesis was successfully repeated several times.

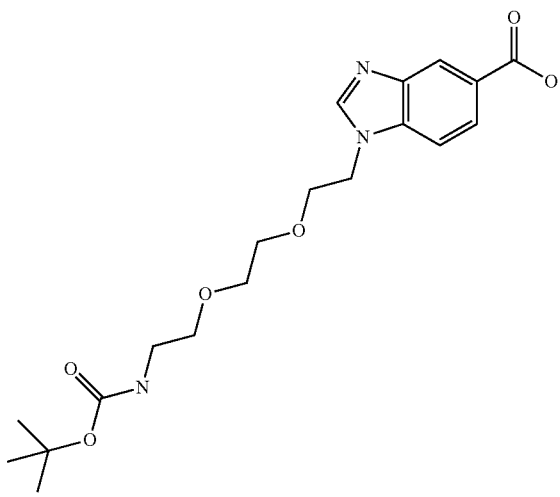 [SMILES: CC(C)(C)OC(=O)NCCOCCOCCn1cnc2cc(C(=O)O)ccc21]

Synthesis of 1-[8-(tert-butoxycarbonyl)amino-3,5-dioxa-1-octyl]benzimidazole-5-carboxylic acid 4-amino-3-[8-(tert-butoxycarbonyl)amino-3,5-dioxa-1-octyl]aminobenzoic acid (synthesis, see before; one complete batch of material was used) was dissolved in trimethylorthoformate (5 mL) and agitated at 80° C. for 1 h. The solvent was evaporated and the residue was purified by flash column chromatography (SiO$_2$ stationary phase, methanol in dichloromethane gradient elution), furnishing 1-[8-(tert-butoxycarbonyl)amino-3,5-dioxa-1-octyl]benzimidazole-5-carboxylic acid as a brownish solid.

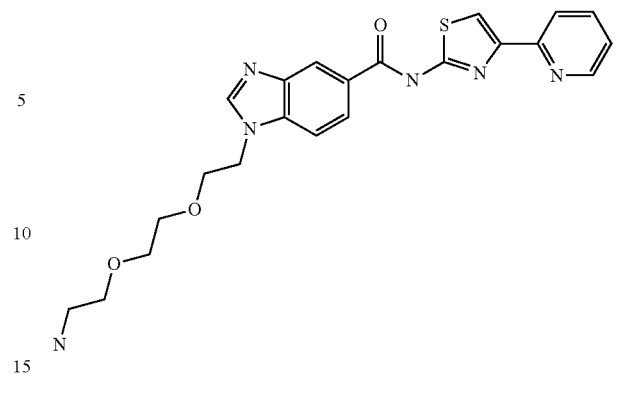

Synthesis of 1-(8-amino-3,5-dioxa-1-octyl)benzimidazole-5-carboxylic acid N-[4-(2-pyridyl)thiazol-2-yl] amide (L41)

Prepared from 1-[8-(tert-butoxycarbonyl)amino-3,5-dioxa-1-octyl]benzimidazole-5-carboxylic acid and 2-amino-4-(2-pyridyl)thiazole following General Procedure A. ESI-MS: 453 (M+1).

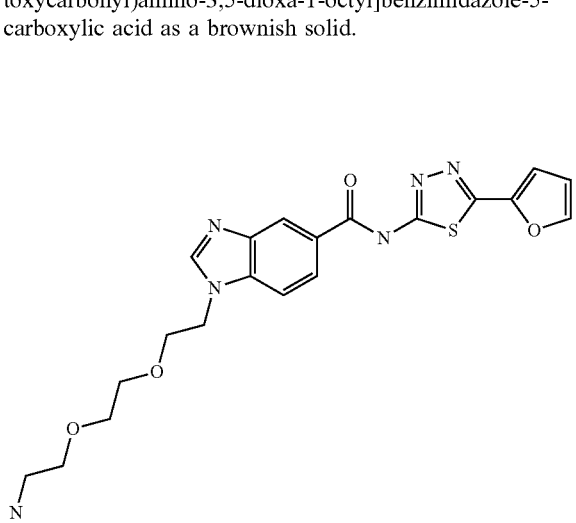

Synthesis of 1-(8-amino-3,5-dioxa-1-octyl)benzimidazole-5-carboxylic acid N-[5-(2-furyl)-1,3,4-thiadiazol-2-yl] amide (L25)

Prepared from 1-[8-(tert-butoxycarbonyl)amino-3,5-dioxa-1-octyl]benzimidazole-5-carboxylic acid and 2-amino-5-(2-furyl)-1,3,4-thiadiazole following General Procedure A. ESI-MS: 443 (M+1).

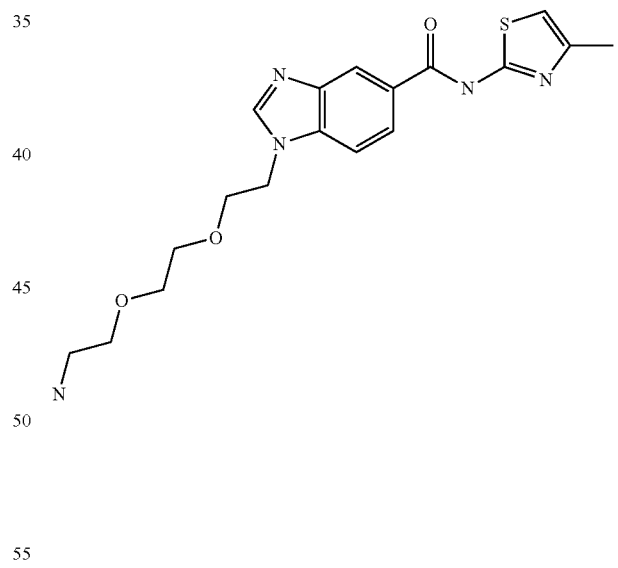

Synthesis of 1-(8-amino-3,5-dioxa-1-octyl)benzimidazole-5-carboxylic acid N-(4-methylthiazol-2-yl) amide (L29)

Prepared from 1-[8-(tert-butoxycarbonyl)amino-3,5-dioxa-1-octyl]benzimidazole-5-carboxylic acid and 2-amino-4-methylthiazole following General Procedure A. ESI-MS: 390 (M+1).

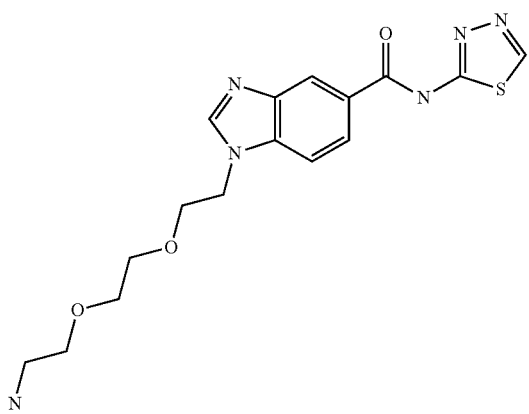 [SMILES: NCCOCCOCCn1cnc2cc(C(=O)Nc3nncs3)ccc21]

Synthesis of 1-(8-amino-3,5-dioxa-1-octyl)benzimidazole-5-carboxylic acid N-(1,3,4-thiadiazol-2-yl) amide (L27)

Prepared from 1-[8-(tert-butoxycarbonyl)amino-3,5-dioxa-1-octyl]benzimidazole-5-carboxylic acid and 2-amino-1,3,4-thiadiazole following General Procedure A. ESI-MS: 377 (M+1).

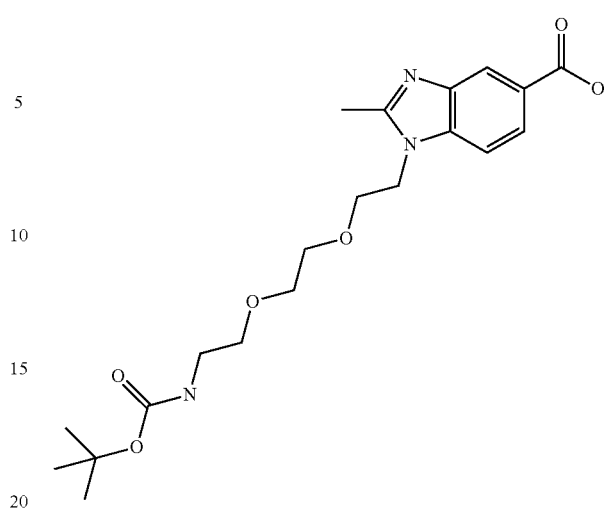

Synthesis of 1-[8-(tert-butoxycarbonyl)amino-3,5-dioxa-1-octyl]-2-methylbenzimidazole-5-carboxylic acid 4-Amino-3-[8-(tert-butoxycarbonyl)amino-3,5-dioxa-1-octyl]aminobenzoic acid (synthesis, see before; one complete batch of material was used) was dissolved in dioxane (20 mL), treated with trimethylorthoacetate (20 mmol) and heated to reflux for 1 h. The solvent was evaporated and the residue was purified by flash column chromatography (SiO$_2$ stationary phase, methanol in dichloromethane gradient elution), furnishing 1-[8-(tert-butoxycarbonyl)amino-3,5-dioxa-1-octyl]-2-methylbenzimidazole-5-carboxylic acid as a brownish solid.

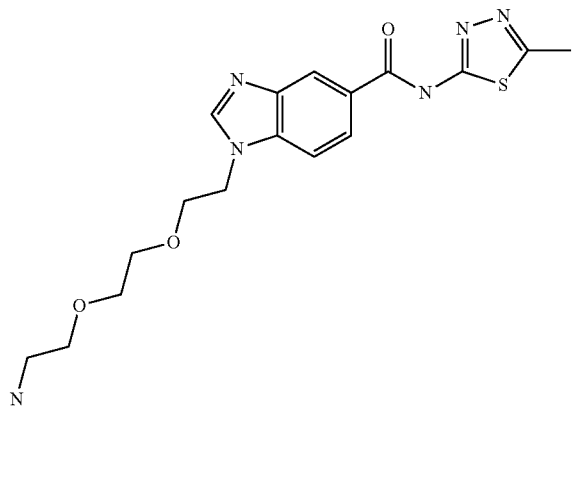 [SMILES: Cc1nnc(NC(=O)c2ccc3c(c2)ncn3CCOCCOCCN)s1]

Synthesis of 1-(8-amino-3,5-dioxa-1-octyl)benzimidazole-5-carboxylic acid N-(5-methyl-1,3,4-thiadiazol-2-yl) amide (L26)

Prepared from 1-[8-(tert-butoxycarbonyl)amino-3,5-dioxa-1-octyl]benzimidazole-5-carboxylic acid and 2-amino-5-methyl-1,3,4-thiadiazole following General Procedure A. ESI-MS: 391 (M+1).

Synthesis of 1-(8-amino-3,5-dioxa-1-octyl)-2-methylbenzimidazole-5-carboxylic acid N-[5-(2-furyl)-1,3,4-thiadiazol-2-yl] amide (L49)

Prepared from 1-[8-(tert-butoxycarbonyl)amino-3,5-dioxa-1-octyl]-2-methylbenzimidazole-5-carboxylic acid and 2-amino-5-(2-furyl)-1,3,4-thiadiazole following General Procedure A. ESI-MS: 457 (M+1).

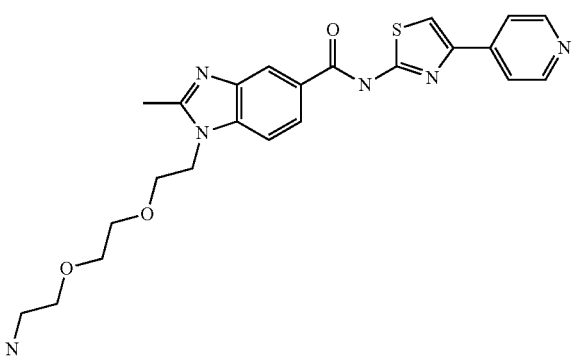 [SMILES: Cc1nc2cc(C(=O)Nc3nc(-c4ccncc4)cs3)ccc2n1CCOCCOCCN]

Synthesis of 1-(8-amino-3,5-dioxa-1-octyl)-2-methylbenzimidazole-5-carboxylic acid N-[4-(4-pyridyl)thiazol-2-yl] amide (L52)

Prepared from 1-[8-(tert-butoxycarbonyl)amino-3,5-dioxa-1-octyl]-2-methylbenzimidazole-5-carboxylic acid and 2-amino-4-(4-pyridyl)thiazole following General Procedure A. ESI-MS: 467 (M+1).

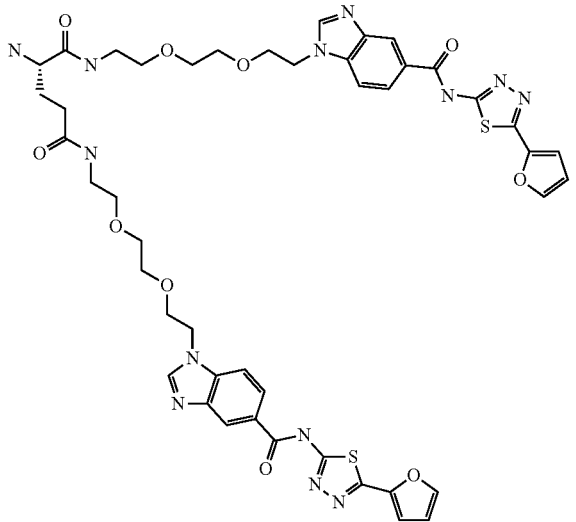 [SMILES: N[C@@H](CCC(=O)NCCOCCOCCn1cnc2cc(C(=O)Nc3nnc(-c4ccco4)s3)ccc21)C(=O)NCCOCCOCCn1cnc2cc(C(=O)Nc3nnc(-c4ccco4)s3)ccc21]

Synthesis of (S)-glutamic acid N,N'-bis{8-{5-[5-(2-furyl)-1,3,4-thiadiazol-2-ylcarbamoyl]benzimidazol-1-yl}-3,5-dioxa-1-octyl} amide (L53)

1-(8-Amino-3,5-dioxa-1-octyl)benzimidazole-5-carboxylic acid N-[5-(2-furyl)-1,3,4-thiadiazol-2-yl] amide (L25) was prepared on a 500 µmol scale (synthesis, see before; no chromatographic purification was applied). The crude amine trifluoroacetate salt was treated with DMF (1 mL) and DIPEA (3 mmol). N-tert-Butoxycarbonylglutamic acid (0.2 mmol), HATU (0.4 mmol) and DIPEA (1 mmol) were dissolved in DMF (1 mL). After 5 min the mixture was added to the solution prepared before. After 20 min, TBME (2 mL) was added and the mixture was left standing for approx. 1 h, whereupon a thick precipitate formed which was separated by centrifugation, washed with ethyl acetate and TBME and dried cautiously with a stream of nitrogen. The resulting solid was treated with dichloromethane (2 mL) and trifluoroacetic acid (1 mL) for 30 min, then the solvents were removed and the residue was purified by preparative reverse-phase HPLC-MS. ESI-MS: 499 ((M+2)/2).

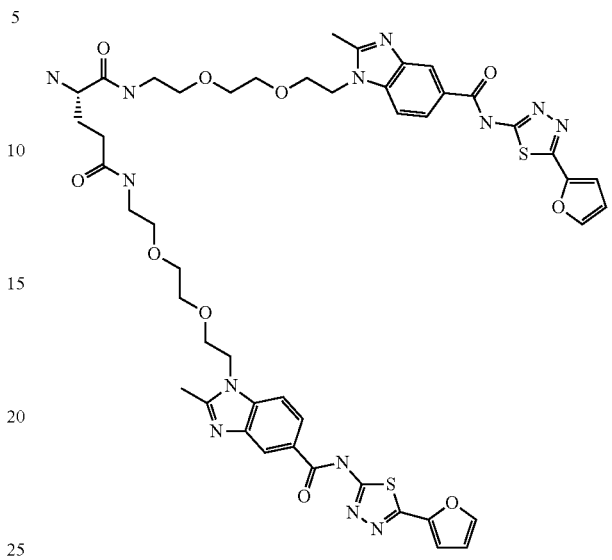

Synthesis of (S)-glutamic acid N,N'-bis{8-{5-[5-(2-furyl)-1,3,4-thiadiazol-2-ylcarbamoyl]-2-methylbenzimidazol-1-yl}-3,5-dioxa-1-octyl} amide (L54)

1-(8-Amino-3,5-dioxa-1-octyl)-2-methylbenzimidazole-5-carboxylic acid N-[5-(2-furyl)-1,3,4-thiadiazol-2-yl] amide (L49) was prepared on a 500 µmol scale (synthesis, see before; no chromatographic purification was applied). The crude amine trifluoroacetate salt was treated with DMF (1 mL) and DIPEA (3 mmol). N-tert-Butoxycarbonylglutamic acid (0.2 mmol), HATU (0.4 mmol) and DIPEA (1 mmol) were dissolved in DMF (1 mL). After 5 min the mixture was added to the solution prepared before. After 20 min, TBME (2 mL) was added and the mixture was left standing for approx. 1 h, whereupon a thick precipitate formed which was separated by centrifugation, washed with ethyl acetate and TBME and dried cautiously with a stream of nitrogen. The resulting solid was treated with dichloromethane (2 mL) and trifluoroacetic acid (1 mL) for 30 min, then the solvents were removed and the residue was purified by preparative reverse-phase HPLC-MS. ESI-MS: 513 ((M+2)/2).

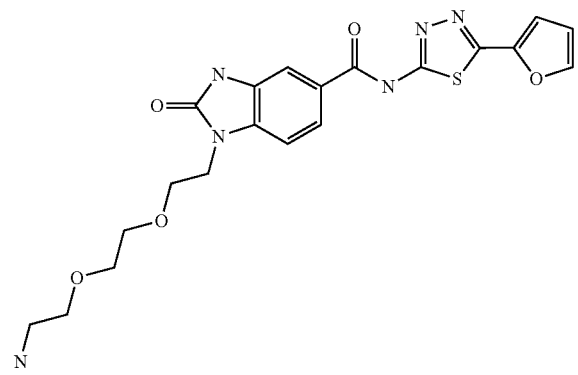 [SMILES: NCCOCCOCCn1c(=O)[nH]c2cc(C(=O)Nc3nnc(-c4ccco4)s3)ccc21]

Synthesis of 1-(8-amino-3,5-dioxa-1-octyl)-2-oxo-2,
3-dihydrobenzimidazole-5-carboxylic acid N-[5-(2-
furyl)-1,3,4-thiadiazol-2-yl] amide (L50)

4-amino-3-[8-(tert-butoxycarbonyl)amino-3,5-dioxa-1-octyl]aminobenzoic acid (1 mmol; synthesis, see before) was dissolved in dioxane (4 mL), treated with tetramethylorthocarbonate (4 mmol) and heated to 100° C. for 1 h. The solvent was evaporated and the residue was purified by flash column chromatography ($SiO_2$ stationary phase, methanol in dichloromethane gradient elution), furnishing 1-[8-(tert-butoxycarbonyl)amino-3,5-dioxa-1-octyl)-2-methoxybenzimidazole-5-carboxylic acid.

The carboxylic acid (0.1 mmol), HATU (0.1 mmol) and DIPEA (0.2 mmol) were dissolved in acetonitrile (1 mL). After 10 min, the solution was added to 2-amino-5-(2-furyl)-1,3,4-thiadiazole (0.1 mmol), and the mixture was heated to 120° C. for 90 min under microwave irradiation. After cooling to room temperature, the precipitate was separated, washed with TBME, dried cautiously in a stream of nitrogen and treated with trifluoroacetic acid (1 mL). The solution was heated to 100° C. for 1 h under microwave irradiation. After cooling to room temperature, the solvent was removed and the residue was purified by preparative reverse-phase HPLC-MS, furnishing 1-(8-amino-3,5-dioxa-1-octyl)-2-oxo-2,3-dihydrobenzimidazole-5-carboxylic acid N-[5-(2-furyl)-1,3,4-thiadiazol-2-yl] amide. ESI-MS: 459 (M+1).

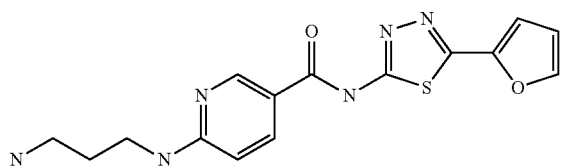 [SMILES: NCCCNc1ccc(C(=O)Nc2nnc(-c3ccco3)s2)cn1]

Synthesis of 6-[(3-amino-1-propyl)amino]nicotinic
acid N-[5-(2-furyl)-1,3,4-thiadiazol-2-yl]amide
(L19)

6-Chloronicotinic acid (0.2 mmol), HATU (0.2 mmol) and DIPEA (0.4 mmol) were dissolved in acetonitrile (1 mL). After 1 min the dark-red solution was added to 2-amino-5-(2-furyl)-1,3,4-thiadiazole (0.2 mmol) and the mixture was heated to 50° C. for 5 min. After cooling to room temperature, the precipitate that had formed was separated and washed with ethyl acetate and TBME and dried at air. Subsequently, 1,3-diaminopropane (1 mL) was added and the mixture was heated to 150° C. for 1 h under microwave irradiation. After removal of the solvent with a stream of nitrogen, the residue was purified by preparative reverse-phase HPLC-MS. ESI-MS: 345 (M+1).

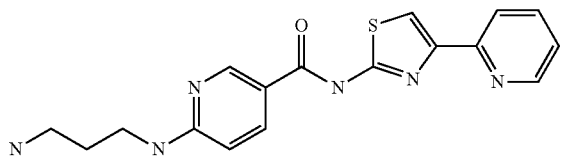 [SMILES: NCCCNc1ccc(C(=O)Nc2nc(-c3ccccn3)cs2)cn1]

Synthesis of 6-[(3-amino-1-propyl)amino]nicotinic
acid N-[4-(2-pyridyl)thiazol-2-yl]amide (L40)

6-Chloronicotinic acid (0.2 mmol), HATU (0.2 mmol) and DIPEA (0.4 mmol) were dissolved in acetonitrile (1 mL). After 1 min the dark-red solution was added to 2-amino-4-(2-pyridyl)thiazole (0.2 mmol) and the mixture was heated to 50° C. for 20 min.

After cooling to room temperature, the solvent was evaporated and the residue was dissolved in ethyl acetate and washed with aqueous citric acid (5%), saturated aqueous sodium carbonate and water. After evaporation of the solvent, 1,3-diaminopropane (1 mL) was added and the mixture was heated to 100° C. for 2 h under microwave irradiation. After removal of the solvent with a stream of nitrogen, the residue was purified by preparative reverse-phase HPLC-MS. ESI-MS: 355 (M+1).

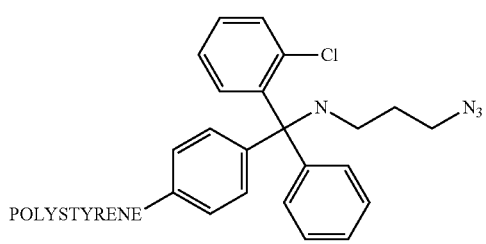

Synthesis of 3-azido-1-propylamine Linked to
2-chlorotrityl polystyrene Resin

Polystyrene resin preloaded with 2-chlorotrityl chloride (150 µmol) was treated with 3-amino-1-propanol (0.5 mL), followed by dichloromethane (2 mL). The slurry was agitated for 30 min, then the resin was washed thoroughly with DMF, methanol and dichloromethane (three times each) and dried in an air stream. To the dry resin was added dichloromethane (2 mL), DIPEA (1 mmol) and methanesulphonyl chloride (0.5 mmol). After shaking for 1 h at room temperature, the resin was washed three times with dichloromethane and dried in an air stream. The dry resin was transferred to a glass vial containing sodium azide (1 mmol). After addition of DMF (2 mL), the vial was closed thoroughly and the mixture was heated to 60° C. overnight. The resin was washed with water/methanol and DMSO (each twice).

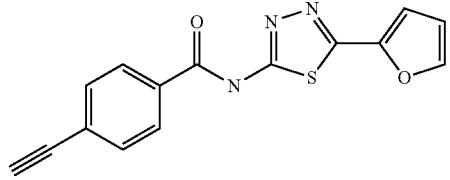 [SMILES: C#Cc1ccc(C(=O)Nc2nnc(-c3ccco3)s2)cc1]

Synthesis of 4-ethynylbenzoic acid
N-[5-(2-furyl)-1,3,4-thiadiazol-2-yl]amide

4-Bromobenzoic acid (0.2 mmol), HATU (0.2 mmol) and DIPEA (0.4 mmol) were dissolved in acetonitrile (1 mL). After 5 min the solution was added to 2-amino-5-(2-furyl)-1,3,4-thiadiazole (0.2 mmol). The mixture was heated to 100° C. for 60 min under microwave irradiation. After cooling to room temperature, the precipitate was separated and washed with ethyl acetate and TBME and dried cautiously with a stream of nitrogen.

The solid was suspended in tetrahydrofuran (1 mL) and added to bis(triphenylphosphinyl)palladium-(II) dichloride (5 µmol), triphenylphosphine (15 µmol) and copper-(I) iodide (15 µmol) in a microwave tube. The tube was flushed with argon while applying ultrasound, then it was sealed. After addition of triethylamine (0.5 mL) and ethynyltriisopropylsilane (0.5 mmol), the vial was flushed again with argon and heated to 100° C. for 3 h under microwave irradiation. Subsequently, all volative components were evaporated with a stream of nitrogen. The residue was treated with tetrahydrofuran (1 mL), water (10 µL) and tetra-n-butylammonium fluoride solution (1 M in THF, 0.5 mL). The mixture was agitated for 15 min, then the solvent was evaporated and the residue was separated from major by-products by adsorption to and elution from a short SiO$_2$ column (elution with ethyl acetate/methanol, approx. 4:1). After evaporation of the solvents, the product was dried in vacuo and used without further purification.

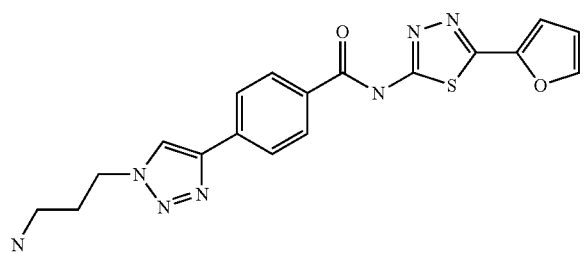 [SMILES: NCCCn1cc(-c2ccc(C(=O)Nc3nnc(-c4ccco4)s3)cc2)nn1]

Synthesis of 6-[1-(3-amino-1-propyl)triazol-4-yl] benzoic acid N-[5-(2-furyl)-1,3,4-thiadiazol-2-yl] amide (L48)

To 3-azido-1-propylamine linked to 2-chlorotrityl polystyrene resin (150 µmol; synthesis, see before) was added copper-(I) iodide (3 mg). The complete amount of 4-ethynylbenzoic acid N-[5-(2-furyl)-1,3,4-thiadiazol-2-yl]amide obtained before was dissolved in DMSO (2 mL) and added to the resin. After flushing with argon, the mixture was agitated overnight at 60° C. Subsequently, the resin was washed with DMF, water, methanol and dichloromethane (three times each) and dried. The product was cleaved from the support by twofold treatment with trifluoroacetic acid, dichloromethane and triethylsilane (45:45:10), followed by washing with dichloromethane. After evaporation of the solvents, the crude product was purified by preparative reverse-phase HPLC-MS. ESI-MS: 396 (M+1).

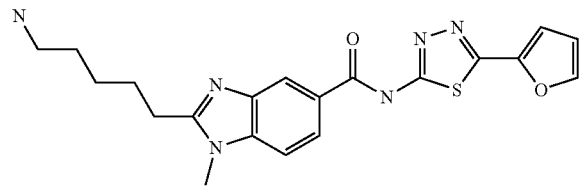 [SMILES: Cn1c(CCCCCN)nc2cc(C(=O)Nc3nnc(-c4ccco4)s3)ccc21]

Synthesis of 2-(5-amino-1-pentyl)-1-methylbenzimidazole-5-carboxylic acid N-[5-(2-furyl)-1,3,4-thiadiazol-2-yl]amide (L31)

4-Methylamino-3-nitrobenzoic acid (0.2 mmol), HATU (0.2 mmol) and DIPEA (0.4 mmol) were suspended in acetonitrile (1 mL) and agitated for 5 min, then the suspension was added to 2-amino-5-(2-furyl)-1,3,4-thiadiazole (0.2 mmol).

The mixture was heated to 100° C. for 20 min, then DMSO (0.1 mL) and acetonitrile (1 mL) were added and heating was continued for 1 h. After cooling to room temperature, the precipitate was collected, washed twice with ethyl acetate and dried cautiously with a stream of nitrogen.

As attempts towards the reduction of the nitro group using palladium on activated carbon and triethylsilane were unsuccessful, the residue was treated with tin-(II) chloride (1 mmol) in pyridine (1 mL) and water (50 µL) at 100° C. for 30 min. After cooling to room temperature, the solid was filtered off and rinsed thoroughly with methanol. The solvents were evaporated, and the residue was suspended in ethyl acetate. The suspension was washed three times with water and evaporated to dryness.

6-(tert-Butoxycarbonylamino)hexanoic acid (0.2 mmol), HATU (0.2 mmol) and DIPEA (0.4 mmol) were dissolved in acetonitrile (1 mL). After 2 min the solution was added to the residue obtained before and the mixture was agitated at room temperature for 75 min, whererupon the thick precipitate that had formed was separated, washed twice with ethyl acetate and dried cautiously with a stream of nitrogen. Trifluoroacetic acid (1 mL) was added and the mixture was agitated overnight. The mixture was evaporated to dryness and the residue was purified by preparative reverse-phase HPLC-MS. ESI-MS: 411 (M+1).

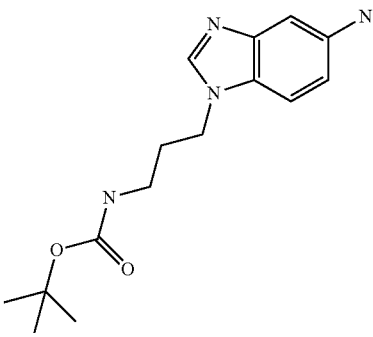 [SMILES: CC(C)(C)OC(=O)NCCCn1cnc2cc(N)ccc21]

Synthesis of 5-amino-1-(3-tert-butoxycarbonylamino-1-propyl)benzimidazole

To 3-(tert-butoxycarbonylamino)-1-propylamine (0.3 mmol) and DIPEA (0.5 mmol) was added a solution of 2,4-dinitrofluorobenzene (0.25 mmol) in dioxane (1 mL). The mixture was heated to 100° C. for 25 min, then the solvent was evaporated. The residue was dissolved in ethyl acetate and washed twice with aqueous citric acid (5%) and with water. The solvent was evaporated and the residue was treated with palladium on activated carbon (5%, moistened with 50% water; Degussa Type E 101 NO/W; 10 mg) and methanol (1 mL). The mixture was flushed with argon and triethylsilane (0.6 mL) was added. The mixture was shaken until decoloration of the supernatant, then trimethylorthoformate (1 mL) was added and the mixture was heated to 80° C. for 1 h under argon atmosphere. Subsequently, the suspension was filtered through celite which was rinsed with methanol. The solvent was evaporated and the residue was dried in vacuo.

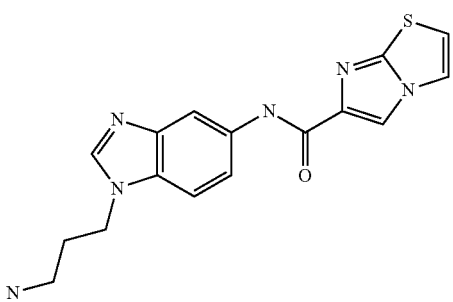 [SMILES: NCCCn1cnc2cc(NC(=O)c3cn4ccsc4n3)ccc21]

Synthesis of 1-(3-amino-1-propyl)-5-[(imidazo-[2,1-b]thiazol-6-yl)carboxamido]benzimidazole (L30)

Imidazo[2,1-b]thiazole-6-carboxylic acid (0.25 mmol), HATU (0.25 mmol) and DIPEA (0.5 mmol) were dissolved in acetonitrile (1 mL) and added to 5-amino-1-(3-tert-butoxycarbonylamino-1-propyl)benzimidazole (synthesis, see before; one entire batch was used) after 10 min. The mixture was shaken overnight at room temperature, then the solvent was evaporated, the residue was dissolved in ethyl acetate and washed with aqueous citric acid (5%), aqueous sodium carbonate and water and evaporated to dryness. To the residue was added dichloromethane (2 mL), followed by trifluoroacetic acid, and the mixture was agitated for 30 min at room temperature, whereupon the solvents were evaporated and the residue was purified by preparative reverse-phase HPLC-MS. ESI-MS: 341 (M+1).

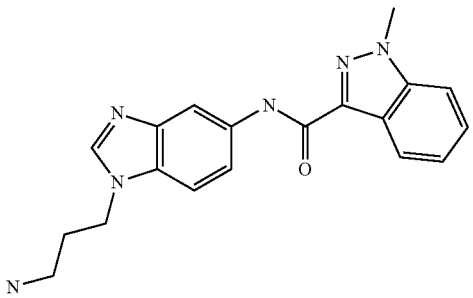 [SMILES: Cn1nc(C(=O)Nc2ccc3c(c2)ncn3CCCN)c2ccccc21]

Synthesis of 1-(3-amino-1-propyl)-5-[(1-methylindazol-3-yl)carboxamido]benzimidazole (L01)

The compound was prepared as described for 1-(3-amino-1-propyl)-5-[(imidazo-[2,1-b]thiazol-6-yl)carbamoyl]benzimidazole (L30), using 1-methylindazole-3-carboxylic acid instead of imidazo[2,1-b]thiazole-6-carboxylic acid. ESI-MS: 349 (M+1).

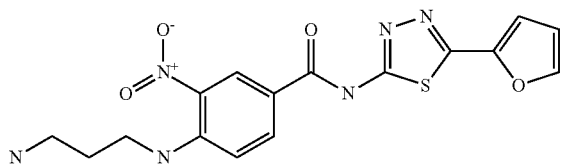 [SMILES: NCCCNc1ccc(C(=O)Nc2nnc(-c3ccco3)s2)cc1[N+](=O)[O-]]

Synthesis of 4-[(3-amino-1-propyl)amino]-3-nitrobenzoic acid N-[5-(2-furyl)-1,3,4-thiadiazol-2-yl] amide (L18)

3-(tert-butoxycarbonylamino)-1-propylamine (0.3 mmol), 4-fluoro-3-nitrobenzoic acid (0.3 mmol) and DIPEA (0.6 mmol) in dioxane (2 mL) were heated to 100° C. for 40 min, subsequently the solvent was evaporated. To the residue, HATU (0.3 mmol) in acetonitrile (1 mL) and DIPEA (0.6 mmol) were added and the mixture was agitated for 5 min at room temperature. After addition of 2-amino-5-(2-furyl)-1,3,4-thiadiazole (0.3 mmol) in acetonitrile (1 mL), the mixture was heated to 100° C. for 20 min. Upon cooling to room temperature, a solid precipitated which was collected, washed three times with ethyl acetate and dried with a stream of nitrogen. Subsequently, dichloromethane (2 mL) and trifluoroacetic acid (1 mL) were added and the mixture was agitated for 30 min, whereupon the solvents were evaporated. The residue was purified by flash column chromatography on a NH$_2$-modified stationary phase using a methanol in dichloromethane (containing 1% of triethylamine) gradient. ESI-MS: 389 (M+1).

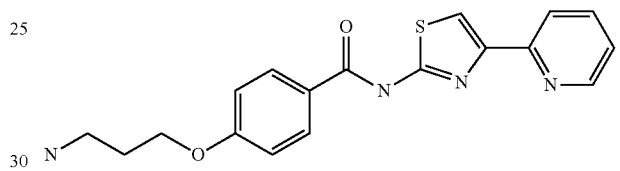

Synthesis of 4-[(1-amino-3-propyl)oxy]benzoic acid N-[4-(2-pyridyl)thiazol-2-yl] amide (L38)

Polystyrene resin preloaded with 2-chlorotrityl chloride (150 μmol) was treated with 3-amino-1-propanol (0.5 mL), followed by dichloromethane (2 mL). The slurry was agitated for 30 min, then the resin was washed thoroughly with DMF, methanol and dichloromethane (three times each) and dried in stream of nitrogen. To the dry resin was added triphenylphosphine (1 mmol) and methyl 4-hydroxybenzoate (1 mmol). After addition of dry tetrahydrofuran (2 mL), the mixture was agitated until the resin was sufficiently swollen. Then N,N'-azodicarboxylic acid diisopropyl ester (1 mmol) was added dropwise and the mixture was shaken for 2 h. After this time the resin was washed with DMF, methanol and dichloromethane (three times each). The dry resin was transferred to a glass vial and treated with tetrahydrofurn (2 mL), methanol (1 mL) and aqueous sodium hydroxide (2 N, 1 mL). The vial was thoroughly closed and the mixture was heated to 80° C. for 3 h, then the resin was washed with DMF, acetic acid in DMF (approx. 5%), DMF, methanol and dichloromethane (three times each).

The resin was swollen in NMP. After addition of NMP (1 mL), HATU (0.2 mmol) and DIPEA (0.4 mmol), the mixture was agitated for 10 min, whereupon 2-amino-4-(2-pyridyl)thiazole (0.2 mmol) in NMP (1 mL) was added. The vial was flushed with argon and the mixture was heated to 120° C. for 90 min under microwave irradiation. Then the resin was washed (DMF, methanol, dichloromethane, three times each) and the target compound was cleaved from the support by twofold treatment with trifluoroacetic acid, dichloromethane and triethylsilane (45:45:10), followed by rinsing with dichloromethane. After evaporation of the solvents, the residue was purified by preparative reverse-phase HPLC-MS. ESI-MS: 355 (M+1).

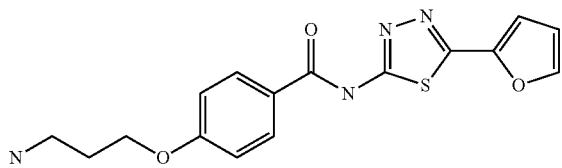

Synthesis of 4-[(1-amino-3-propyl)oxy]benzoic acid N-[5-(2-furyl)-1,3,4-thiadiazol-2-yl]amide (L20)

The compound was prepared as described for 4-(1-amino-3-propyloxy)benzoic acid N-[4-(2-pyridyl)thiazol-2-yl] amide (L38), using 2-amino-5-(2-furyl)-1,3,4-thiadiazole instead of 2-amino-4-(2-pyridyl)thiazole. ESI-MS: 345 (M+1).

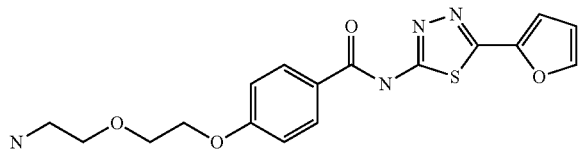 [SMILES: NCCOCCOc1ccc(C(=O)Nc2nnc(-c3ccco3)s2)cc1]

Synthesis of 4-(5-amino-3-oxa-1-pentyloxy)benzoic acid N-[5-(2-furyl)-1,3,4-thiadiazol-2-yl] amide (L37)

Polystyrene resin preloaded with 2-chlorotrityl chloride (150 µmol) was treated with aminoethoxyethanol (0.5 mL), followed by dichloromethane (2 mL). The slurry was agitated for 30 min, then the resin was washed thoroughly with DMF, methanol and dichloromethane (three times each) and dried in high vacuum. To the dry resin was added triphenylphosphine (1 mmol) and methyl 4-hydroxybenzoate (1 mmol). After addition of dry tetrahydrofuran (2 mL), the mixture was agitated until the resin was sufficiently swollen. Then N,N'-azodicarboxylic acid diisopropyl ester (1 mmol) was added dropwise and the mixture was shaken for 2 h. After this time the resin was washed with DMF, methanol and dichloromethane (three times each). The dry resin was transferred to a glass vial and treated with tetrahydrofurn (2 mL), methanol (1 mL) and aqueous sodium hydroxide (2 N, 1 mL). The vial was thoroughly closed and the mixture was heated to 60° C. for 2 h and to 80° C. for 30 min, then the resin was washed with DMF, acetic acid in DMF (approx. 5%), methanol and dichloromethane (three times each).

The resin was swollen in NMP. After addition of NMP (1 mL), HATU (0.2 mmol) and DIPEA (0.4 mmol), the mixture was agitated for 10 min, whereupon 2-amino-5-(2-furyl)-1,3,4-thiadiazole (0.2 mmol) in NMP (1 mL) was added. The vial was flushed with argon and the mixture was heated to 120° C. for 90 min under microwave irradiation. Then the resin was washed (DMF, methanol, dichloromethane, three times each) and the target compound was cleaved from the support by twofold treatment with trifluoroacetic acid, dichloromethane and triethylsilane (45:45:10), followed by rinsing with dichloromethane. After evaporation of the solvents, the residue was purified by preparative reverse-phase HPLC-MS. ESI-MS: 375 (M+1).

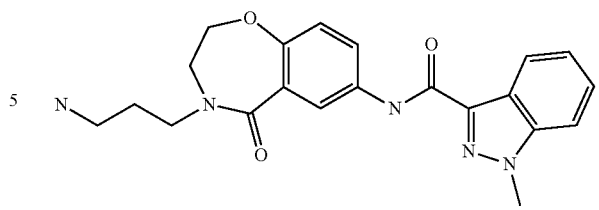

Synthesis of 4-(3-amino-1-propyl)-7-[(1-methylindazol-3-yl)carboxamido]-2,3,4,5-tetrahydrobenzo[f][1,4]oxazepin-5-one (L03)

To 2-chlorotrityl chloride polystyrene resin (150 µmol) was added 3-aminopropan-1-ol (1 mL) and dichloromethane (1 mL) and the mixture was agitated for 20 min prior to washing the resin with DMF, methanol and dichloromethane (three times each). The resin was dried and treated with DIPEA (1 mmol) in dichloromethane (1 mL), followed by dropwise addition of methanesulphonyl chloride (0.5 mmol) in dichloromethane (1 mL). The mixture was shaken at room temperature for 20 min, then the resin was washed three times with dichloromethane, dried, transferred to a glass vial and treated with ethanolamine (1 mL) and NMP (1 mL) at 100° C. for 2 h. Subsequently it was washed with DMF, methanol and dichloromethane (three times each).

2-Fluoro-5-nitrobenzoic acid (200 µmol) and TBTU (200 µmol) in NMP (1.5 mL) were treated with DIPEA (400 µmol) for 2 min. Subsequently, the mixture was added to the NMP-swollen resin and the mixture was agitated for 25 min prior to washing the resin as described before. After adding THF (2 mL), methanol (1 mL) and aqueous NaOH (2 M, 1 mL), the resin was agitated for three days, followed by thorough washing with methanol and dichloromethane.

The resin was treated with pyridine (0.5 mL) and anhydrous tin-(II)-chloride (1 mmol) in NMP (1.5 mL) and shaken at room temperature for 5.5 h, whereupon another portion of tin-(II)-chloride (0.5 mmol) in NMP (0.5 mL) was added. The mixture was shaken overnight and subsequently washed with methanol. Insoluble reaction by-products were separated from the resin by repeated careful flotation with methanol. After washing with dichloromethane, the resin was swollen in NMP. 1-Methyl-3-indazolecarboxylic acid (0.2 mmol) and HATU (0.2 mmol) in NMP (1.5 mL) were treated with DIPEA (0.4 mmol), and after 2 min the mixture was added to the resin and agitated for 5 h. The resin was washed with DMF, methanol and dichloromethane (three times each). The target compound was cleaved from the support by twofold treatment with trifluoroacetic acid (45%) and triethylsilane (10%) in dichloromethane, followed by thorough washing of the resin with dichloromethane. After evaporation of the solvents, the crude product was purified by preparative reverse-phase HPLC-MS. ESI-MS: 394 (M+1).

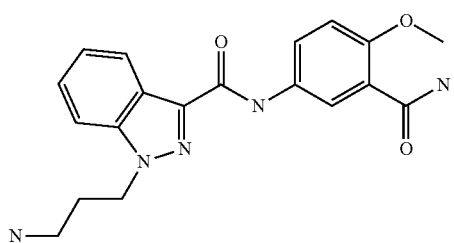 [SMILES: COc1ccc(NC(=O)c2nn(CCCN)c3ccccc23)cc1C(N)=O]

Synthesis of 1-(3-amino-1-propyl)indazole-3-carboxylic acid N-(3-carbamoyl-4-methoxyphenyl) amide (L04)

Polystyrene resin preloaded with a 9-fluorenylmethoxycarbonyl protected Sieber amide linker was swollen in dichloromethane followed by DMF. The resin was treated with piperidine (25% in DMF, approx. 3 mL) for 10 min, followed by washing with DMF, methanol and dichloromethane (three times each). 5-(9-Fluorenylmethoxycarbonyl)amino-2-methoxybenzoic acid (0.2 mmol) and HATU (0.2 mmol) were dissolved in NMP (1.5 mL) and treated with DIPEA (0.4 mmol). After 2 min the solution was added to the resin and the mixture was agitated for 30 min, then the resin was washed three times with DMF. After addition of piperidine (25% in DMF, approx. 3 mL), the mixture was agitated for 15 min and subsequently washed with DMF, methanol and dichloromethane (three times each).

Indazole-3-carboxylic acid (0.5 mmol) and 1-hydroxybenzotriazole (0.5 mmol) were dissolved in NMP (1.5 mL) and treated with N,N'-diisopropylcarbodiimide (0.5 mmol) for 2 min, whereupon the solution was added to the resin and the mixture was shaken for 1 h prior to washing (DMF, methanol, dichloromethane, three times each). After drying, the resin was transferred to a glass vial and treated with 1,3-dibromopropane (1 mmol) and DIPEA (1 mmol) in NMP at 60° C. overnight. The reaction was repeated once at 100° C. for 4.5 h, whereupon the resin was washed (DMF, methanol, dichloromethane, three times each) and re-transferred to a glass vial. After addition of tetrahydrofuran (2 mL) and concentrated aqueous ammonia (1 mL), the vial was thoroughly closed and the mixture was heated to 50° C. for 90 min. After addition of additional aqueous ammonia (1 mL), heating was continued overnight. After washing the resin with DMF, methanol and dichloromethane (three times each), the product was cleaved from the resin by threefold treatment with dichloromethane, trifluoroacetic acid and triethylsilane (85:10:5), followed by rinsing with dichloromethane. After evaporation of the solvents, the residue was purified by preparative reverse-phase HPLC-MS. ESI-MS: 368 (M+1).

extracted twice with ethyl acetate. The combined organic layers were washed twice with saturated aqueous sodium chloride solution, dried with magnesium sulphate, filtered and evaporated to dryness. Then palladium on activated carbon (5%, moistened with 50% water; Degussa Type E 101 NO/W; 15 mg) and methanol (2 mL) were added, followed by triethylsilane (500 μL; dropwise addition over 3 min). After shaking the mixture for additional 5 min, it was filtered through celite, evaporated to dryness, and the residue was treated with DMF (2 mL) and isopentyl nitrite (0.9 mmol) at 60° C. overnight in a thoroughly closed glass vial. After cooling to room temperature, aqueous citric acid (5%, 2 mL) was added and the mixture was extracted three times with ethyl acetate. The combined organic layers were washed three times with saturated aqueous sodium chloride solution, dried with magnesium sulphate, filtered, evaporated and dried in vacuo.

The residue was dissolved in dioxane (1 mL) and DIPEA (0.6 mmol) and treated with a solution of bis(trichloromethyl) carbonate (0.1 mmol) in dioxane (1 mL) for 30 min at room temperature. Subsequently, 3-amino-1-methylindazole (0.3 mmol) in dichloromethane (1 mL) was added and the mixture was agitated for 30 min, whereupon the solvents were evaporated and the residue was treated with saturated aqueous sodium carbonate solution (2 mL) and extracted twice with ethyl acetate. The combined organic layers were washed twice with aqueous citric acid (5%) and with saturated aqueous sodium carbonate, dried with magnesium sulphate, filtered through celite and evaporated to dryness.

The residue was treated with dichloromethane (2 mL), triethylsilane (0.1 mL) and trifluoroacetic acid (1 mL) for 15 min at room temperature. Then the solvents were evaporated and the residue was purified by preparative reverse-phase HPLC-MS. ESI-MS: 350 (M+1).

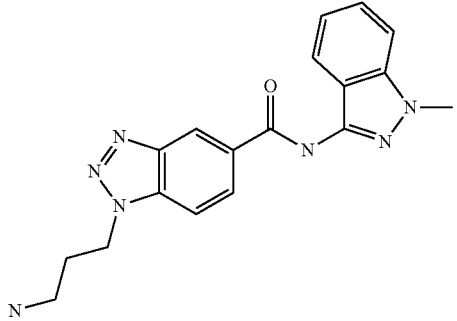 [SMILES: Cn1nc(NC(=O)c2ccc3c(c2)nnn3CCCN)c2ccccc21]

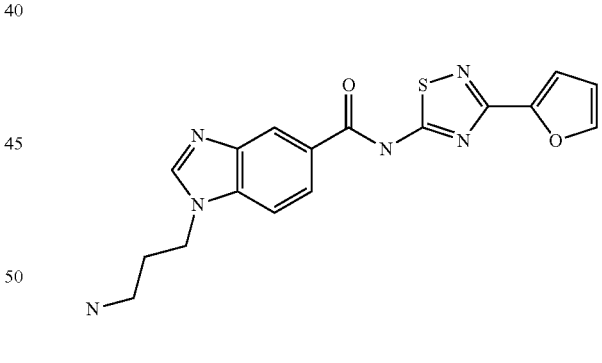

Synthesis of 1-(3-amino-1-propyl)benzotriazole-5-carboxylic acid N-(1-methylindazol-3-yl) amide (L06)

3-(tert-butoxycarbonylamino)-1-propylamine (0.3 mmol), 4-fluoro-3-nitrobenzoic acid (0.3 mmol) and DIPEA (0.6 mmol) in dioxane (2 mL) were heated to 100° C. for 1 h, subsequently the solvent was evaporated. To the residue was added aqueous citric acid (5%), and the mixture was

Synthesis of 1-(3-amino-1-propyl)benzimidazole-5-carboxylic acid N-[3-(2-furyl)-1,2,4-thiadiazol-5-yl] amide (L55)

The synthesis is carried out employing General Procedure A. As carboxylic acid component 1-[3-(tert-butoxycarbonyl)amino-1-propyl] benzimidazole-5-carboxylic acid (synthesis, see before) is used. As aromatic amine, 5-amino-3-(2-furyl)-1,2,4-thiadiazole is employed.

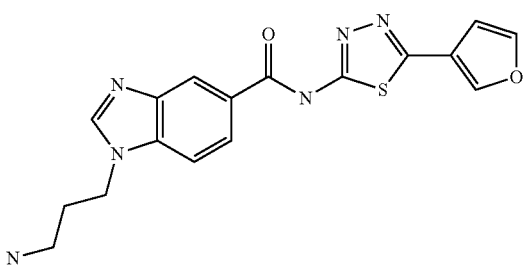 [SMILES: NCCCn1cnc2cc(C(=O)Nc3nnc(-c4ccoc4)s3)ccc21]

Synthesis of 1-(3-amino-1-propyl)benzimidazole-5-carboxylic acid N-[5-(3-furyl)-1,3,4-thiadiazol-2-yl] amide (L56)

The synthesis is carried out employing General Procedure A. As carboxylic acid component 1-[3-(tert-butoxycarbonyl)amino-1-propyl] benzimidazole-5-carboxylic acid (synthesis, see before) is used. As aromatic amine, 2-amino-5-(3-furyl)-1,3,4-thiadiazole is employed.

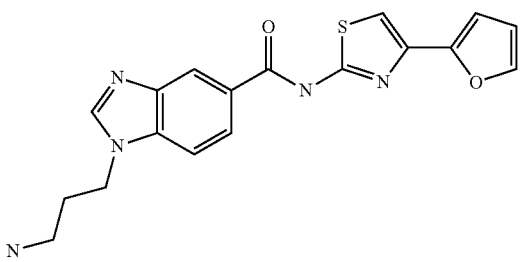 [SMILES: NCCCn1cnc2cc(C(=O)Nc3nc(-c4ccco4)cs3)ccc21]

Synthesis of 1-(3-amino-1-propyl)benzimidazole-5-carboxylic acid N-[4-(2-furyl)thiazol-2-yl] amide (L57)

The synthesis is carried out employing General Procedure A. As carboxylic acid component 1-[3-(tert-butoxycarbonyl)amino-1-propyl]benzimidazole-5-carboxylic acid (synthesis, see before) is used. As aromatic amine, 2-amino-4-(2-furyl)thiazole is employed.

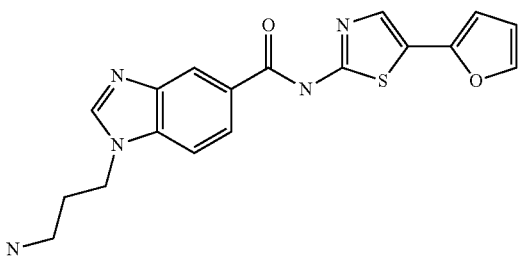 [SMILES: NCCCn1cnc2cc(C(=O)Nc3ncc(-c4ccco4)s3)ccc21]

Synthesis of 1-(3-amino-1-propyl)benzimidazole-5-carboxylic acid N-[5-(2-furyl)thiazol-2-yl] amide (L58)

The synthesis is carried out employing General Procedure A. As carboxylic acid component 1-[3-(tert-butoxycarbonyl)amino-1-propyl]benzimidazole-5-carboxylic acid (synthesis, see before) is used. As aromatic amine, 2-amino-5-(2-furyl)thiazole is employed.

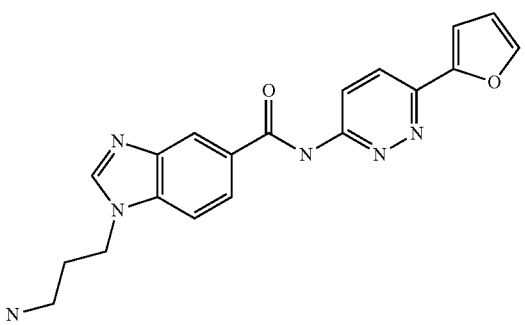 [SMILES: NCCCn1cnc2cc(C(=O)Nc3ccc(-c4ccco4)nn3)ccc21]

Synthesis of 1-(3-amino-1-propyl)benzimidazole-5-carboxylic acid N-[6-(2-furyl)pyridazin-3-yl] amide (L59)

The synthesis is carried out employing General Procedure A. As carboxylic acid component 1-[3-(tert-butoxycarbonyl)amino-1-propyl]benzimidazole-5-carboxylic acid (synthesis, see before) is used. As aromatic amine, 3-amino-6-(2-furyl)pyridazine is employed. The coupling time needs to be extended to 6-18 h at 120° C. under microwave irradiation.

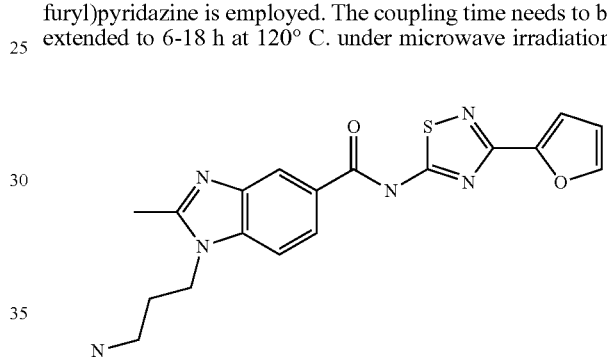

Synthesis of 1-(3-amino-1-propyl)-2-methylbenzimidazole-5-carboxylic acid N-[3-(2-furyl)-1,2,4-thiadiazol-5-yl] amide (L60)

The synthesis is carried out employing General Procedure A. As carboxylic acid component 1-[3-(tert-butoxycarbonyl)amino-1-propyl]-2-methylbenzimidazole-5-carboxylic acid (synthesis, see before) is used. As aromatic amine, 5-amino-3-(2-furyl)-1,2,4-thiadiazole is employed.

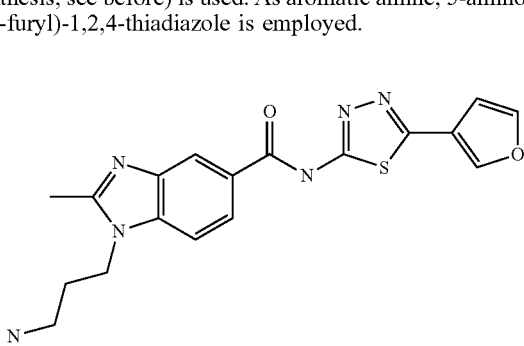

Synthesis of 1-(3-amino-1-propyl)-2-methylbenzimidazole-5-carboxylic acid N-[5-(3-furyl)-1,3,4-thiadiazol-2-yl] amide (L61)

The synthesis is carried out employing General Procedure A. As carboxylic acid component 1-[3-(tert-butoxycarbonyl)

amino-1-propyl]-2-methylbenzimidazole-5-carboxylic acid (synthesis, see before) is used. As aromatic amine, 2-amino-5-(3-furyl)-1,3,4-thiadiazole is employed.

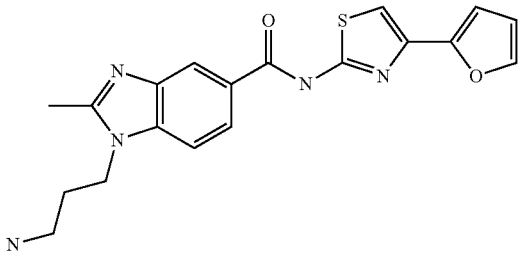 [SMILES: Cc1nc2cc(C(=O)Nc3nc(-c4ccco4)cs3)ccc2n1CCCN]

Synthesis of 1-(3-amino-1-propyl)-2-methylbenz-imidazole-5-carboxylic acid N-[4-(2-furyl)thiazol-2-yl] amide (L62)

The synthesis is carried out employing General Procedure A. As carboxylic acid component 1-[3-(tert-butoxycarbonyl)amino-1-propyl]-2-methylbenzimidazole-5-carboxylic acid (synthesis, see before) is used. As aromatic amine, 2-amino-4-(2-furyl)thiazole is employed.

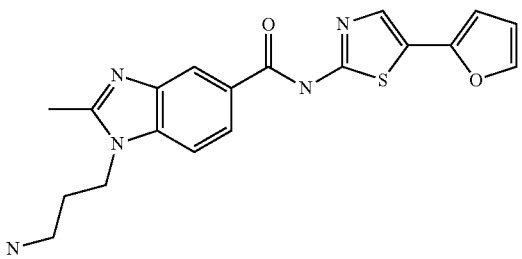 [SMILES: Cc1nc2cc(C(=O)Nc3ncc(-c4ccco4)s3)ccc2n1CCCN]

Synthesis of 1-(3-amino-1-propyl)-2-methylbenz-imidazole-5-carboxylic acid N-[5-(2-furyl)thiazol-2-yl] amide (L63)

The synthesis is carried out employing General Procedure A. As carboxylic acid component 1-[3-(tert-butoxycarbonyl)amino-1-propyl]-2-methylbenzimidazole-5-carboxylic acid (synthesis, see before) is used. As aromatic amine, 2-amino-5-(2-furyl)thiazole is employed.

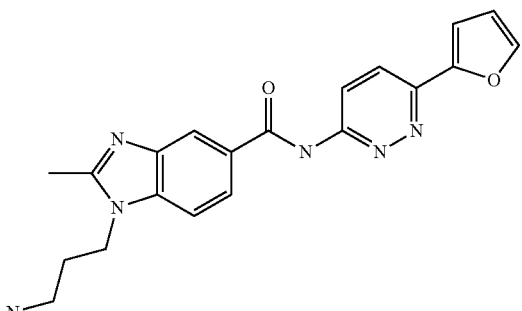

Synthesis of 1-(3-amino-1-propyl)-2-methylbenz-imidazole-5-carboxylic acid N-[6-(2-furyl)pyridazin-3-yl] amide (L64)

The synthesis is carried out employing General Procedure A. As carboxylic acid component 1-[3-(tert-butoxycarbonyl)amino-1-propyl]-2-methylbenzimidazole-5-carboxylic acid (synthesis, see before) is used. As aromatic amine, 3-amino-6-(2-furyl)pyridazine is employed. The coupling time needs to be extended to 6-18 h at 120° C. under microwave irradiation.

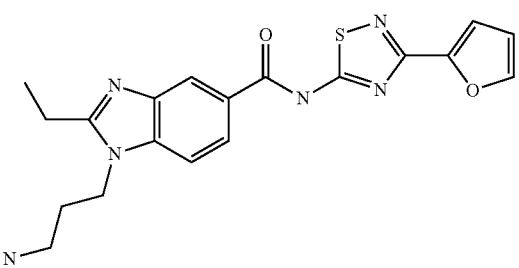 [SMILES: CCc1nc2cc(C(=O)Nc3nc(-c4ccco4)ns3)ccc2n1CCCN]

Synthesis of 1-(3-amino-1-propyl)-2-ethylbenzimi-dazole-5-carboxylic acid N-[3-(2-furyl)-1,2,4-thiadi-azol-5-yl] amide (L65)

The synthesis is carried out employing General Procedure A. As carboxylic acid component 1-[3-(tert-butoxycarbonyl)amino-1-propyl]-2-ethylbenzimidazole-5-carboxylic acid (synthesis, see before) is used. As aromatic amine, 5-amino-3-(2-furyl)-1,2,4-thiadiazole is employed.

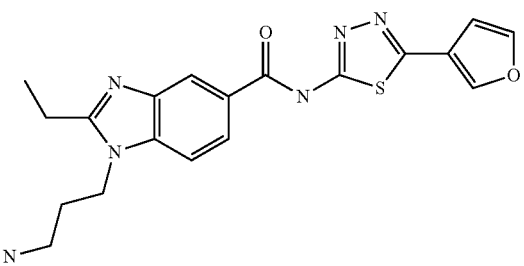 [SMILES: CCc1nc2cc(C(=O)Nc3nnc(-c4ccoc4)s3)ccc2n1CCCN]

Synthesis of 1-(3-amino-1-propyl)-2-ethylbenzimi-dazole-5-carboxylic acid N-[5-(3-furyl)-1,3,4-thiadi-azol-2-yl] amide (L66)

The synthesis is carried out employing General Procedure A. As carboxylic acid component 1-[3-(tert-butoxycarbonyl)amino-1-propyl]-2-ethylbenzimidazole-5-carboxylic acid (synthesis, see before) is used. As aromatic amine, 2-amino-5-(3-furyl)-1,3,4-thiadiazole is employed.

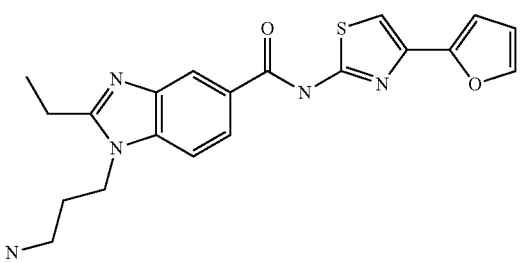 [SMILES: CCc1nc2cc(C(=O)Nc3nc(-c4ccco4)cs3)ccc2n1CCCN]

Synthesis of 1-(3-amino-1-propyl)-2-ethylbenzimidazole-5-carboxylic acid N-[4-(2-furyl)thiazol-2-yl] amide (L67)

The synthesis is carried out employing General Procedure A. As carboxylic acid component 1-[3-(tert-butoxycarbonyl)amino-1-propyl]-2-ethylbenzimidazole-5-carboxylic acid (synthesis, see before) is used. As aromatic amine, 2-amino-4-(2-furyl)thiazole is employed.

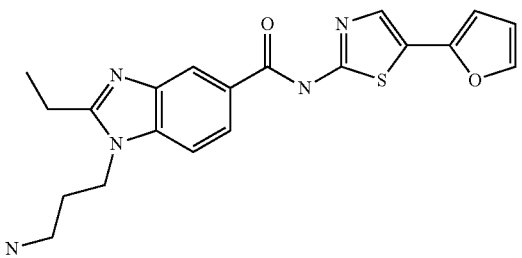 [SMILES: CCc1nc2cc(C(=O)Nc3ncc(-c4ccco4)s3)ccc2n1CCCN]

Synthesis of 1-(3-amino-1-propyl)-2-ethylbenzimidazole-5-carboxylic acid N-[5-(2-furyl)thiazol-2-yl] amide (L68)

The synthesis is carried out employing General Procedure A. As carboxylic acid component 1-[3-(tert-butoxycarbonyl)amino-1-propyl]-2-ethylbenzimidazole-5-carboxylic acid (synthesis, see before) is used. As aromatic amine, 2-amino-5-(2-furyl)thiazole is employed.

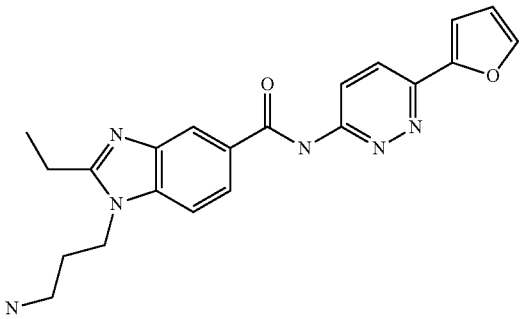 [SMILES: CCc1nc2cc(C(=O)Nc3ccc(-c4ccco4)nn3)ccc2n1CCCN]

Synthesis of 1-(3-amino-1-propyl)-2-ethylbenzimidazole-5-carboxylic acid N-[6-(2-furyl)pyridazin-3-yl] amide (L69)

The synthesis is carried out employing General Procedure A. As carboxylic acid component 1-[3-(tert-butoxycarbonyl)amino-1-propyl]-2-ethylbenzimidazole-5-carboxylic acid (synthesis, see before) is used. As aromatic amine, 3-amino-6-(2-furyl)pyridazine is employed. The coupling time needs to be extended to 6-18 h at 120° C. under microwave irradiation.

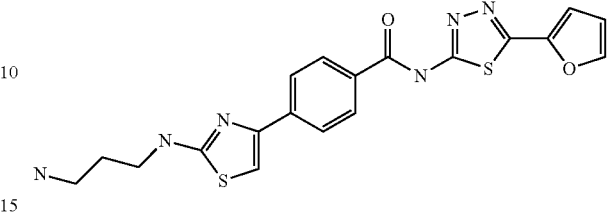

Synthesis of 4-[2-(3-amino-1-propylamino)thiazol-4-yl]benzoic acid N-[5-(2-furyl)-1,3,4-thiadiazol-2-yl] amide (L70)

The synthesis is carried out on insoluble support. Hence, trityl polystyrene resin pre-loaded with 1,3-diaminopropane (150 µmol) is reacted with N-(9-fluorenylmethoxycarbonyl) isocyanate (150-500 µmol) in 1-methylpyrrolidin-2-one or dichloromethane (1-5 mL) for 30 min to overnight. After washing the resin with DMF, methanol, and dichloromethane, the resin is treated with piperidine in DMF (25%, 2-5 mL) for 10 to 30 min, whereupon the resin is washed as described before. Then 4-bromoacetylbenzoic acid methyl ester (150-500 µmol) in 1-methylpyrrolidin-2-one, dimethylsulphoxide or dichloromethane (1-5 mL), with an equimolar amount of a suitable base added (DIPEA, N-methylmorpholine, triethylamine, or N,N-dimethylaniline), is added and the mixture is agitated at room temperature for 30 min to overnight, whereupon the resin is washed as described before. Next, the resin is treated with a mixture of aqueous sodium hydroxide (2-5 M, 0.5-2 mL), methanol (0.5-2 mL) and tetrahydrofuran (1-4 mL) and agitated at 40-70° C. for 1 h to overnight, followed by repeated washing with DMF, acetic acid in DMF (1-5%), methanol and dichloromethane. Then a solution of HATU (1-2 equivalents, relative to the loading of the resin) in NMP (1-3 mL) and DIPEA (2 equivalents, relative to the amount of HATU) is added and the mixture is agitated for 2-10 min, whereupon 2-amino-5-(2-furyl)-1,3,4-thiadiazole (1-2 equivalents, relative to the amount of HATU) is added and the mixture is heated to 100-120° C. either by conventional heating or by microwave irradiation for 30-180 min. After washing the resin with DMF, methanol and dichloromethane, the final product is cleaved from the support by treatment with trifluoroacetic acid (10%) and triethylsilane (5%) in dichloromethane. After evaporation of the solvents, the final product is purified by flash column chromatography (amino modified stationary phase, methanol in dichloromethane gradient elution) or preparative reverse-phase HPLC-MS.

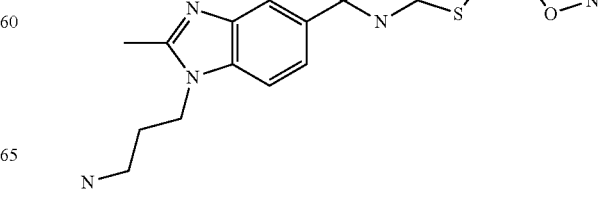

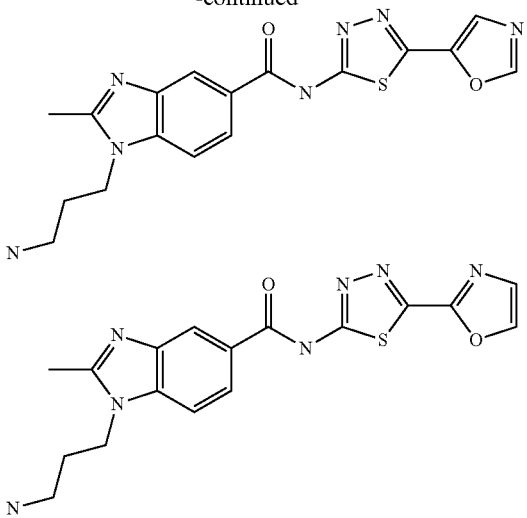

Synthesis of 1-(3-amino-1-propyl)-2-methylbenzimidazole-5-carboxylic acid N-[5-(5-isoxazolyl)-1,3,4-thiadiazol-2-yl] amide (L71), 1-(3-amino-1-propyl)-2-methylbenzimidazole-5-carboxylic acid N-[5-(5-oxazolyl)-1,3,4-thiadiazol-2-yl] amide (L72) and 1-(3-amino-1-propyl)-2-methylbenzimidazole-5-carboxylic acid N-[5-(2-oxazolyl)-1,3,4-thiadiazol-2-yl] amide (L73)

The compounds are synthesized employing General Procedure A. For the synthesis of the respective anilines, the following procedure is applied: A carboxylic acid, namely isoxazole-5-carboxylic acid (for L71), oxazole-5-carboxylic acid (for L72) and oxazole-2-carboxylic acid (for L73) (10 mmol) and thiosemicarbazone (15 mmol) are dissolved in phosphoryl chloride (5 mL) and heated to 60-80° C. for 10 min to 5 h. After cooling to room temperature, the mixture is poured on ice water and adjusted to pH 8-10 with aqueous sodium hydroxide. The product is retrieved from the resulting mixture by filtration or by extraction with a suitable solvent (ethyl acetate, chloroform or dichloromethane), followed by evaporation. The crude product is purified by recrystallization (e.g. from ethanol, isopropanol, ethanol/water mixture) or by column chromatography (normal phase or amino modified stationary phase, methanol in dichloromethane or methanol in chloroform gradient elution). The target compounds are subsequently synthesized from the obtained anilines and 1-[3-(tert-butoxycarbonyl)amino-1-propyl]-2-methylbenzimidazole-5-carboxylic acid (synthesis, see before) as carboxylic acid component employing General Procedure A.

Abbreviations Used in Example 1

DIPEA=N-ethyl-N,N-diisopropylamine
TBME=tert-butyl methyl ether
HATU=O-(7-azabenzotriazol-1-yl)-N,N,N',N'-tetramethyluronium hexafluorophosphate
HPLC-MS=high-performance liquid chromatography coupled to mass spectrometry
ESI-MS=electrospray ionization mass spectrometry
DMF=N,N-dimethylformamide
DMSO=dimethylsulphoxide Example 2: Immobilization of Ligands Ligands from Example 1 were immobilized on NHS-activated SEPHAROSE 4 FF for subsequent chromatography and batch adsorption experiments. Coupling was achieved by formation of an amide bond between the amino group of the spacer-precursor groups on the ligands and the NHS-activated carboxylic acid group of the pre-activated resin.

Dried ligands were redissolved in DMSO at an approximate concentration of 50 mM. In coupling reactions, one volume of ligand dissolved at an approximate concentration of 20 to 30 mM in 90% DMSO and 10% N-Methyl-2-pyrrolidone containing 1 M N,N-Diisopropylethylamine was added to one volume of settled NHS-activated SEPHAROSE 4 FF (GE Healthcare). Reactions were conducted for at least 3 h at 25° C. while shaking vigorously. The supernatant of reactions was withdrawn and resins were washed twice with appropriate solvent. Remaining active groups on resins were blocked with 1 M ethanolamine for 1-2 h at 25° C. Final resins were washed and stored in 30% ethanol at 4° C. until used in subsequent experiments.

Example 3: Chromatographic Evaluation of Ligands (from Example 1)

Experimental

Resins were assessed in packed mode by microtiter plate chromatography. For each column, approximately 30 µl of resin were transferred to a 384-well filter plate and sealed with appropriate top fits. Columns with rProtein A SEPHAROSE 4 FF and MABSORBENT A2P HF were included as controls.

Columns were equilibrated with 6.7 column volumes (cv) of phosphate buffered saline (0.15 M NaCl, 20 mM sodium phosphate, pH 7.3; PBS) prior to injection. Either 3.3 cv of whole IgGs dissolved at 0.5 mg ml$^{-1}$ in PBS or undiluted host cell proteins (HCP) were injected onto columns.

Unbound protein was washed from columns with 5 cv of PBS prior to elution with 5 cv of glycine buffer at pH 2.5. Transferred volumes were spun through columns at 50 g for 1-2 min. During injection of samples, speed was reduced to 10 g and centrifugation time increased to 5-10 min. Effluent fractions were collected in 384-well plates and concentrations of protein were analyzed by Bradford assay. Protein masses $m_i$, $m_{ft}$ and $m_e$ (see below) were calculated as the product of fraction volume and measured protein concentration.

Summary and Results

Binding and elution of several antibodies was demonstrated. Among them were the three humanized therapeutic antibodies Bevacizumab, Tocilizumab and Palivizumab, the chimeric antibody Cetuximab and a human poly-IgG (h-poly-IgG) mixture isolated from human serum. Selectivity of ligands towards the antibodies was determined by investigation of the binding behavior of host cell proteins. Results for commercial resins rProtein A SEPHAROSE 4 FF (rProtein A) and MABSORBENT A2P (A2P) were included for comparison.

The fraction of bound protein was calculated as the difference between the total mass of protein injected $m_i$ and the mass of protein detected in the flowthrough $m_{ft}$, divided by the total mass of protein injected.

$$\text{bound} = \frac{m_i - m_{ft}}{m_i}$$

The yield of protein was calculated as the mass of protein eluted $m_e$, divided by the mass of protein injected $m_i$.

$$\text{yield} = \frac{m_e}{m_i}$$

The selectivity of resins was calculated as the fraction of bound Bevacizumab antibody $B_{Ab}$, divided by the fraction of bound host cell proteins $B_{HCP}$.

$$\text{selectivity} = \frac{B_{Ab}}{B_{HCP}}$$

The fraction of bound protein and the yield of protein were calculated for each resin based on data for whole IgG-antibodies. In the case of host cell proteins, only the fraction of bound protein is given. Selectivity of resins was calculated from data for Bevacizumab whole IgG and host cell proteins. Due to limited experimental precision, selectivity was truncated for values beyond 10.

Chromatography results for resins from Example 2 and reference resins are given in the table below. The results shown for L55-73 are estimated values based on the knowledge obtained from L01-L54.

| | February 8, 2013 HU | | | | | | | | | | | |
|---|---|---|---|---|---|---|---|---|---|---|---|---|
| | Bevacizumab | | Tocilizumab | | Palivizumab | | Cetuximab | | h-poly-IgG | | HCP | |
| Ligand | Bound (%) | Yield (%) | Bound (%) | Yield (%) | Bound (%) | Yield (%) | Bound (%) | Yield (%) | Bound (%) | Yield (%) | Bound (%) | Selectivity |
| L01 | 100 | 90 | 100 | 110 | 99 | 79 | 100 | 89 | 100 | 97 | 33 | 3.0 |
| L02 | 100 | 101 | 100 | 97 | 91 | 92 | 100 | 97 | 100 | 100 | 28 | 3.6 |
| L03 | 100 | 92 | 99 | 103 | 78 | 73 | 99 | 94 | — | — | 45 | 2.2 |
| L04 | 100 | 98 | 100 | 97 | 85 | 84 | 100 | 102 | 100 | 86 | 28 | 3.6 |
| L05 | 100 | 101 | 100 | 103 | 100 | 98 | 100 | 100 | 100 | 104 | 17 | 5.9 |
| L06 | 100 | 84 | — | — | 74 | 74 | — | — | — | — | 31 | 3.2 |
| L07 | 100 | 93 | 100 | 100 | 90 | 88 | 100 | 102 | 94 | 97 | 23 | 4.3 |
| L08 | 100 | 100 | 100 | 100 | 91 | 86 | 100 | 104 | 95 | 95 | 39 | 2.6 |
| L09 | 100 | 97 | 100 | 100 | 100 | 95 | 100 | 105 | 100 | 106 | 39 | 2.6 |
| L10 | 100 | 100 | 100 | 103 | 100 | 96 | 100 | 107 | 100 | 104 | 45 | 2.2 |
| L11 | 100 | 99 | 96 | 90 | 61 | 66 | 98 | 100 | 88 | 87 | 51 | 2.0 |
| L12 | 100 | 104 | 100 | 106 | 100 | 96 | 100 | 95 | 100 | 96 | 40 | 2.5 |
| L13 | 100 | 98 | 100 | 103 | 97 | 92 | 100 | 94 | 97 | 93 | 21 | 4.8 |
| L14 | 100 | 100 | 100 | 101 | 89 | 84 | 100 | 94 | 92 | 90 | 16 | 6.3 |
| L15 | 100 | 91 | 100 | 103 | 100 | 98 | 100 | 94 | 100 | 93 | 39 | 2.6 |
| L16 | 100 | 96 | 100 | 103 | 87 | 88 | 100 | 91 | 88 | 92 | 37 | 2.7 |
| L17 | 100 | 100 | 100 | 100 | 88 | 86 | 100 | 95 | 89 | 96 | 34 | 2.9 |
| L18 | 100 | 102 | 100 | 100 | 100 | 92 | 100 | 98 | 100 | 107 | 29 | 3.4 |
| L19 | 100 | 98 | 100 | 91 | 99 | 85 | 100 | 95 | 98 | 96 | 14 | 7.1 |
| L20 | 100 | 100 | 100 | 92 | 100 | 88 | 100 | 96 | 100 | 105 | 35 | 2.9 |
| L21 | 100 | 100 | 98 | 86 | 85 | 72 | 100 | 98 | 82 | 81 | 2 | 10.0 |
| L22 | 100 | 104 | 100 | 94 | 100 | 90 | 100 | 98 | 100 | 108 | 30 | 3.3 |
| L23 | 100 | 107 | 100 | 95 | 100 | 93 | 100 | 98 | 100 | 103 | 13 | 7.7 |
| L24 | 100 | 101 | 100 | 93 | 100 | 90 | 100 | 97 | 100 | 99 | 12 | 8.3 |
| L25 | 100 | 99 | 100 | 93 | 100 | 85 | 99 | 97 | 100 | 92 | 4 | 10.0 |
| L26 | 100 | 103 | 72 | 73 | 63 | 54 | 94 | 90 | 63 | 71 | 2 | 10.0 |
| L27 | 100 | 103 | 61 | 64 | 41 | 34 | 88 | 87 | 50 | 58 | 4 | 10.0 |
| L28 | 100 | 95 | 98 | 101 | 58 | 60 | 89 | 93 | 63 | 72 | 12 | 8.3 |
| L29 | 100 | 98 | 90 | 94 | 72 | 64 | 99 | 92 | 76 | 72 | 18 | 5.6 |
| L30 | 100 | 100 | 100 | 99 | 93 | 79 | 100 | 95 | 94 | 88 | 21 | 4.8 |
| L31 | 100 | 95 | 100 | 95 | 100 | 89 | 100 | 91 | 100 | 95 | 20 | 5.0 |
| L32 | 100 | 103 | 100 | 98 | 91 | 81 | 100 | 89 | 91 | 91 | 44 | 2.3 |
| L33 | 100 | 105 | 100 | 100 | 100 | 92 | 100 | 94 | 100 | 94 | 34 | 2.9 |
| L34 | 100 | 104 | 85 | 84 | 78 | 69 | 100 | 90 | 78 | 74 | 10 | 10.0 |
| L35 | 100 | 104 | 100 | 98 | 100 | 87 | 100 | 89 | 100 | 96 | 29 | 3.4 |
| L36 | 100 | 104 | 90 | 96 | 93 | 89 | 99 | 94 | 81 | 87 | 9 | 10.0 |
| L37 | 100 | 87 | 100 | 103 | 100 | 91 | 100 | 94 | 100 | 101 | 25 | 4.0 |
| L38 | 100 | 106 | 99 | 97 | 95 | 91 | 100 | 103 | 99 | 98 | 35 | 2.9 |
| L39 | 100 | 85 | 100 | 99 | 100 | 96 | 100 | 96 | 100 | 98 | 10 | 10.0 |
| L40 | 100 | 101 | 99 | 101 | 89 | 80 | 100 | 94 | 98 | 87 | 20.5 | 4.9 |
| L41 | 100 | 103 | 100 | 103 | 98 | 87 | 100 | 96 | 100 | 95 | 13 | 7.7 |
| L42 | 100 | 98 | 100 | 106 | 97 | 91 | 100 | 96 | 100 | 103 | 13.5 | 7.4 |
| L43 | 100 | 95 | 100 | 108 | 98 | 91 | 100 | 95 | 100 | 94 | 18 | 5.6 |
| L44 | 100 | 88 | 100 | 106 | 100 | 92 | 100 | 96 | 100 | 96 | 16 | 6.3 |
| L45 | 100 | 93 | 100 | 102 | 100 | 91 | 100 | 96 | 100 | 99 | 15 | 6.7 |
| L46 | 100 | 103 | 100 | 109 | 98 | 95 | 100 | 94 | 100 | 98 | 17 | 5.9 |
| L47 | 100 | 100 | 99 | 108 | 98 | 89 | 100 | 93 | 100 | 97 | 13 | 7.7 |
| L48 | 100 | 100 | 100 | 105 | 95 | 86 | 100 | 96 | 100 | 91 | 16.5 | 6.1 |
| L49 | 100 | 97 | 100 | 96 | 100 | 102 | 100 | 82 | 100 | 97 | 0 | 10.0 |
| L50 | 100 | 103 | 80 | 84 | 72 | 78 | 100 | 81 | 76 | 82 | 0 | 10.0 |
| L51 | 100 | 95 | 98 | 100 | 94 | 88 | 100 | 80 | 97 | 98 | 15 | 6.7 |
| L52 | 100 | 96 | 86 | 86 | 80 | 85 | 99 | 81 | 83 | 89 | 9 | 10.0 |
| L53 | 100 | 96 | 100 | 91 | 100 | 101 | 100 | 81 | 100 | 95 | 11 | 9.1 |

-continued

February 8, 2013 HU

| Ligand | Bevacizumab Bound (%) | Bevacizumab Yield (%) | Tocilizumab Bound (%) | Tocilizumab Yield (%) | Palivizumab Bound (%) | Palivizumab Yield (%) | Cetuximab Bound (%) | Cetuximab Yield (%) | h-poly-IgG Bound (%) | h-poly-IgG Yield (%) | HCP Bound (%) | HCP Selectivity |
|---|---|---|---|---|---|---|---|---|---|---|---|---|
| L54 | 100 | 95 | 100 | 100 | 100 | 93 | 100 | 90 | 100 | 99 | 4 | 10.0 |
| L55 | 100 | >80 | >95 | >80 | >80 | >70 | 100 | >80 | >80 | >70 | <40 | >2, 5 |
| L56 | 100 | >80 | >95 | >80 | >80 | >70 | 100 | >80 | >80 | >70 | <40 | >2, 5 |
| L57 | 100 | >80 | >95 | >80 | >80 | >70 | 100 | >80 | >80 | >70 | <40 | >2, 5 |
| L58 | 100 | >80 | >95 | >80 | >80 | >70 | 100 | >80 | >80 | >70 | <40 | >2, 5 |
| L59 | 100 | >80 | >90 | >80 | >60 | >50 | >95 | >80 | >80 | >70 | <40 | >3, 3 |
| L60 | 100 | >80 | >95 | >80 | >80 | >70 | 100 | >80 | >80 | >70 | <40 | >5 |
| L61 | 100 | >80 | >95 | >80 | >80 | >70 | 100 | >80 | >80 | >70 | <40 | >5 |
| L62 | 100 | >80 | >95 | >80 | >80 | >70 | 100 | >80 | >80 | >70 | <40 | >5 |
| L63 | 100 | >80 | >95 | >80 | >80 | >70 | 100 | >80 | >80 | >70 | <20 | >5 |
| L64 | 100 | >80 | >90 | >80 | >60 | >50 | >95 | >80 | >80 | >50 | <20 | >5 |
| L65 | 100 | >80 | >95 | >80 | >80 | >70 | 100 | >80 | >80 | >70 | <30 | >3, 3 |
| L66 | 100 | >80 | >95 | >80 | >80 | >70 | 100 | >80 | >80 | >70 | <30 | >3, 3 |
| L67 | 100 | >80 | >95 | >80 | >80 | >70 | 100 | >80 | >80 | >70 | <30 | >3, 3 |
| L68 | 100 | >80 | >95 | >80 | >80 | >70 | 100 | >80 | >80 | >70 | <30 | >3, 3 |
| L69 | 100 | >80 | >90 | >80 | >60 | >50 | >95 | >80 | >80 | >50 | <30 | >3, 3 |
| L70 | 100 | >80 | >80 | >80 | >50 | >40 | >80 | >80 | >80 | >40 | <40 | >2, 5 |
| L71 | 100 | >80 | >90 | >80 | >60 | >50 | >95 | >80 | >80 | >50 | <20 | >5 |
| L72 | 100 | >80 | >90 | >80 | >60 | >50 | >95 | >80 | >80 | >50 | <20 | >5 |
| L73 | 100 | >80 | >90 | >80 | >60 | >50 | >95 | >80 | >80 | >50 | <20 | >5 |
| rProtein A | 100 | 94 | 100 | 95 | 100 | 100 | 100 | 100 | 95 | 79 | 0 | 10.0 |
| A2P | 100 | 84 | 97 | 77 | 100 | 89 | — | — | 100 | 82 | 100 | 1.0 |

Controls bound all antibodies to nearly 100%. Whereas Protein A bound no host cell proteins (HCP) at all, A2P showed high binding properties towards them. Resulting selectivity indices were 10.0 for Protein A and 1.0 for A2P.

Resins from Example 2 can be classified into three different groups according to their antibody binding properties and selectivities. Ligands of group one are characterized by antibody binding rates of at least 90% and selectivity indices of at least 7 (e.g. L24, L25, L39, L53 and L54). Ligands of the second group showed reduced antibody binding rates (80% to 89%) towards at least one of the tested antibodies and/or selectivities between 4 and 6.9 (e.g. L5, L30, L31 and L52). Ligands of the third group bound at least one of the tested antibodies to less than 80% and/or had selectivity indices below 4 (e.g. L1, L18, L32 and L50).

Example 4: Isotherms and Time-Scales of Binding

Experimental

Experiments were performed with Bevacizumab as antibody. Parameters of Langmuir isotherms for purified antibody were determined by batch adsorption experiments in 96-well microtiter plates. In each well, 10 µl of sorbent slurry (50% v/v) were mixed with 100 µl of protein solution. Initial concentrations varied from 0.05-5 mg/ml in phosphate-buffered saline (0.15 M NaCl, 20 mM phosphate buffer, pH 7.3; PBS). Reactions were agitated vigorously at 25° C. for at least 3 h. Afterwards, antibody concentration in the supernatants were measured by Bradford assay. Data was evaluated by direct fitting of the values with the Langmuir isotherm equation (1).

Uptake kinetics was investigated similarly by batch adsorption in 96-well filter plates. Again, 10 µl of sorbent slurry (50% v/v) were mixed with 100 µl of protein solution. However, a fixed initial concentration of 0.75 mg/ml Bevacizumab in PBS was used. Reactions were agitated vigorously at 25° C. for up to 80 min. Supernatants were separated rapidly by spinning through filters after 2.5, 5, 10, 20, 40 and 80 minutes and sampled for analysis. Concentrations of the antibody were analyzed by Bradford assay.

Summary and Results

A subset of immobilized ligands from Example 1 was characterized with respect to their affinity and maximum capacity towards Bevacizumab. Furthermore, the time-scale required for binding was determined for some ligands. Commercial resins rProtein A SEPHAROSE 4 FF (rProtein A) and MABSORBENT A2P (A2P) were included for comparison.

Parameters of Langmuir isotherms, i.e. dissociation constants $K_d$ and maximum capacities $q_m$, were determined from the measured concentrations in the supernatants. Parameters were estimated by numerical fitting of the model equation derived by Chase (1)

Uptake kinetics was characterized by a time-scale of binding $t_{0.8}$, which was defined as the time after which 80% of the equilibrium saturation of resin with antibody had occurred. For determination of $t_{0.8}$, measured concentrations in the supernatant were interpolated by fitting of double-exponentials and values of $t_{0.8}$ were read out from graphs (2). Parameters of Langmuir isotherms and time-scales of binding for resins from Example 2 as well as for reference resins are reported in the table below.

| Ligand | $k_d$ (mg/ml) | $q_m$ (mg/ml) | $t_{0.8}$ (min) |
|---|---|---|---|
| L01 | 0.073 | 40 | 9.2 |
| L02 | 0.113 | 41 | — |
| L05 | 0.076 | 47 | 9.8 |
| L07 | 0.066 | 38 | 8.8 |
| L13 | 0.091 | 37 | 7.0 |
| L14 | 0.067 | 35 | — |
| L19 | 0.199 | 42 | 8.9 |
| L23 | 0.046 | 46 | 7.7 |
| L24 | 0.224 | 42 | 9.4 |
| L25 | 0.038 | 37 | 6.6 |
| L30 | 0.122 | 40 | 9.3 |

-continued

| Ligand | $k_d$ (mg/ml) | $q_m$ (mg/ml) | $t_{0.8}$ (min) |
|---|---|---|---|
| L31 | 0.048 | 45 | 5.3 |
| L36 | 0.234 | 35 | — |
| L39 | 0.081 | 49 | 7.8 |
| L40 | 0.086 | 39 | 9.2 |
| L41 | 0.082 | 41 | 9.0 |
| L42 | 0.125 | 45 | 7.6 |
| L43 | 0.162 | 43 | 8.2 |
| L44 | 0.105 | 53 | 7.7 |
| L46 | 0.070 | 48 | 6.0 |
| L47 | 0.064 | 43 | 5.6 |
| L48 | 0.282 | 37 | 6.3 |
| L49 | 0.152 | 45 | 8.9 |
| L51 | 0.098 | 34 | 8.8 |
| L53 | 0.130 | 34 | 11.8 |
| L54 | 0.048 | 35 | 8.4 |
| rProtein A | 0.005 | 41 | 8.9 |
| A2P | 0.049 | 68 | 9.2 |

Highest affinity was observed for rProtein A, which had a $K_d$ of 0.005 mg/ml. Dissociation constants of A2P, resins L01, L05, L07, L13, L14, L23, L25, L31, L39, L40, L41, L46, L47, L51 and L54 were lower by one order of magnitude and ranged between 0.038 mg/ml and 0.098 mg/ml. Dissociation constants of the residual resins were lower by two orders of magnitude and ranged from 0.105 mg/ml to 0.282 mg/ml. Concerning maximum capacity, the highest capacity was measured for A2P (68 mg per ml of resin). rProtein A had a maximum capacity of 41 mg per ml of resin. Maximum capacities of resins from Example 2 varied between 34 and 53 mg per ml of resin. Time scales of binding were 8.9 min for rProtein A, 9.2 min for A2P and 5.3 min to 11.8 min for resins from Example 2.

Example 5: Dynamic Binding Capacity

Experimental

Dynamic binding capacities were determined by column chromatography with purified Bevacizumab. Resins were packed into analytical columns of 25 mm length and 3 mm inner diameter. Columns were fed with 1 mg/ml antibody in phosphate-buffered saline (150 mM NaCl, 20 mM phosphate buffer, pH 7.3) at a flow rate of 50 cm/h (3 min column residence time), while the concentration of antibody in effluents was monitored online via absorbance at 280 nm. Antibody was loaded until complete breakthrough of the feed. Dynamic binding capacities were determined at the 10% breakthrough. Equilibrium capacities were determined by integration of the area above the breakthrough curve. Bound antibody was stripped from columns by elution with glycine at pH 3.0.

Summary and Results

Dynamic (binding) capacity for Bevacizumab as a function of flow rate was determined for L05 (from Example 2) and for rProtein A SEPHAROSE 4 FF (rProtein A). It was calculated as the time $t_{0.1}$ after which 10% breakthrough occurred, multiplied by the flow rate F and feed concentration $c_f$.

$$\text{dynamic capacity} = t_{0.1} \cdot F \cdot c_f$$

Equilibrium capacity is defined as the maximum amount of antibody that binds to a column for a given feed stream concentration. It was calculated by evaluation of the following integral $$\text{equilibrium capacity} = \int_0^\infty [c_f - c(t)] \cdot F \, dt$$

containing the feed concentration $c_f$, effluent concentration over time $c(t)$ and flow rate F. The integral was evaluated numerically. Integration was limited to the time after which complete breakthrough had occurred. Calculations of dynamic capacity and equilibrium capacity were both corrected for the hold-up of columns and the chromatography system. Capacities were normalized by the volume of resin in columns Dynamic binding capacities for L05 and rProtein A SEPHAROSE 4 FF as a function of flow rate and equilibrium binding capacities for a feed concentration of 1 mg/ml Bevacizumab are given in the table below.

For rProtein A a dynamic binding capacity of 28 mg per ml of resin was determined. L05 had a dynamic capacity of 25 mg per ml of resin. The calculated equilibrium capacity was 40 mg per ml of resin for rProtein A and 39 mg per ml of resin for L05.

| Ligand | Dynamic Capacity (mg/ml) | Equilibrium Capacity (mg/ml) |
|---|---|---|
| L05 | 25 | 39 |
| rProtein A | 28 | 40 |

Example 6: Alkaline Stability

A subset of ligands from Example 1 was tested for its alkaline stability. Ligands were treated with 0.5 M sodium hydroxide at 25° C. for 8 days. Hydrolysis was monitored by LC-MS analysis.

| Ligand | $t_{0.5}$ (h) |
|---|---|
| L01 | 840 |
| L02 | >999 |
| L04 | >999 |
| L05 | >999 |
| L07 | >999 |
| L13 | >999 |
| L14 | >999 |
| L19 | >999 |
| L23 | >999 |
| L24 | >999 |
| L25 | >999 |
| L30 | 903 |
| L36 | >999 |
| L39 | >999 |
| L40 | 782 |
| L41 | >999 |
| L42 | >999 |
| L43 | >999 |
| L44 | >999 |
| L45 | >999 |
| L46 | 719 |
| L47 | >999 |

Most ligands showed half-lifes of more than 999 h in the presence of 0.5 M NaOH. Residual ligands showed half-lifes between 719 h and 903 h.

Example 7: Purification of Antibody from Cell Culture Supernatant

Experimental

Suitability of resins for the purification of antibody from cell culture supernatant was assessed by column chromatography. Bevacizumab spiked into host cell proteins at a concentration of 0.12 mg/ml was used as feed (20% purity). In addition, chromatography runs with host cell proteins and pure antibody alone were conducted. 25 column volumes of corresponding samples were injected per run. Columns were equilibrated and washed with PBS before and after injection. Bound protein was eluted with 50 mM glycine at pH 3.0. Purity was determined by integrating and balancing the area of the elution peaks of the three single runs. Yield was expressed as the relative recovery taking the amount of antibody eluted from a Protein A column which was operated in parallel as 100%.

Summary and Results

Antibody was purified from cell culture supernatant by chromatography on a subset of resins from Example 2. Chromatography on commercial resin rProtein A SEPHAROSE FF (rProtein A) was included for comparison. Three chromatography runs under identical conditions were conducted on each resin, either injecting the antibody, host cell proteins or a mixture of the latter.

Operation 'yield' after chromatography was calculated from the runs with pure antibody. It was expressed as the area of the elution peak from the run with the ligand $A_{E, Ligand}$ proportionally to the area of the elution peak from a run on Protein A $A_{E, Protein\ A}$.

$$\text{yield} = \frac{A_{E, ligand}}{A_{E, Protein\ A}}$$

The 'purity' of the antibody after chromatography of the mixture was calculated by balancing the area of the elution peak of the run with the spiked antibody $A_{E, Mix}$ with either the run with the pure antibody $A_{E, Ab}$ or with the run of the spiked antibody corrected by the run with HCP $A_{E, HCP}$.

$$\text{purity} = \frac{A_{E, Mix} - A_{E, HCP}}{A_{E, Mix}} \quad \text{purity} = \frac{A_{E, Ab}}{A_{E, Mix}}$$

Purity and yield obtained after chromatography on several resins from Example 2 and reference resins are given in the table below.

Within experimental precision, yields were 100% for all tested resins. Purity was highest after chromatography on rProtein A (98%), followed by chromatography on resin L25 (93%) and resins L24 and L39 (both 91%). Purity after chromatography on residual resins ranged between 80% and 89%.

| Ligand | purity (%) | yield (%) |
|---|---|---|
| L05 | 86 | 100 |
| L19 | 80 | 100 |
| L23 | 82 | 100 |
| L24 | 91 | 100 |
| L25 | 93 | 100 |
| L39 | 91 | 100 |
| L40 | 85 | 100 |
| L47 | 85 | 100 |
| L42 | 89 | 100 |
| rProtein A | 98 | 100 |

DOCUMENTS CITED IN THE EXAMPLES

1. Chase H A. Prediction of the performance of preparative affinity chromatography. J Chromatogr 1984; 297:179-202.
2. Coffman J L, Kramarczyk J F, Kelley B D. High-throughput screening of chromatographic separations: I. Method development and column modeling. Biotechnology and Bioengineering 2008; 100(4):605-618.

The invention claimed is:

1. A method of affinity purification of an antibody or a fragment of an antibody, comprising contacting the antibody or the fragment of the antibody with a ligand-substituted matrix, wherein the ligand-substituted matrix comprises:
   a support material and
   at least one ligand covalently bonded through a primary amino group of the ligand to the support material and binding to the Fc part of the antibody or the antibody fragment, wherein the ligand is selected from the group consisting of:

1-(8-Amino-3,5-dioxa-1-octyl)-2-methylbenzimidazole-5-carboxylic acid N-[5-(2-furyl)-1,3,4-thiadiazol-2-yl]amide, 1-(3-Amino-1-propyl)-2-methylbenzimidazole-5-carboxylic acid N-[5-(2-furyl)-1,3,4-thiadiazol-2-yl]amide, and

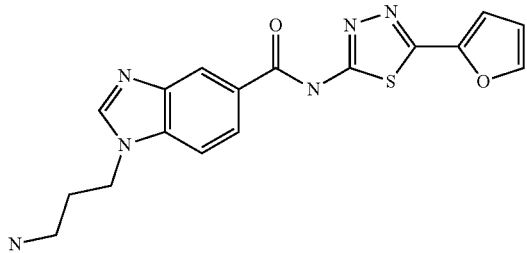 [SMILES: NCCCn1cnc2cc(C(=O)Nc3nnc(-c4ccco4)s3)ccc21]

1-(3-Amino-1-propyl)benzimidazole-5-carboxylic acid N-[5-(2-furyl)-1,3,4-thiadiazol-2-yl]amide.

2. The method according to claim 1, wherein the ligand is:

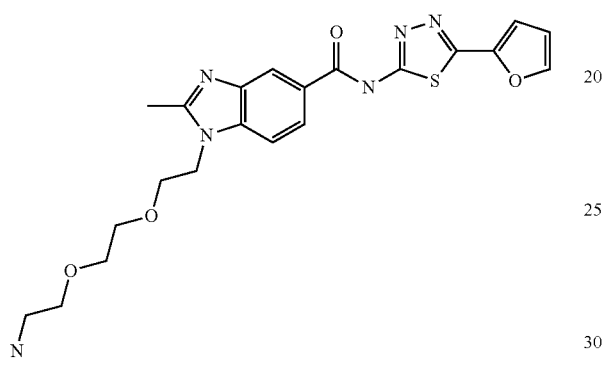

1-(8-Amino-3,5-dioxa-1-octyl)-2-methylbenzimidazole-5-carboxylic acid N-[5-(2-furyl)-1,3,4-thiadiazol-2-yl]amide.

3. The method according to claim 1, wherein the ligand is:

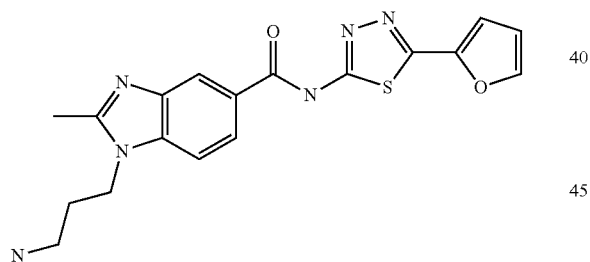

1-(3-Amino-1-propyl)-2-methylbenzimidazole-5-carboxylic acid N-[5-(2-furyl)-1,3,4-thiadiazol-2-yl]amide.

4. The method according to claim 1, wherein the ligand is:

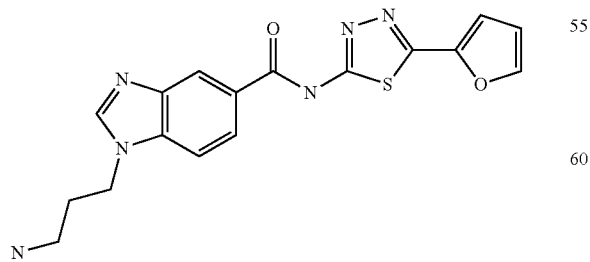

1-(3-Amino-1-propyl)benzimidazole-5-carboxylic acid N-[5-(2-furyl)-1,3,4-thiadiazol-2-yl]amide.

5. The method according to claim 1, wherein the antibody is an IgG type antibody.

6. The method according to claim 1, wherein the antibody fragment is a Fc fragment or domain.

7. The method according to claim 1, wherein the antibody belongs to the IgG$_1$, IgG$_2$, IgG$_3$ or IgG$_4$ antibody class.

8. A method for affinity purification of an Fc fusion protein comprising contacting the Fc fusion protein to be purified with a ligand-substituted matrix, wherein the ligand-substituted matrix comprises:

a support material and at least one ligand covalently bonded through a primary amino group of the ligand to the support material and binding to the Fc part of the Fc fusion protein, wherein the ligand is selected from the group consisting of:

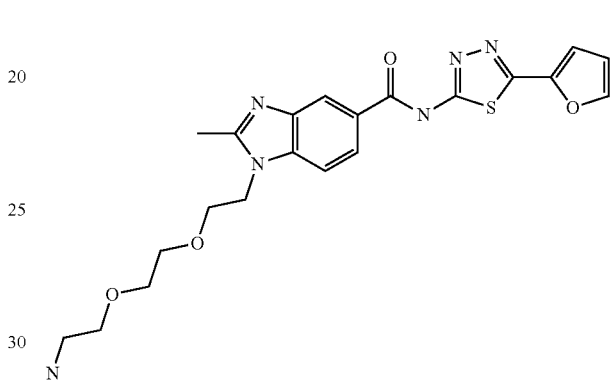

1-(8-Amino-3,5-dioxa-1-octyl)-2-melhylbenzimidazole-5-carboxylic acid N-[5-(2-furyl)-1,3,4-thiadiazol-2-yl]amide,

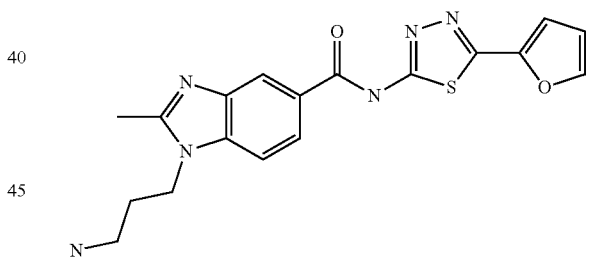

1-(3-Amino-1-propyl)-2-methylbenzimidazole-5-carboxylic acid N-[5-(2-furyl)-1,3,4-thiadiazol-2-yl]amide, and

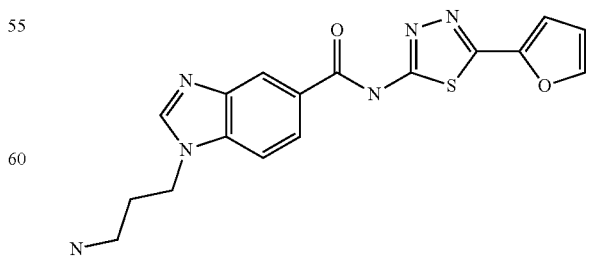

1-(3-Amino-1-propyl)benzimidazole-5-carboxylic acid N-[5-(2-furyl)-1,3,4-thiadiazol-2-yl]amide.

9. The method according to claim 8, wherein the ligand is:

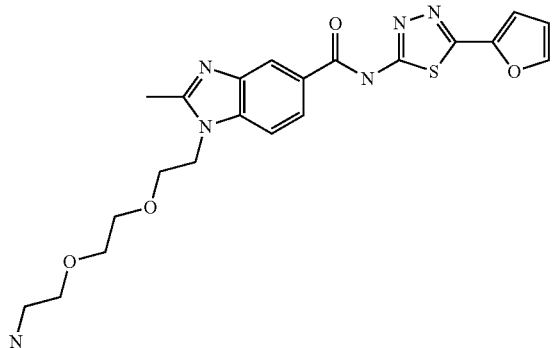 [SMILES: Cc1nc2cc(C(=O)Nc3nnc(-c4ccco4)s3)ccc2n1CCOCCOCCN]

1-(8-Amino-3,5-dioxa-1-octyl)-2-methylbenzimidazole-5-carboxylic acid N-[5-(2-furyl)-1,3,4-thiadiazol-2-yl]amide.

10. The method according to claim 8, wherein the ligand is:

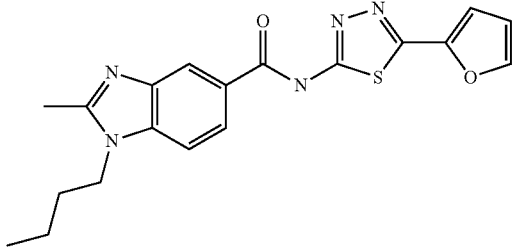 [SMILES: CCCCn1c(C)nc2cc(C(=O)Nc3nnc(-c4ccco4)s3)ccc21]

1-(3-Amino-1-propyl)-2-methylbenzimidazole-5-carboxylic acid N-[5-(2-furyl)-1,3,4-thiadiazol-2-yl]amide.

11. The method according to claim 8, wherein the ligand is:

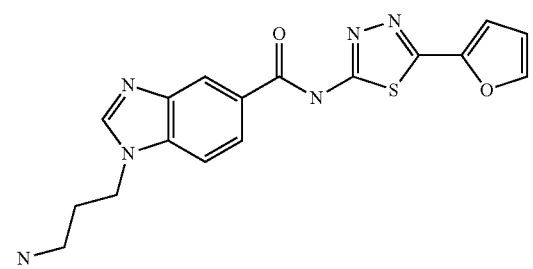 [SMILES: NCCCn1cnc2cc(C(=O)Nc3nnc(-c4ccco4)s3)ccc21]

1-(3-Amino-1-propyl)benzimidazole-5-carboxylic acid N-[5-(2-furyl)-1,3,4-thiadiazol-2-yl]amide.

12. A method for affinity purification of an antibody or a fragment of an antibody comprising contacting the antibody or the fragment of the antibody with a ligand, wherein the ligand is selected from the group consisting of:

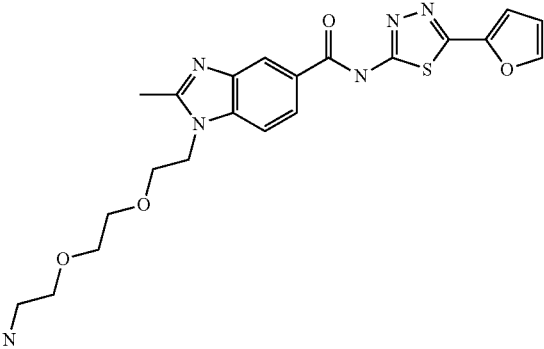 [SMILES: Cc1nc2cc(C(=O)Nc3nnc(-c4ccco4)s3)ccc2n1CCOCCOCCN]

1-(8-Amino-3,5-dioxa-1-octyl)-2-methylbenzimidazole-5-carboxylic acid N-[5-(2-furyl)-1,3,4-thiadiazol-2-yl]amide,

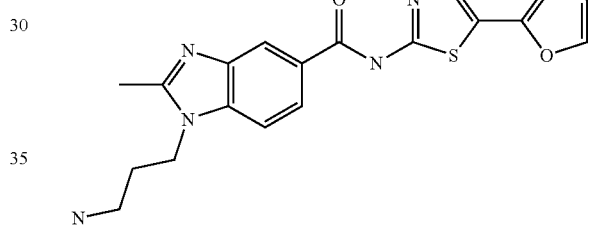

1-(3-Amino-1-propyl)-2-methylbenzimidazole-5-carboxylic acid N-[5-(2-furyl)-1,3,4-thiadiazol-2-yl]amide, and

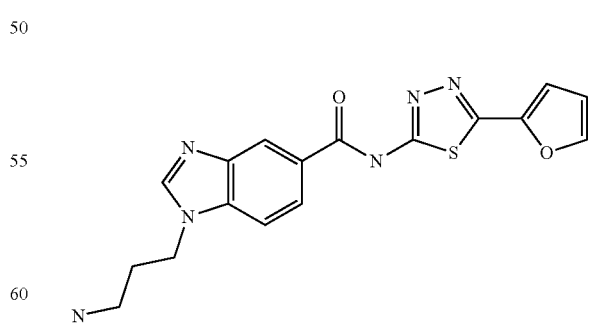

1-(3-Amino-1-propyl)benzimidazole-5-carboxylic acid N-[5-(2-furyl)-1,3,4-thiadiazol-2-yl]amide.

13. The method according to claim 12, wherein the ligand is:

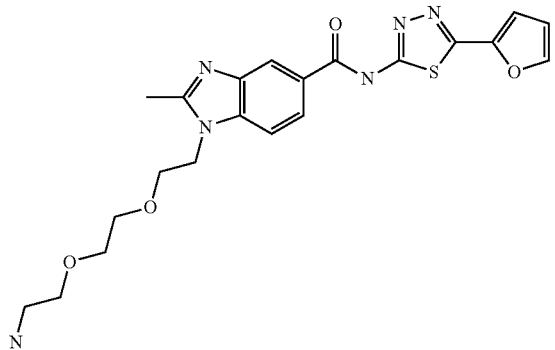 [SMILES: Cc1nc2cc(C(=O)Nc3nnc(-c4ccco4)s3)ccc2n1CCOCCOCCN]

1-(8-Amino-3,5-dioxa-1-oclyl)-2-methylbenzimidazole-5-carboxylic acid N-[5-(2-furyl)-1,3,4-thiadiazol-2-yl]amide.

14. The method according to claim 12, wherein the ligand is:

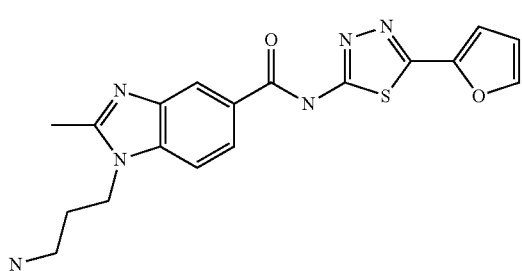 [SMILES: Cc1nc2cc(C(=O)Nc3nnc(-c4ccco4)s3)ccc2n1CCCN]

1-(3-Amino-1-propyl)-2-methylbenzimidazole-5-carboxylic acid N-[5-(2-furyl)-1,3,4-thiadiazol-2-yl]amide.

15. The method according to claim 12, wherein the ligand is:

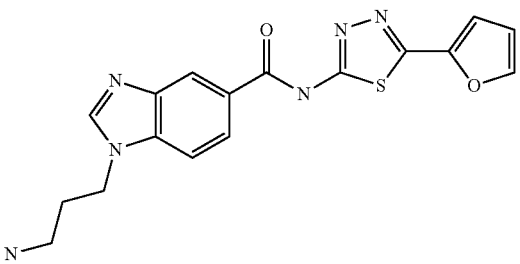 [SMILES: NCCCn1cnc2cc(C(=O)Nc3nnc(-c4ccco4)s3)ccc21]

1-(3-Amino-1-propyl)benzimidazole-5-carboxylic acid N-[5-(2-furyl)-1,3,4-thiadiazol-2-yl]amide.

16. The method according to claim 12, wherein the ligand is attached to an appropriate matrix prior to contacting the antibody or the fragment of the antibody through a primary amino group of the ligand.

* * * * *